US012319688B2

(12) United States Patent
Ohsawa et al.

(10) Patent No.: US 12,319,688 B2
(45) Date of Patent: Jun. 3, 2025

(54) LIGHT-EMITTING DEVICE, LIGHT-EMITTING APPARATUS, ELECTRONIC DEVICE, AND LIGHTING DEVICE

(71) Applicant: SEMICONDUCTOR ENERGY LABORATORY CO., LTD., Atsugi (JP)

(72) Inventors: Nobuharu Ohsawa, Kanagawa (JP); Satoshi Seo, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 692 days.

(21) Appl. No.: 17/604,484

(22) PCT Filed: Apr. 13, 2020

(86) PCT No.: PCT/IB2020/053463
§ 371 (c)(1),
(2) Date: Oct. 18, 2021

(87) PCT Pub. No.: WO2020/217129
PCT Pub. Date: Oct. 29, 2020

(65) Prior Publication Data
US 2022/0220105 A1 Jul. 14, 2022

(30) Foreign Application Priority Data
Apr. 25, 2019 (JP) .................. 2019-084536

(51) Int. Cl.
*C07D 471/04* (2006.01)
*C07D 207/325* (2006.01)
(Continued)

(52) U.S. Cl.
CPC ....... *C07D 471/04* (2013.01); *C07D 207/325* (2013.01); *C07D 403/14* (2013.01);
(Continued)

(58) Field of Classification Search
CPC ........... H10K 2101/27; H10K 2101/30; H10K 2101/40; H10K 85/615
See application file for complete search history.

(56) References Cited

U.S. PATENT DOCUMENTS

| 5,759,444 A | 6/1998 | Enokida et al. |
| 6,097,147 A | 8/2000 | Baldo et al. |

(Continued)

FOREIGN PATENT DOCUMENTS

| CN | 102884649 A | 1/2013 |
| CN | 105474749 A | 4/2016 |

(Continued)

OTHER PUBLICATIONS

Jeong et al., Journal of Photonics for Energy, vol. 5, 2015, 057608, pp. 1-23.*

(Continued)

*Primary Examiner* — Vu A Nguyen
(74) *Attorney, Agent, or Firm* — Fish & Richardson P.C.

(57) ABSTRACT

A light-emitting device with high emission efficiency is provided. The light-emitting device includes a fluorescent substance and a phosphorescent substance or a thermally activated delayed fluorescent material; the fluorescent substance includes a luminophore and five or more protecting groups; the luminophore is a condensed aromatic ring or a condensed heteroaromatic ring; the five or more protecting groups each have any one of an alkyl group having 1 to 10 carbon atoms, a substituted or unsubstituted cycloalkyl group having 3 to 10 carbon atoms, and a trialkylsilyl group having 3 to 12 carbon atoms; the lowest singlet excitation energy level of the fluorescent substance is higher than the lowest triplet excitation energy level of the phosphorescent substance or the thermally activated delayed fluorescent material; and light emission can be obtained from both the (Continued)

phosphorescent substance and the phosphorescent substance or the thermally activated delayed fluorescent material.

14 Claims, 25 Drawing Sheets

(51) Int. Cl.
    *C07D 403/14*     (2006.01)
    *C07D 409/14*     (2006.01)
    *C07F 7/08*     (2006.01)
    *H10K 50/11*     (2023.01)
    *H10K 50/84*     (2023.01)
    *H10K 85/60*     (2023.01)
    *H10K 101/00*     (2023.01)
    *H10K 101/10*     (2023.01)
    *H10K 101/30*     (2023.01)
    *H10K 101/40*     (2023.01)

(52) U.S. Cl.
    CPC .......... *C07D 409/14* (2013.01); *C07F 7/0805* (2013.01); *H10K 85/626* (2023.02); *H10K 85/633* (2023.02); *H10K 85/654* (2023.02); *H10K 85/6572* (2023.02); *H10K 85/6576* (2023.02); *H10K 50/11* (2023.02); *H10K 50/841* (2023.02); *H10K 2101/10* (2023.02); *H10K 2101/27* (2023.02); *H10K 2101/30* (2023.02); *H10K 2101/40* (2023.02); *H10K 2101/90* (2023.02)

(56) References Cited

U.S. PATENT DOCUMENTS

| | | |
|---|---|---|
| 6,376,107 B1 | 4/2002 | Heuer et al. |
| 6,863,997 B2 | 3/2005 | Thompson et al. |
| 7,175,922 B2 | 2/2007 | Jarikov et al. |
| 7,183,010 B2 | 2/2007 | Jarikov |
| 7,332,857 B2 | 2/2008 | Seo et al. |
| 7,572,522 B2 | 8/2009 | Seo et al. |
| 7,597,967 B2 | 10/2009 | Kondakova et al. |
| 7,816,017 B2 | 10/2010 | Funahashi et al. |
| 7,943,925 B2 | 5/2011 | Yamazaki |
| 7,993,760 B2 | 8/2011 | Komori et al. |
| 8,034,465 B2 | 10/2011 | Liao et al. |
| 8,247,086 B2 | 8/2012 | Inoue et al. |
| 8,274,214 B2 | 9/2012 | Ikeda et al. |
| 8,476,823 B2 | 7/2013 | Kuma et al. |
| 8,729,310 B2 | 5/2014 | Osaka et al. |
| 8,766,249 B2 | 7/2014 | Sawada et al. |
| 8,803,134 B2 | 8/2014 | Inoue. et al. |
| 8,853,680 B2 | 10/2014 | Yamazaki et al. |
| 8,941,297 B2 | 1/2015 | Kaiser et al. |
| 8,963,127 B2 | 2/2015 | Pieh et al. |
| 8,981,355 B2 | 3/2015 | Seo |
| 8,993,129 B2 | 3/2015 | Endo et al. |
| 8,994,263 B2 | 3/2015 | Shitagaki et al. |
| 9,054,317 B2 | 6/2015 | Monkman et al. |
| 9,082,995 B2 * | 7/2015 | Nishimura ........... H10K 50/125 |
| 9,159,942 B2 | 10/2015 | Seo et al. |
| 9,175,213 B2 | 11/2015 | Seo et al. |
| 9,356,250 B2 | 5/2016 | Ohsawa et al. |
| 9,362,517 B2 | 6/2016 | Ohsawa et al. |
| 9,515,279 B2 | 12/2016 | Ishisone et al. |
| 9,604,928 B2 | 3/2017 | Shitagaki et al. |
| 9,947,876 B2 | 4/2018 | Kawamura et al. |
| 10,347,851 B2 | 7/2019 | Lennartz et al. |
| 10,439,005 B2 | 10/2019 | Ishisone et al. |
| 10,910,565 B2 | 2/2021 | Ogiwara et al. |
| 11,049,908 B2 | 6/2021 | Ishisone et al. |
| 11,968,894 B2 | 4/2024 | Ogiwara et al. |
| 2004/0253478 A1 | 12/2004 | Thompson et al. |
| 2005/0048310 A1 | 3/2005 | Cocchi et al. |
| 2005/0221116 A1 | 10/2005 | Cocchi et al. |
| 2006/0134464 A1 | 6/2006 | Nariyuki |
| 2006/0186376 A1 | 8/2006 | Yamamoto et al. |
| 2006/0202190 A1 | 9/2006 | Funahashi |
| 2006/0228577 A1 | 10/2006 | Nagara |
| 2007/0007884 A1 | 1/2007 | Iwanaga et al. |
| 2007/0090756 A1 | 4/2007 | Okada et al. |
| 2007/0244320 A1 | 10/2007 | Inoue et al. |
| 2007/0252511 A1 | 11/2007 | Funahashi |
| 2008/0160345 A1 | 7/2008 | Inoue et al. |
| 2008/0286604 A1 | 11/2008 | Inoue et al. |
| 2009/0166563 A1 | 7/2009 | Yokoyama et al. |
| 2010/0145044 A1 | 6/2010 | Inoue et al. |
| 2010/0314644 A1 | 12/2010 | Nishimura et al. |
| 2011/0001146 A1 | 1/2011 | Yamazaki et al. |
| 2011/0210316 A1 | 9/2011 | Kadoma et al. |
| 2011/0215714 A1 | 9/2011 | Seo et al. |
| 2012/0098417 A1 | 4/2012 | Inoue et al. |
| 2012/0205687 A1 | 8/2012 | Yamazaki et al. |
| 2012/0217486 A1 | 8/2012 | Takemura. et al. |
| 2012/0217487 A1 | 8/2012 | Yamazaki et al. |
| 2012/0235127 A1 | 9/2012 | Takasu et al. |
| 2012/0248968 A1 | 10/2012 | Ogiwara et al. |
| 2012/0256535 A1 | 10/2012 | Seo et al. |
| 2012/0263648 A1 | 10/2012 | Shapiro et al. |
| 2013/0048964 A1 | 2/2013 | Takeda et al. |
| 2013/0049579 A1 | 2/2013 | Kaiser et al. |
| 2013/0056720 A1 | 3/2013 | Kim et al. |
| 2013/0270531 A1 | 10/2013 | Seo et al. |
| 2013/0277653 A1 | 10/2013 | Osaka et al. |
| 2013/0277655 A1 | 10/2013 | Seo et al. |
| 2013/0292656 A1 | 11/2013 | Seo et al. |
| 2013/0306945 A1 | 11/2013 | Seo |
| 2014/0014930 A1 | 1/2014 | Hirose et al. |
| 2014/0034925 A1 | 2/2014 | Osaka et al. |
| 2014/0034926 A1 | 2/2014 | Matsubara et al. |
| 2014/0034927 A1 | 2/2014 | Seo et al. |
| 2014/0034930 A1 | 2/2014 | Seo et al. |
| 2014/0034931 A1 | 2/2014 | Inoue et al. |
| 2014/0034932 A1 | 2/2014 | Seo et al. |
| 2014/0061604 A1 | 3/2014 | Seo et al. |
| 2014/0336379 A1 | 11/2014 | Adachi et al. |
| 2015/0053958 A1 | 2/2015 | Ishisone et al. |
| 2015/0069352 A1 | 3/2015 | Kim et al. |
| 2016/0028022 A1 | 1/2016 | Seo et al. |
| 2016/0056401 A1 | 2/2016 | Lee et al. |
| 2016/0064684 A1 | 3/2016 | Seo et al. |
| 2016/0093823 A1 | 3/2016 | Seo et al. |
| 2016/0104847 A1 | 4/2016 | Xia et al. |
| 2016/0104855 A1 | 4/2016 | Ohsawa et al. |
| 2016/0172601 A1 | 6/2016 | Kawamura et al. |
| 2016/0172602 A1 | 6/2016 | Ogiwara et al. |
| 2016/0190500 A1 | 6/2016 | Watabe. et al. |
| 2016/0248031 A1 | 8/2016 | Seo |
| 2016/0248032 A1 | 8/2016 | Seo et al. |
| 2016/0268513 A1 | 9/2016 | Ishisone et al. |
| 2016/0268534 A1 | 9/2016 | Hosoumi et al. |
| 2016/0301014 A1 | 10/2016 | Kawamura et al. |
| 2016/0343949 A1 | 11/2016 | Seo et al. |
| 2016/0343954 A1 | 11/2016 | Seo et al. |
| 2016/0351833 A1 | 12/2016 | Hosoumi et al. |
| 2017/0012207 A1 | 1/2017 | Seo et al. |
| 2017/0062731 A1 | 3/2017 | Ogiwara et al. |
| 2017/0271610 A1 | 9/2017 | Takahashi |
| 2017/0324054 A1 | 11/2017 | Ishisone et al. |
| 2017/0324055 A1 | 11/2017 | Ishisone. et al. |
| 2019/0280236 A1 | 9/2019 | Tabata et al. |
| 2020/0388781 A1 | 12/2020 | Tabata et al. |
| 2021/0043840 A1 | 2/2021 | Seo et al. |
| 2021/0057667 A1 | 2/2021 | Ohsawa et al. |
| 2021/0104680 A1 | 4/2021 | Ogiwara et al. |
| 2021/0280811 A1 | 9/2021 | Ohsawa et al. |
| 2021/0327968 A1 | 10/2021 | Ishisone et al. |

FOREIGN PATENT DOCUMENTS

| | | |
|---|---|---|
| CN | 105514288 A | 4/2016 |
| CN | 105556696 A | 5/2016 |
| CN | 106887532 A | 6/2017 |
| DE | 102010020044 | 11/2011 |

(56) References Cited

FOREIGN PATENT DOCUMENTS

| | | | |
|---|---|---|---|
| EP | 1202608 A | 5/2002 | |
| EP | 3188271 A | 7/2017 | |
| JP | 2686418 | 12/1997 | |
| JP | 2002-256168 A | 9/2002 | |
| JP | 2008-288344 A | 11/2008 | |
| JP | 2011-213643 A | 10/2011 | |
| JP | 2013-526773 | 6/2013 | |
| JP | 2014-045179 A | 3/2014 | |
| JP | 2016-027606 A | 2/2016 | |
| JP | 2019-054261 A | 4/2019 | |
| JP | 2020-017721 A | 1/2020 | |
| KR | 2013-0107206 A | 10/2013 | |
| KR | 2016-0043505 A | 4/2016 | |
| KR | 2016-0046806 A | 4/2016 | |
| KR | 2017-0083960 A | 7/2017 | |
| TW | 201513424 | 4/2015 | |
| TW | 201938526 | 10/2019 | |
| WO | WO-2011/141109 | 11/2011 | |
| WO | WO-2015/029808 | 3/2015 | |
| WO | WO-2015/198988 | 12/2015 | |
| WO | WO-2016/031785 | 3/2016 | |
| WO | WO-2018/097153 | 5/2018 | |
| WO | WO-2018/186462 | 10/2018 | |
| WO | WO-2019/171197 | 9/2019 | |
| WO | WO-2019/215535 | 11/2019 | |
| WO | WO-2020/012304 | 1/2020 | |

OTHER PUBLICATIONS

Jun-Yeob Lee, Journal of Information Display, vol. 15(3), 2014, 139-144.*

International Search Report (Application No. PCT/IB2020/053463) Dated Jun. 30, 2020.

Written Opinion (Application No. PCT/IB2020/053463) Dated Jun. 30, 2020.

Itano.K et al., "Exciplex formation at the organic solid-state interface: Yellow emission in organic light-emitting diodes using green-fluorescent tris(8-quinolinolato)aluminum and hole-transporting molecular materials with low ionization potentials", Appl. Phys. Lett. (Applied Physics Letters), Feb. 9, 1998, vol. 72, No. 6, pp. 636-638.

Endo.A et al., "Efficient Up-Conversion of Triplet Excitons Into a Singlet State and Its Application for Organic Light Emitting Diodes", Appl. Phys. Lett. (Applied Physics Letters), Feb. 24, 2011, vol. 98, No. 8, pp. 083302-1-083302-3.

Kondakova.M et al., "High-efficiency, low-voltage phosphorescent organic light-emitting diode devices with mixed host", J. Appl. Phys. (Journal of Applied Physics), Nov. 4, 2008, vol. 104, pp. 094501-1-094501-17.

Hino.Y et al., "Red Phosphorescent Organic Light-Emitting Diodes Using Mixture System of Small-Molecule and Polymer Host", Jpn. J. Appl. Phys. (Japanese Journal of Applied Physics), Apr. 21, 2005, vol. 44, No. 4B, pp. 2790-2794.

Su.S et al., "RGB Phosphorescent Organic Light-Emitting Diodes by Using Host Materials with Heterocyclic Cores:Effect of Nitrogen Atom Orientations", Chem. Mater. (Chemistry of Materials), 2011, vol. 23, No. 2, pp. 274-284.

Fujita.M et al., "Reduction of operating voltage in organic light-emitting diode by corrugated photonic crystal structure", Appl. Phys. Lett. (Applied Physics Letters), Dec. 6, 2004, vol. 85, No. 23, pp. 5769-5771.

Tsuboyama.A et al., "Homoleptic Cyclometalated Iridium Complexes with Highly Efficient Red Phosphorescence and Application to Organic Light-Emitting Diode", J. Am. Chem. Soc. (Journal of the American Chemical Society), 2003, vol. 125, No. 42, pp. 12971-12979.

Yoshida.K et al., "High efficiency reverse intersystem crossing of exciplex states", The 71st Autumn Meeting of the Japan Society of Applied Physics and Related Societies, 2010, p. 319, the Japan Society of Applied Physics.

Goushi.K et al., "Delayed fluorescence organic light-emitting diodes based on exciplex", The 59th Spring Meeting of the Japan Society of Applied Physics and Related Societies Preliminary Drafts, 2012, p. 251.

Nakagawa.T et al., "Electroluminescence based on thermally activated delayed fluorescence generated by a spirobifluorene donor-acceptor structure", Chemical Communications, Apr. 17, 2012, vol. 48, No. 77, pp. 9580-9582, RSC Publishing.

Yokoyama.D et al., "Dual efficiency enhancement by delayed fluorescence and dipole orientation in high-efficiency fluorescent organic light-emitting diodes", Appl. Phys. Lett. (Applied Physics Letters), Sep. 22, 2011, vol. 99, No. 12, pp. 1-4, AIP Publishing.

Mehes.G et al., "Thermally Activated Delayed Fluorescence and its Application for OLED". The 2nd Phoenics International Symposium, Mar. 5, 2012.

Sajoto.T et al., "Temperature Dependence of Blue Phosphorescent Cyclometalated Ir(III) Complexes", J. Am. Chem. Soc. (Journal of the American Chemical Society), Jun. 18, 2009, vol. 131, No. 28, pp. 9813-9822.

Gong.X et al., "Phosphorescence from iridium complexes doped into polymer blends", J. Appl. Phys. (Journal of Applied Physics), Feb. 1, 2004, vol. 95, No. 3, pp. 948-953.

Lee.J et al., "Stabilizing the efficiency of phosphorescent organic light-emitting diodes", SPIE Newsroom, Apr. 21, 2008, pp. 1-3.

D'Andrade.B et al., "High-efficiency yellow double-doped organic light-emitting devices based on phosphor-sensitized fluorescence", Appl. Phys. Lett. (Applied Physics Letters), Aug. 13, 2001, vol. 79, No. 7, pp. 1045-1047.

Cheng.G et al., "Improved efficiency for white organic light-emitting devices based on phosphor sensitized fluorescence", Appl. Phys. Lett. (Applied Physics Letters), Feb. 20, 2006, vol. 88, No. 8, pp. 083512-1-083512-3.

Kanno.H et al., "White organic light-emitting device based on a compound fluorescent phosphor-sensitized-fluorescent emission layer", Appl. Phys. Lett. (Applied Physics Letters). Oct. 2, 2006, vol. 89, No. 14, pp. 143516-1-143516-3.

Matsumoto.N et al., "Exciplex Formations between Tris(8-hydroxyquinolate)aluminum and Hole Transport Materials and Their Photoluminescence and Electroluminescence Characteristics", J. Phys. Chem. C (The Journal of Physical Chemistry C), May 22, 2008, vol. 112, No. 20, pp. 7735-7741.

Yersin.H et al., Highly Efficient OLEDs with Phosphorescent Materials, 2008, pp. 1-97,283-309, Wiley-VCH Verlag GmbH & Co.

Tokito.S et al., "Improvement in performance by doping", Organic EL Display, Aug. 20, 2004, pp. 67-99, Ohmsha.

Jeon.W et al., "Ideal host and guest system in phosphorescent OLEDs". Organic Electronics, 2009, vol. 10, pp. 240-246, Elsevier.

Rausch.A et al., "Matrix Effects on the Triplet State of the OLED Emitter Ir(4,6-dFppy)2(pic)(Firpic):Investigations by High-Resolution Optical Spectroscopy", Inorg. Chem. (Inorganic Chemistry), 2009, vol. 48, No. 5, pp. 1928-1937.

Zhao.Q et al., "Synthesis and Photophysical, Electrochemical, and Electrophosphorescent Properties of a Series of Iridium(III) Complexes Based on Quinoline Derivatives and Different β-Diketonate Ligands", Organometallics, Jun. 14, 2006, vol. 25, No. 15, pp. 3631-3638.

Park.Y et al., "Efficient triplet harvesting by fluorescent molecules through exciplexes for high efficiency organic light-emitting diodes", Appl. Phys. Lett. (Applied Physics Letters), Apr. 18, 2013, vol. 102, No. 15, pp. 153306-1-153306-5.

Nakanotani.H et al., "High-efficiency organic light-emitting diodes with fluorescent emitters", Nature Communications, May 30, 2014, vol. 5, pp. 4016-1-4016-7.

Noda.H et al., "Excited state engineering for efficient reverse intersystem crossing", Science Advances, Jul. 22, 2018, vol. 4, No. 6, p. 6910.

Baldo.M et al., "High-Efficiency Fluorescent Organic Light-Emitting Devices Using a Phosphorescent Sensitizer", Nature, Feb. 17, 2000, vol. 403, No. 6771, pp. 750-753.

Wang.S et al., "Highly Efficient Near-Infrared Delayed Fluorescence Organic Light Emitting Diodes Using a Phenanthrene-Based

(56) References Cited

OTHER PUBLICATIONS

Charge-Transfer Compound", Angew. Chem. Int. Ed. (Angewandte Chemie International Edition), Oct. 26, 2015, vol. 54, No. 44, pp. 13068-13072.

* cited by examiner

4000

4200

LIGHT-EMITTING DEVICE, LIGHT-EMITTING APPARATUS, ELECTRONIC DEVICE, AND LIGHTING DEVICE

CROSS REFERENCE TO RELATED APPLICATIONS

This application is a U.S. National Phase Application under 35 U.S.C. § 371 of International Application PCT/IB2020/053463, filed on Apr. 13, 2020, which is incorporated by reference and claims the benefit of a foreign priority application filed in Japan on Apr. 25, 2019, as Application No. 2019-084536.

TECHNICAL FIELD

One embodiment of the present invention relates to a light-emitting device, a light-emitting apparatus, an electronic device, and a lighting device. However, one embodiment of the present invention is not limited thereto. That is, one embodiment of the present invention relates to an object, a method, a manufacturing method, or a driving method. Alternatively, one embodiment of the present invention relates to a process, a machine, manufacture, or a composition of matter.

BACKGROUND ART

In recent years, research has been extensively conducted on light-emitting devices utilizing electroluminescence (EL). These light-emitting devices have a structure in which an EL layer (containing a light-emitting substance) is interposed between a pair of electrodes. In a light-emitting device, voltage application between a pair of electrodes causes, in an EL layer, recombination of electrons and holes injected from the electrodes, which brings a light-emitting substance (an organic compound) contained in the EL layer into an excited state; and light is emitted when the light-emitting substance returns to the ground state from the excited state. The excited state can be a singlet excited state (S*) and a triplet excited state (T*); and light emission from a singlet excited state is referred to as fluorescence, and light emission from a triplet excited state is referred to as phosphorescence. The statistical generation ratio thereof in the light-emitting device is considered to be S*:T*=1:3. Therefore, light-emitting devices using phosphorescent substances capable of converting the energy of the triplet excited state into light emission have been actively developed recently to obtain high efficiency.

As a material capable of converting part or all of the energy of the triplet excited state into light emission, a thermally activated delayed fluorescent (TADF) material is known in addition to a phosphorescent substance. In the TADF material, a singlet excited state can be generated from a triplet excited state by reverse intersystem crossing.

A method in which in a light-emitting device containing a TADF material and a fluorescent substance in combination, the singlet excitation energy of the TADF material is transferred to the fluorescent substance and light emission is efficiently obtained from the fluorescent substance has been proposed (see Patent Document 1 and Non-Patent Document 1).

REFERENCE

Patent Document

[Patent Document 1] Japanese Published Patent Application No. 2014-45179

Non-Patent Document

[Non-Patent Document 1] Hiroki Noda et al., "SCIENCE ADVANCES", 2018, vol. 4, no. 6, eaao6910

SUMMARY OF THE INVENTION

Problems to be Solved by the Invention

In order to efficiently utilize the energy of an excited state generated in an EL layer of a light-emitting device, preferably, the energy from a singlet excited state (S*) (hereinafter referred to as singlet excitation energy) of a host material is transferred to a fluorescent substance and the energy from a triplet excited state (T*) (hereinafter referred to as triplet excitation energy) of the host material is transferred to a phosphorescent substance or a TADF material.

However, in the case where a plurality of guest materials are used in an EL layer of a light-emitting device, the excitation energy of a host material is generally transferred to a material with a lower energy level; thus, when a fluorescent substance and a phosphorescent substance or a TADF material are used as guest materials, the singlet excitation energy and the triplet excitation energy of the host material are both transferred to a material with a lower energy level, which makes it difficult to concurrently obtain light emission from both the fluorescent substance and the phosphorescent substance or the TADF material. In addition, the triplet excitation level of the fluorescent substance does not contribute to light emission and serves as a deactivation pathway of the triplet excitation energy. Thus, efficient emission of both the fluorescent substance and the phosphorescent substance or the TADF material is achieved with difficulty.

In view of the above, an object of one embodiment of the present invention is that in an EL layer (particularly a light-emitting layer) of a light-emitting device, the singlet excitation energy of a host material is transferred to the S1 level of a fluorescent substance and the triplet excitation energy of the host material is transferred to the T1 level of a phosphorescent substance or a TADF material, whereby both the fluorescent substance and the phosphorescent substance or the TADF material emit light to improve the emission efficiency of the light-emitting device.

Thus, an object of one embodiment of the present invention is to provide a light-emitting device in which a plurality of kinds of light emission with different wavelengths (emission peak wavelengths) can be obtained from a light-emitting layer included in an EL layer. Another object of one embodiment of the present invention is to provide a light-emitting device with high emission efficiency. Another object of one embodiment of the present invention is to provide a novel light-emitting device. Another object of one embodiment of the present invention is to provide a novel light-emitting apparatus. Another object of one embodiment of the present invention is to provide a novel electronic device. Another object of one embodiment of the present invention is to provide a novel lighting device.

Note that the description of these objects does not preclude the existence of other objects. In one embodiment of the present invention, there is no need to achieve all of these objects. Objects other than these are apparent from the description of the specification, the drawings, the claims, and the like, and objects other than these can be derived from the description of the specification, the drawings, the claims, and the like.

Means for Solving the Problems

As described above, the development of a method for efficiently converting triplet excitation energy into light emission in a light-emitting device that emits fluorescence is required. Thus, it is necessary to improve energy transfer efficiency between materials used in a light-emitting layer. This needs inhibition of the transfer of triplet excitons by the Dexter mechanism between an energy donor and an energy acceptor.

One embodiment of the present invention is a light-emitting device including an EL layer between a pair of electrodes; the EL layer includes a light-emitting layer; the light-emitting layer includes a first organic compound having a function of converting singlet excitation energy into light emission and a second organic compound having a function of converting triplet excitation energy into light emission; the first organic compound includes a luminophore and five or more protecting groups; the luminophore is a condensed aromatic ring or a condensed heteroaromatic ring; the five or more protecting groups each have any one of an alkyl group having 1 to 10 carbon atoms, a substituted or unsubstituted cycloalkyl group having 3 to 10 carbon atoms, and a trialkylsilyl group having 3 to 12 carbon atoms; and the lowest singlet excitation energy level (S1 level) of the first organic compound is higher than the lowest triplet excitation energy level (T1 level) of the second organic compound.

Another embodiment of the present invention is a light-emitting device including an EL layer between a pair of electrodes; the EL layer includes a light-emitting layer; the light-emitting layer includes a first organic compound having a function of converting singlet excitation energy into light emission and a second organic compound having a function of converting triplet excitation energy into light emission; the first organic compound includes a luminophore and five or more protecting groups; the luminophore is a condensed aromatic ring or a condensed heteroaromatic ring; the five or more protecting groups each have any one of an alkyl group having 1 to 10 carbon atoms, a substituted or unsubstituted cycloalkyl group having 3 to 10 carbon atoms, and a trialkylsilyl group having 3 to 12 carbon atoms; and the peak wavelength of the emission spectrum of the second organic compound is longer than the peak wavelength of the emission spectrum of the first organic compound.

In each of the above structures, the light-emitting layer further includes a third organic compound; the lowest singlet excitation energy level (S1 level) of the third organic compound is higher than the lowest singlet excitation energy level (S1 level) of the first organic compound; and the lowest triplet excitation energy level (T1 level) of the third organic compound is higher than the lowest triplet excitation energy level (T1 level) of the second organic compound.

Another embodiment of the present invention is a light-emitting device including an EL layer between a pair of electrodes; the EL layer includes a light-emitting layer; the light-emitting layer includes a first organic compound having a function of converting singlet excitation energy into light emission, a second organic compound having a function of converting triplet excitation energy into light emission, a fourth organic compound, and a fifth organic compound; the first organic compound includes a luminophore and five or more protecting groups; the luminophore is a condensed aromatic ring or a condensed heteroaromatic ring; the five or more protecting groups each have any one of an alkyl group having 1 to 10 carbon atoms, a substituted or unsubstituted cycloalkyl group having 3 to 10 carbon atoms, and a trialkylsilyl group having 3 to 12 carbon atoms; the lowest singlet excitation energy level (S1 level) of the first organic compound is higher than the lowest triplet excitation energy level (T1 level) of the second organic compound; and the fourth organic compound and the fifth organic compound form an exciplex.

Another embodiment of the present invention is a light-emitting device including an EL layer between a pair of electrodes; the EL layer includes a light-emitting layer; the light-emitting layer includes a first organic compound having a function of converting singlet excitation energy into light emission, a second organic compound having a function of converting triplet excitation energy into light emission, a fourth organic compound, and a fifth organic compound; the first organic compound includes a luminophore and five or more protecting groups; the luminophore is a condensed aromatic ring or a condensed heteroaromatic ring; the five or more protecting groups each have any one of an alkyl group having 1 to 10 carbon atoms, a substituted or unsubstituted cycloalkyl group having 3 to 10 carbon atoms, and a trialkylsilyl group having 3 to 12 carbon atoms; the peak wavelength of the emission spectrum of the second organic compound is longer than the peak wavelength of the emission spectrum of the first organic compound; and the fourth organic compound and the fifth organic compound form an exciplex.

In each of the above structures, light emission can be obtained from both the first organic compound and the second organic compound.

In each of the above structures, the first organic compound has a plurality of diarylamino groups; the luminophore is bonded to the protecting groups through the diarylamino groups; and the plurality of protecting groups are bonded to each of the diarylamino groups.

In each of the above structures, each of the diarylamino groups is a diphenylamino group and each of the protecting groups is independently bonded to the 3-position or the 5-position of the diphenylamino group.

In each of the above structures, the alkyl group is a branched-chain alkyl group.

In each of the above structures, the condensed aromatic ring or the condensed heteroaromatic ring is any one of naphthalene, anthracene, fluorene, chrysene, triphenylene, tetracene, pyrene, perylene, coumarin, quinacridone, and naphthobisbenzofuran.

In each of the above structures, the first organic compound is represented by General Formula (G1) below.

[Chemical Formula 1]

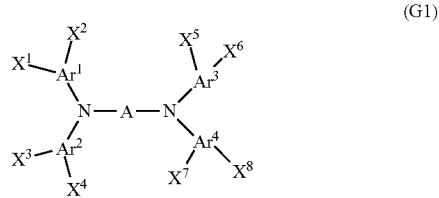

(G1)

In the formula, A represents a substituted or unsubstituted condensed aromatic ring having 10 to 30 carbon atoms or a substituted or unsubstituted condensed heteroaromatic ring having 10 to 30 carbon atoms, $Ar^1$ to $Ar^4$ each independently represent a substituted or unsubstituted aromatic hydrocarbon group having 6 to 13 carbon atoms, $X^1$ to $X^8$ each independently represent any one of an alkyl group having 1 to 10 carbon atoms, a substituted or unsubstituted cycloalkyl group having 3 to 10 carbon atoms, and a trialkylsilyl group having 3 to 10 carbon atoms.

In the above structures, the first organic compound is represented by General Formula (G2) below.

[Chemical Formula 2]

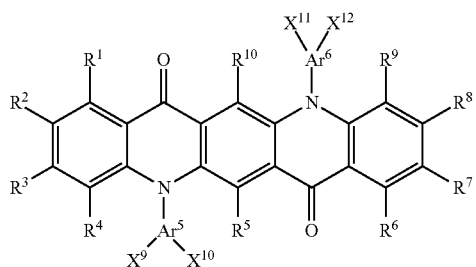

(G2)

In the formula, $Ar^5$ or $Ar^6$ each independently represent a substituted or unsubstituted aromatic hydrocarbon group having 6 to 13 carbon atoms, $X^9$ to $X^{12}$ each independently represent any one of an alkyl group having 1 to 10 carbon atoms, a substituted or unsubstituted cycloalkyl group having 3 to 10 carbon atoms, and a trialkylsilyl group having 3 to 10 carbon atoms, and $R^1$ to $R^{10}$ each independently represent any one of hydrogen, an alkyl group having 3 to 10 carbon atoms, a substituted or unsubstituted cycloalkyl group having 3 to 10 carbon atoms, and a trialkylsilyl group having 3 to 12 carbon atoms.

In each of the above structures, the first organic compound is represented by General Formula (G3) below.

[Chemical Formula 3]

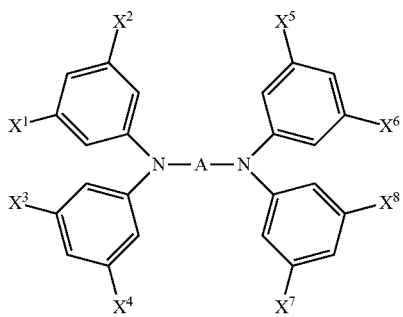

(G3)

In the formula, A represents a substituted or unsubstituted condensed aromatic ring having 10 to 30 carbon atoms or a substituted or unsubstituted condensed heteroaromatic ring having 10 to 30 carbon atoms, and $X^1$ to $X^8$ each independently represent any one of an alkyl group having 1 to 10 carbon atoms, a substituted or unsubstituted cycloalkyl group having 3 to 10 carbon atoms, and a trialkylsilyl group having 3 to 10 carbon atoms.

In the above structures, the first organic compound is represented by General Formula (G4) below.

[Chemical Formula 4]

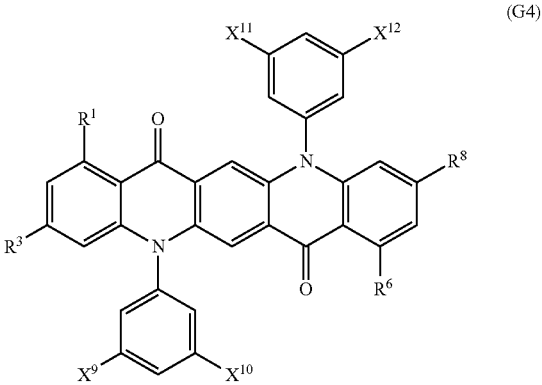

(G4)

In the formula, $X^9$ to $X^{12}$ each independently represent any one of an alkyl group having 1 to 10 carbon atoms, a substituted or unsubstituted cycloalkyl group having 3 to 10 carbon atoms, and a trialkylsilyl group having 3 to 10 carbon atoms. $R^1$, $R^3$, $R^6$, and $R^8$ each independently represent any one of hydrogen, an alkyl group having 3 to 10 carbon atoms, a substituted or unsubstituted cycloalkyl group having 3 to 10 carbon atoms, and a trialkylsilyl group having 3 to 12 carbon atoms.

In each of the above structures, the alkyl group is a branched-chain alkyl group.

One embodiment of the present invention includes in the scope of the invention a light-emitting apparatus including a transistor, a substrate, or the like in addition to the above-described light-emitting devices (also referred to as light-emitting elements). The scope of the invention also includes an electronic device and a lighting device that include a microphone, a camera, an operation button, an external connection portion, a housing, a cover, a support, a speaker, or the like in addition to the light-emitting apparatuses. That is, one embodiment of the present invention includes in the scope of the invention a light-emitting apparatus including a light-emitting device, and further includes an electronic device and a lighting device including the light-emitting apparatus. Accordingly, the light-emitting apparatus in this specification refers to an image display device or a light source (including a lighting device). In addition, the light-emitting apparatus includes a module in which a light-emitting apparatus is connected to a connector (e.g., an FPC (Flexible Printed Circuit) or a TCP (Tape Carrier Package), a module in which a printed wiring board is provided on the tip of a TCP, and a module in which an IC (integrated circuit) is directly mounted on a light-emitting device by a COG (Chip On Glass) method.

Effect of the Invention

According to one embodiment of the present invention, a light-emitting device with high emission efficiency can be provided. According to another embodiment of the present invention, a highly reliable light-emitting device can be provided. According to another embodiment of the present invention, a light-emitting device with reduced power consumption can be provided. According to another embodiment of the present invention, a novel light-emitting device can be provided. According to another embodiment of the present invention, a novel light-emitting apparatus can be provided. According to another embodiment of the present invention, a novel display device can be provided. A novel organic compound can also be provided.

Note that the description of these effects does not preclude the existence of other effects. In one embodiment of the present invention, there is no need to achieve all of these effects. Effects other than these are apparent from the description of the specification, drawings, claims, and the like and effects other than these can be derived from the description of the specification, drawings, claims, and the like.

MODE FOR CARRYING OUT THE INVENTION

Figure 1A:
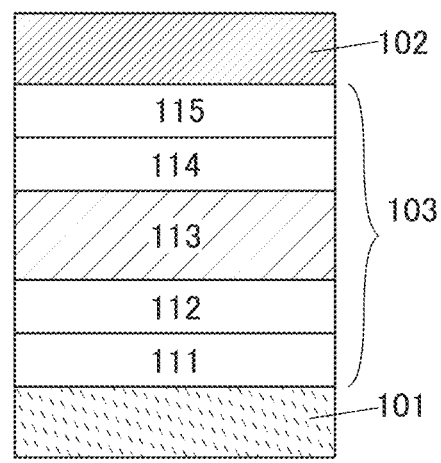
FIG. 1A is a diagram showing a structure of a light-emitting device.

Embodiments of the present invention will be described in detail below with reference to drawings. Note that the present invention is not limited to the following description, and the modes and details of the present invention can be modified in various ways without departing from the spirit and scope of the present invention. Thus, the present invention should not be construed as being limited to the descriptions in the following embodiments.

Note that the position, size, range, or the like of each component shown in drawings and the like is not accurately represented in some cases for easy understanding. Therefore, the disclosed invention is not necessarily limited to the position, size, range, or the like disclosed in drawings and the like.

Furthermore, when describing the structures of the invention with reference to the drawings in this specification and the like, the reference numerals denoting the same components are commonly used in different drawings.

In this specification and the like, a singlet excited state (S*) refers to a singlet state having excitation energy. An S1 level means the lowest level of the singlet excitation energy level, that is, the excitation energy level of the lowest singlet excited state (S1 state). A triplet excited state (T*) refers to a triplet state having excitation energy. A T1 level means the lowest level of the triplet excitation energy level, that is, the excitation energy level of the lowest triplet excited state (T1 state). Note that in this specification and the like, simple expressions singlet excited state and singlet excitation energy level mean the S1 state and the S1 level, respectively, in some cases. In addition, expressions triplet excited state and triplet excitation energy level mean the T1 state and the T1 level, respectively, in some cases.

In this specification and the like, a fluorescent substance refers to a compound that supplies light emission in the visible light region or the near-infrared region when the relaxation from the singlet excited state to the ground state occurs. A phosphorescent substance refers to a compound that supplies light emission in the visible light region or the near-infrared region at room temperature when the relaxation from the triplet excited state to the ground state occurs. In other words, a phosphorescent substance refers to one of compounds that can convert triplet excitation energy into light emission.

Embodiment 1

In this embodiment, a light-emitting device of one embodiment of the present invention will be described. As shown in FIG. 1A, the light-emitting device has a structure in which an EL layer 103 is positioned between a pair of electrodes, a first electrode 101 (corresponding to an anode in FIG. 1A) and a second electrode 102 (corresponding to a cathode in FIG. 1A); the EL layer 103 includes at least a light-emitting layer 113; and furthermore, functional layers such as a hole-injection layer 111, a hole-transport layer 112, an electron-transport layer 114, and an electron-injection layer 115 can be provided.

Figure 1B:
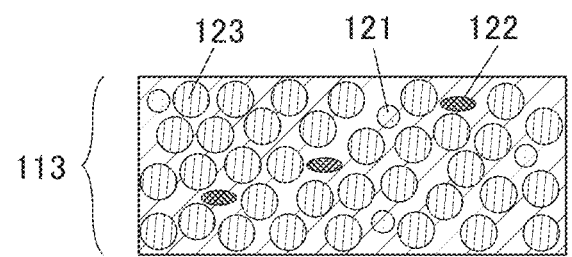
FIG. 1B is a diagram illustrating a light-emitting layer.

The light-emitting layer 113 is a layer including a light-emitting substance (a guest material) and preferably also includes a host material. Note that the light-emitting layer 113 in the light-emitting device of one embodiment of the present invention includes an organic compound functioning as a host material and a plurality of light-emitting substances (guest materials), and specifically includes, as shown in FIG. 1B, at least a first organic compound 121 that has a function of converting singlet excitation energy into light emission and a second organic compound 122 that has a function of converting triplet excitation energy into light emission. The light-emitting layer 113 also includes a third organic compound functioning as a host material. The light-emitting layer 113 may include a plurality of organic compounds each functioning as a host material.

Light emission from the light-emitting device is obtained in such a manner that carriers (holes and electrons) are recombined in the light-emitting layer 113 to generate a host material in an excited state (regardless of whether an exciplex is formed with a plurality of host materials), energy is transferred from the host material to a guest material, and the guest material emits light.

In the light-emitting device of one embodiment of the present invention, energy is transferred from the third organic compound 123 in an excited state, which functions as a host material, to the first organic compound (guest material, fluorescent substance) 121 having a function of converting singlet excitation energy into light emission, and to the second organic compound (guest material, phosphorescent substance) 122 having a function of converting triplet excitation energy into light emission, whereby fluorescence and phosphorescence can be obtained from the first organic compound 121 and the second organic compound 122, respectively. Note that a TADF material can be used as the second organic compound 122 instead of the phosphorescent substance, in which case the word phosphorescent substance and the word phosphorescence can be changed into the TADF material and the fluorescence, respectively.

Figure 2:
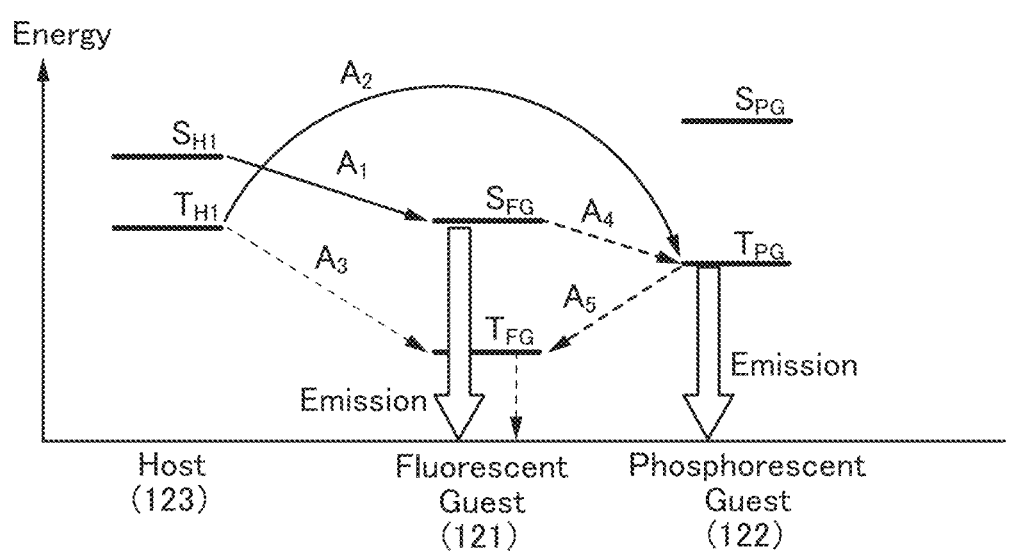
FIG. 2 is a conceptual diagram of energy transfer between a host material and a guest material in a light-emitting layer.

In order to achieve the structure in which, as in the light-emitting device of one embodiment of the present invention, both fluorescence from the first organic compound 121 as a guest material and phosphorescence from the second organic compound 122 as a guest material are obtained by energy transfer from the third organic compound 123 in an excited state that functions as a host material, as shown in FIG. 2, the lowest singlet excitation energy level (the S1 level) of the third organic compound 123 functioning as a host material needs to be higher than the S1 level of the first organic compound 121 that has a function of converting singlet excitation energy into light emission and energy should not be easily transferred from the T1 levels of the host material and the phosphorescent substance to the T1 level of the fluorescent substance.

FIG. 2 shows an example of the correlation between energy levels in the light-emitting layer 113 of the light-emitting device of one embodiment of the present invention. Although common reference numerals are used in FIG. 1B and FIG. 2, for convenience, the third organic compound 123 functioning as a host material is denoted as Host (123) in FIG. 2; the first organic compound 121 having a function of converting singlet excitation energy into light emission, Fluorescent Guest (121); and the second organic compound 122 having a function of converting triplet excitation energy into light emission, Phosphorescent Guest (122). The following explains what the other terms and numerals represent.

$S_{H1}$: S1 level of the third organic compound 123
$T_{H1}$: T1 level of the third organic compound 123
$S_{FG}$: S1 level of the first organic compound 121
$T_{FG}$: T1 level of the first organic compound 121
$S_{PG}$: T1 level of the second organic compound 122
$T_{PG}$: T1 level of the second organic compound 122

When the third organic compound 123 is brought into an excited state, the singlet excitation energy can be immediately transferred to the first organic compound 121 (Route $A_1$ in FIG. 2). At this time, $S_{H1} \geq S_{FG}$ is preferably satisfied. Specifically, when the level of energy with a wavelength of the line obtained by extrapolating a tangent to the fluorescent spectrum of the third organic compound 123 at a tail on the short wavelength side is $S_{H1}$ and the level of energy with a wavelength of the absorption edge of the absorption spectrum of the first organic compound 121 is $S_{FG}$, $S_{H1} \geq S_{FG}$ is preferably satisfied.

The second organic compound 122, which is a phosphorescent substance, can receive the singlet excitation energy and the triplet excitation energy of the third organic compound 123 (Route $A_2$ in FIG. 2). At this time, $T_{H1} \geq T_{PG}$ is preferably satisfied. Note that the level of energy with a wavelength of the absorption edge of the absorption spectrum of the second organic compound 122 can be regarded as $T_{PG}$. The level of energy with a wavelength of the emission edge of the emission spectrum of the third organic compound 123 on the short wavelength side at a low temperature (e.g., 10 K) can be regarded as $T_{H1}$. In order that emission from the first organic compound 121 and the second organic compound 122 can be obtained with a favorable ratio, $S_{FG} \geq T_{PG}$ is preferably satisfied.

In the light-emitting layer 113, the third organic compound 123, the first organic compound 121, and the second organic compound 122 are mixed. Hence, between the third organic compound 123 and the first organic compound 121, a process where the triplet excitation energy of the third organic compound 123 is converted into the triplet excitation energy of the first organic compound 121 (Route $A_3$ in FIG. 2) might occur in competition with Route $A_1$. The triplet excitation energy of the first organic compound 121 does not contribute to light emission because the first organic compound 121 is a fluorescent substance. That is, energy transfer through Route $A_3$ causes a decrease in the emission efficiency of the light-emitting device. Note that in practice, the energy transfer process $A_3$ from $T_{H1}$ to $T_{FG}$ can be, not a direct route, a pathway where $T_{H1}$ is once transferred to the triplet excited state at a level higher than $T_{FG}$ of the first organic compound 121 and then the triplet excited state is converted into $T_{FG}$ by internal conversion; the process is omitted in the drawing. Hereinafter, the same applies to all undesired thermal deactivation processes, that is, all the deactivation processes to $T_{FG}$ in this specification.

In the case where $S_{FG} \geq T_{PG}$ is satisfied as shown in FIG. 2, a process where the singlet excitation energy of the first organic compound 121 is converted into fluorescence is in competition with a process where the singlet excitation energy of the first organic compound 121 is transferred to $T_{PG}$ (Route $A_4$ in FIG. 2). That is, the second organic compound 122 receives excitation energy through Routes $A_2$ and $A_4$. Thus, in order that emission from the first organic compound 121 and the second organic compound 122 can be obtained with a favorable ratio, the concentration of the first organic compound 121 in the light-emitting layer 113 is preferably higher than that of the second organic compound 122. Furthermore, a lower concentration of the second organic compound 122 in the light-emitting layer 113 is preferable because carriers are less likely to be recombined in the second organic compound 122.

A process where the triplet excitation energy of the second organic compound 122 is converted into light emission might be in competition with a process where the triplet excitation energy of the second organic compound 122 is converted into the triplet excitation energy of the first organic compound 121 (Route $A_5$ in FIG. 2). The triplet excitation energy of the first organic compound 121 does not contribute to light emission because the first organic compound 121 is a fluorescent substance. That is, energy transfer through Route $A_5$ causes a decrease in the emission efficiency of the light-emitting device.

Note that a compound that emits light with a shorter emission wavelength is excited with higher energy. Thus, in order to achieve favorable reliability of the light-emitting device, a light-emitting substance with a high emission rate constant, that is, a fluorescent substance is preferably used as a compound that emits light with a short wavelength. In other words, the emission spectrum of the second organic compound 122 preferably has a longer peak wavelength than the emission spectrum of the first organic compound 121.

As mechanisms of the intermolecular energy transfer, the Förster mechanism (dipole-dipole interaction) and the Dexter mechanism (electron exchange interaction) are typically known.

Since the first organic compound 121, which is an energy acceptor, is a fluorescent substance, the Dexter mechanism is dominant as the mechanism of energy transfer through Route $A_3$ and Route $A_5$. In general, the Dexter mechanism occurs significantly when the distance between the third organic compound 123, which is an energy donor, and the first organic compound 121, which is an energy acceptor, is less than or equal to 1 nm. The Dexter mechanism also occurs significantly when the distance between the first organic compound 121 and the second organic compound 122 is less than or equal to 1 nm. Therefore, in order to inhibit Route $A_3$ and Route $A_5$, it is important that the distance between the energy donor and the energy acceptor be large.

Since direct transition from a singlet ground state to a triplet excited state in the first organic compound 121 is forbidden, energy transfer from the singlet excitation energy level ($S_{H1}$) of the third organic compound 123 to the triplet excitation energy level ($T_{FG}$) of the first organic compound 121 is unlikely to be a main energy transfer process; thus, the energy transfer is not illustrated.

In many cases, $T_{FG}$ in FIG. 2 is the energy level derived from a luminophore in the fluorescent substance, i.e., the first organic compound 121. Therefore, in order to inhibit energy transfer through Route $A_3$ and Route $A_5$, it is important that the third organic compound 123 and the second organic compound 122 each serving as the energy donor be made away from the luminophore of the first organic compound 121 serving as the energy acceptor, whereby the energy transfer by the Dexter mechanism is inhibited.

A general method for making the energy donor away from the luminophore of the first organic compound 121 serving as the energy acceptor is to lower the concentration of the first organic compound 121 in a mixed film of these organic compounds. However, lowering the concentration of the first organic compound 121 in the mixed film inhibits not only energy transfer based on the Dexter mechanism from the energy donor to the luminophore of the first organic compound 121 serving as the energy acceptor but also energy transfer based on the Förster mechanism. In that case, a problem such as a decrease in the emission efficiency and reliability of the light-emitting device is caused because Route $A_1$ is based on the Förster mechanism.

The present inventors have found that the above decrease in emission efficiency due to energy transfer can be inhibited by using, as the first organic compound 121 serving as the energy acceptor, a fluorescent substance having protecting groups for keeping a distance between the first organic compound 121 serving as the energy acceptor and the third organic compound 123 and the second organic compound 122 each serving as the energy donor. The present inventors also have found that the use of the first organic compound 121 having protecting groups allows light emission (fluorescence) derived from the first organic compound 121 and light emission (phosphorescence or fluorescence) derived from the second organic compound 122 to be obtained from the light-emitting layer 113 including the first organic compound 121 and the second organic compound 122.

Next, the concept of energy transfer between the host material and the guest material in the light-emitting layer of the light-emitting device of one embodiment of the present invention will be described with reference to FIG. 3A and FIG. 3B.

Figure 3A:
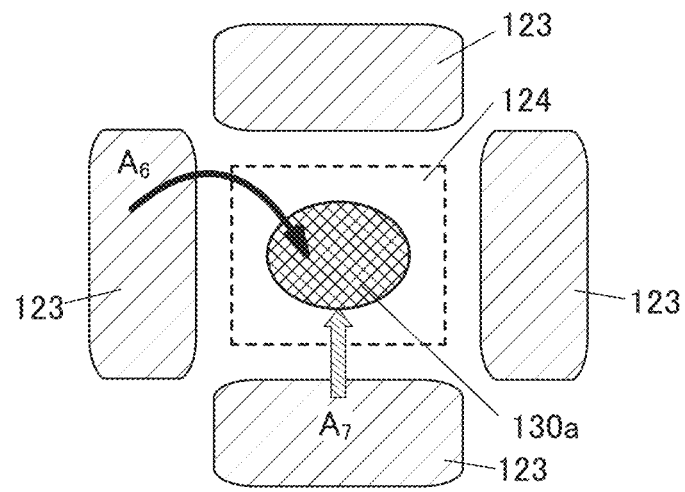
FIG. 3A is a conceptual diagram of energy transfer between typical guest material and host material.

FIG. 3A shows a state where the third organic compound 123 serving as a host material and a fluorescent substance 124 serving as a guest material are present. Note that the fluorescent substance 124 is a general fluorescent substance, and includes a luminophore 130a but does not include a protecting group.

Figure 3B:
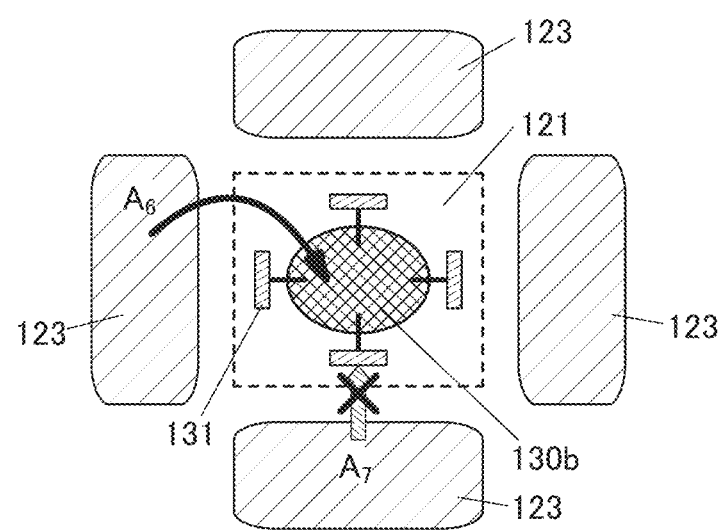
FIG. 3B is a conceptual diagram of energy transfer between a guest material and a host material used in a light-emitting layer.

FIG. 3B shows a state where the third organic compound 123 serving as a host material and the first organic compound (fluorescent substance) 121 serving as a guest material are present. Note that the first organic compound 121 is a fluorescent substance which is used as an energy acceptor in the light-emitting device of one embodiment of the present invention, and includes a luminophore 130b and a protecting group 131. Note that the protecting group 131 has a function of making the luminophore 130b away from the third organic compound (host material) 123 at such a distance that energy transfer from the third organic compound (host material) 123 to the luminophore 130b by the Dexter mechanism is less likely to occur.

As shown in FIG. 3A and FIG. 3B, the third organic compound 123 serving as a host material is positioned close to the fluorescent substance 124 or the first organic compound (fluorescent substance) 121 serving as a guest material. In the case where the fluorescent substance 124 does not include a protecting group as shown in FIG. 3A, the luminophore 130a and the third organic compound 123 are close to each other; thus, both energy transfer by the Forster mechanism (Route $A_6$ in FIG. 3A) and energy transfer by the Dexter mechanism (Route $A_7$ in FIG. 3A) can occur as the energy transfer from the third organic compound 123 to the fluorescent substance 124. In the case where the guest material is a fluorescent substance, when the triplet excitation energy transfer from the host material to the guest material is caused by the Dexter mechanism and the triplet exited state of the guest material is generated, non-radiative deactivation of the triplet excitation energy occurs, contributing to a reduction in the emission efficiency of the light-emitting device.

In FIG. 3B, the first organic compound (fluorescent substance) 121 serving as a guest material has the protecting group 131, allowing the luminophore 130b and the third organic compound 123 serving as a host material to be kept away from each other. This inhibits energy transfer by the Dexter mechanism (Route $A_7$). Therefore, when the first organic compound (fluorescent substance) 121 having the protecting group 131 is used as a guest material in the light-emitting layer of the light-emitting device of one embodiment of the present invention, energy transfer from the host material (the third organic compound 123) to the first organic compound 121 in the light-emitting layer (Route $A_3$ in FIG. 2) can be inhibited. The same applies to another guest material in the light-emitting layer (the second organic compound 122 described in FIG. 2): energy transfer from the second organic compound 122 to the first organic compound 121 (Route $A_3$ in FIG. 2) can be inhibited.

Here, the luminophore 130a included in the fluorescent substance 124 shown in FIG. 3A and the luminophore 130b included in the first organic compound (fluorescent substance) 121 shown in FIG. 3B are described. The luminophore (130a or 130b) refers to an atomic group (skeleton) that causes light emission in a fluorescent substance. The luminophore (130a or 130b) generally has a π bond and preferably has an aromatic ring, further preferably a condensed aromatic ring or a condensed heteroaromatic ring. As another embodiment, the luminophore (130a or 130b) can be regarded as an atomic group (skeleton) having an aromatic ring having a transition dipole vector on a ring plane. In the case where one fluorescent substance has a plurality of condensed aromatic rings or condensed heteroaromatic rings, a skeleton having the lowest S1 level among the plurality of condensed aromatic rings or condensed heteroaromatic rings is considered as a luminophore of the fluorescent substance in some cases. In other cases, a skeleton having an absorption edge on the longest wavelength side among the plurality of condensed rings or condensed heteroaromatic rings is considered as the luminophore of the fluorescent substance. The luminophore of the fluorescent substance can be presumed from the shapes of the emission spectra of the plurality of condensed rings or condensed heteroaromatic rings in some cases.

As the condensed aromatic ring or the condensed heteroaromatic ring, a phenanthrene skeleton, a stilbene skeleton, an acridone skeleton, a phenoxazine skeleton, a phenothiazine skeleton, and the like are given. Specifically, fluorescent substances having a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton are preferable because of their high fluorescence quantum yields.

The protecting group 131 in the first organic compound (fluorescent substance) 121 shown in FIG. 3B preferably has a T1 level higher than the T1 levels of the luminophore 130b and the third organic compound 123 serving as a host material. Thus, a saturated hydrocarbon group can be favorably used as the protecting group. Since the saturated hydrocarbon group has no π bond, it has a high T1 level and a poor function of transporting carriers (electrons or holes). Thus, including a saturated hydrocarbon group as the protecting group 131 in the first organic compound 121 can make the luminophore 130b and the third organic compound 123 serving as a host material away from each other with little influence on the excited state or the carrier-transport property of the third organic compound 123 serving as a host material.

In the case where the first organic compound (fluorescent substance) 121 includes both a substituent having no π bond and a substituent having a π-conjugated system, frontier orbitals {HOMO (Highest Occupied Molecular Orbital) and LUMO (Lowest Unoccupied Molecular Orbital)} are present on the substituent having a π-conjugated system in many cases; in particular, the luminophore 130b tends to have the frontier orbitals. As described later, the overlap of the HOMOs of the energy donor and the energy acceptor and the overlap of the LUMOs of the energy donor and the energy acceptor are important for energy transfer by the Dexter mechanism. Therefore, the use of a saturated hydrocarbon group as the protecting group enables a large distance between the frontier orbitals of the third organic compound 123 serving as an energy donor and the frontier orbitals of the first organic compound 121 serving as an energy acceptor, leading to inhibition of energy transfer by the Dexter mechanism.

A specific example of the protecting group 131 is an alkyl group having 1 to 10 carbon atoms. In addition, the protecting group 131 preferably has a bulky structure because the luminophore 130b of the first organic compound 121 serving as a guest material and the third organic compound 123 serving as a host material need to be away from each other. Thus, an alkyl group having 3 to 10 carbon atoms, a substituted or unsubstituted cycloalkyl group having 3 to 10 carbon atoms, or a trialkylsilyl group having 3 to 10 carbon atoms can be favorably used. In particular, the alkyl group is preferably a bulky branched-chain alkyl group. Furthermore, the substituent preferably has quaternary carbon, in which case it becomes a bulky substituent.

One luminophore 130b preferably has five or more protecting groups 131. With such a structure, the luminophore 130b can be entirely covered with the protecting groups 131, so that the distance between the third organic compound 123 and the luminophore can be adjusted as appropriate. The protecting groups 131 are preferably not directly bonded to the luminophore 130b. For example, the protecting groups 131 may each be bonded to the luminophore 130b via a substituent with a valence of 2 or more, such as an arylene group or an amino group. Bonding of each of the protecting groups 131 to the luminophore 130b via the substituent can effectively make the luminophore 130b away from the third organic compound 123. Thus, in the case where the protecting groups 131 are bonded to the luminophore 130b via the substituent, four or more protecting groups are preferably bonded to one luminophore in order to effectively inhibit the Dexter mechanism.

Furthermore, the substituent with a valence of 2 or more that bonds the luminophore 130b and each of the protecting groups 131 is preferably a substituent having a π-conjugated system. With such a structure, the physical properties of the first organic compound 121 serving as a guest material, such as the emission color, the HOMO level, and the glass transition point, can be adjusted. Note that the protecting groups 131 are preferably positioned on the outermost side when the molecular structure is observed with the luminophore positioned at the center.

As described above, energy transfer by the Dexter mechanism is inhibited in the first organic compound 121; thus, the first organic compound 121 needs to receive energy from the third organic compound 123 by the Førster mechanism in order to emit light. In other words, it is preferable that energy transfer by the Forster mechanism be efficiently utilized while energy transfer by the Dexter mechanism is inhibited. It is known that energy transfer by the Forster mechanism is also affected by the distance between a host material and a guest material. In general, the Dexter mechanism is dominant when the distance between the host material and the guest material is less than or equal to 1 nm, and the Førster mechanism is dominant when the distance therebetween is greater than or equal to 1 nm and less than or equal to 10 nm. Energy transfer is generally unlikely to occur when the distance between the host material and the guest material is greater than or equal to 10 nm.

Note that in this specification, the distance between the third organic compound 123 serving as a host material and the first organic compound 121 serving as a guest material is assumed to be equal to the distance between the third organic compound 123 and the luminophore 130b included in the first organic compound 121. Thus, in order that the Førster mechanism can be dominant, the protecting groups 131 of the first organic compound 121 preferably extend within a range from 1 nm to 10 nm from the luminophore 130b included in the first organic compound 121. Further preferably, the protecting groups 131 of the first organic compound 121 extend within a range from 1 nm to 5 nm. With such a structure, energy transfer by the Førster mechanism can be efficiently performed while energy transfer by the Dexter mechanism from the third organic compound 123 serving as a host material to the first organic compound 121 is inhibited. Thus, a light-emitting device with high emission efficiency can be fabricated.

In general, the concentration ratio of a fluorescent substance as a guest material to a host material is preferably increased in order to improve the efficiency of energy transfer (increase the energy transfer rate) by the Førster mechanism; however, the increased concentration ratio of the guest material increases the energy transfer rate by the Dexter mechanism, resulting in a decrease in emission efficiency, i.e., a trade-off relation exists. Therefore, increasing the concentration ratio of the guest material has not been an effective means for improving the emission efficiency.

In contrast, the first organic compound 121 used in the light-emitting device of one embodiment of the present invention has a structure capable of inhibiting energy transfer by the Dexter mechanism from a host material; thus, using the compound as a guest material in a light-emitting layer and increasing the concentration ratio of the compound to the host material can improve the energy transfer efficiency (increase the energy transfer rate) by the Førster mechanism. Note that when the energy transfer rate by the Forster mechanism is increased by increasing the concentration ratio to the host material, the excitation lifetime of the guest material (energy acceptor) in the light-emitting layer can be shortened, improving the reliability of the light-emitting device.

Note that in the light-emitting layer of the light-emitting device of one embodiment of the present invention, the concentration of the first organic compound 121 as the guest material to the third organic compound 123 as the host material is preferably higher than or equal to 2 wt % and lower than or equal to 30 wt %, further preferably higher than or equal to 5 wt % and lower than or equal to 20 wt %, and still further preferably higher than or equal to 5 wt % and lower than or equal to 15 wt %. With such a structure, the energy transfer rate by the Førster mechanism can be increased; thus, a light-emitting device with high emission efficiency can be obtained. The light-emitting layer of the light-emitting device of one embodiment of the present invention includes, in addition to the above structure, the second organic compound 122 having a function of converting triplet excitation energy into light emission as a guest material. Thus, in the light-emitting device of one embodiment of the present invention, fluorescence from the first organic compound 121 and emission (phosphorescence or fluorescence) from the second organic compound 122 can be obtained with high emission efficiency. In that case, the concentration of the first organic compound 121 is preferably higher than that of the second organic compound 122 in the light-emitting layer 113 in order that emission from both the first organic compound 121 and the second organic compound 122 can be obtained with a favorable ratio.

In the light-emitting device, the energy transfer described above always conflicts with a quenching process due to the influence of a degraded material and an impurity. That is, as the quenching rate constant of the quenching process increases over time, the proportion of light emission from the light-emitting device decreases, so that the luminance of the light-emitting device deteriorates. However, as described above, in the light-emitting device of one embodiment of the present invention, the energy transfer rate by the Førster mechanism can be more increased than in a conventional light-emitting device while the energy transfer by the Dexter mechanism is inhibited; thus, the influence of conflict with the quenching process can be reduced, so that the lifetime of the light-emitting device can be increased.

Here, the Førster mechanism and the Dexter mechanism will be described. As to supply of excitation energy from a first organic compound in an excited state to a second organic compound in a ground state, an intermolecular energy transfer process between the first organic compound and the second organic compound will be described here; the same can be applied to the case where one of them is an exciplex.

<<Førster Mechanism>>

In the Førster mechanism, energy transfer does not require direct intermolecular contact and energy is transferred through a resonant phenomenon of dipolar oscillation between a third organic compound and the first organic compound. By the resonant phenomenon of dipolar oscillation, the third organic compound provides energy to the first organic compound, and thus, the third organic compound in an excited state is brought into a ground state and the first organic compound in a ground state is brought into an excited state. Note that the rate constant $k_{h^*\to g}$ of the Førster mechanism is expressed by Equation (1).

[Equation 1]

$$k_{h^*\to g} = \frac{9000c^4 K^2 \phi \ln 10}{128\pi^5 n^4 N\tau R^6} \int \frac{f'_h(v)\varepsilon_g(v)}{v^4} dv \quad (1)$$

In Equation (1), v denotes a frequency; $f'_h(v)$, a normalized emission spectrum of the third organic compound (a fluorescent spectrum in the case where energy transfer from a singlet excited state is discussed, or a phosphorescent spectrum in the case where energy transfer from a triplet excited state is discussed); $\varepsilon_g(v)$, a molar absorption coefficient spectrum of the first organic compound; N, Avogadro's number; n, a refractive index of a medium; R, an intermolecular distance between the third organic compound and the first organic compound; τ, a measured lifetime of an excited state (fluorescence lifetime or phosphorescence lifetime); c, the speed of light; φ, a luminescence quantum yield (a fluorescence quantum yield in the case where energy transfer from a singlet excited state is discussed, or a phosphorescence quantum yield in the case where energy transfer from a triplet excited state is discussed); and $K^2$, a coefficient (0 to 4) of orientation of a transition dipole moment between the third organic compound and the first organic compound. Note that $K^2=2/3$ in random orientation.

In the case where the third organic compound is used as the energy donor and the first organic compound is used as the energy acceptor and the emission colors of the third organic compound and the first organic compound are close to each other, the overlap between $f'_h(v)$ and $\varepsilon_g(v)$ decreases according to Equation (1) above ($\varepsilon_g(v)$ exists on the longer wavelength side than the emission spectrum of the first organic compound); thus, $k_{h^*\to g}$ decreases according to Equation (1). However, in the light-emitting device of one embodiment of the present invention, the energy donor concentration in the light-emitting layer can be increased as mentioned above, so that the value of R in Equation (1) can be increased, which inhibits a decrease in $k_{h^*\to g}$. Thus, a fluorescent substance having an emission color close to that of the energy donor can be used as a light-emitting material in the light-emitting device of one embodiment of the present invention. Note that the light-emitting device of one embodiment of the present invention can also use an energy donor and an energy acceptor that have different emission colors.

<<Dexter Mechanism>>

In the Dexter mechanism, the third organic compound and the first organic compound are close to a contact effective range where their orbitals overlap, and the third organic compound in an excited state and the first organic compound in a ground state exchange their electrons, which leads to energy transfer. Note that the rate constant $k_{h^*\to g}$ of the Dexter mechanism is expressed by Equation (2)

[Equation 2]

$$k_{h^*\to g} = \left(\frac{2\pi}{h}\right)K^2 \exp\left(-\frac{2R}{L}\right)\int f'_h(v)\varepsilon'_g(v)dv \quad (2)$$

In Equation (2), h denotes a Planck constant and K denotes a constant having an energy dimension. In addition, v denotes a frequency. $f'_h(v)$ denotes a normalized emission spectrum of the third organic compound (the fluorescent spectrum in the case where energy transfer from a singlet excited state is discussed, or the phosphorescent spectrum in the case where energy transfer from a triplet excited state is discussed). $\varepsilon'_g(v)$ denotes a normalized absorption spectrum of the first organic compound. L denotes an effective molecular radius. R denotes an intermolecular distance between the third organic compound and the first organic compound.

Here, the efficiency of energy transfer $\phi_{ET}$ from the third organic compound to the first organic compound is expressed by Equation (3). Note that $k_r$ denotes a rate constant of a light-emission process (fluorescence in the case where energy transfer from a singlet excited state is discussed, or phosphorescence in the case where energy transfer from a triplet excited state is discussed) of the third organic compound; and $k_n$ denotes a rate constant of a non-light-emission process (thermal deactivation or intersystem crossing) of the first organic compound. In addition, r denotes a measured lifetime of an excited state of the third organic compound.

[Equation 3]

$$\phi_{ET} = \frac{k_{h^*\to g}}{k_r + k_n + k_{h^*\to g}} = \frac{k_{h^*\to g}}{\left(\frac{1}{\tau}\right) + k_{h^*\to g}} \quad (3)$$

According to Equation (3), it is found that the energy transfer efficiency $\phi_{ET}$ can be increased by increasing the rate constant $k_{h^*\to g}$ of energy transfer so that another competing rate constant $k_r+k_n$ (=1/τ) becomes relatively small.

Described next is a concept for increasing the energy transfer efficiency in the above energy transfer mechanism (the Førster mechanism and the Dexter mechanism).

First, energy transfer by the Førster mechanism is considered. When Equation (1) is substituted into Equation (3), r can be eliminated. This indicates that in the case of the Førster mechanism, the energy transfer efficiency $\phi_{ET}$ does not depend on the lifetime r of the excited state of the third organic compound. Furthermore, it can be said that high energy transfer efficiency $\phi_{ET}$ is obtained when the emission quantum yield φ is high.

Furthermore, it is preferable that the emission spectrum of the third organic compound largely overlap with the absorption spectrum of the first organic compound (absorption corresponding to transition from a singlet ground state to a singlet excited state). Moreover, it is preferable that the molar absorption coefficient of the first organic compound be also high. This means that the emission spectrum of the third organic compound overlaps with the absorption band of the first organic compound which is on the longest wavelength side. Note that since direct transition from the singlet ground state to the triplet excited state of the first organic compound is forbidden, the molar absorption coefficient of the first organic compound in the triplet excited state can be ignored. Thus, a process of energy transfer from an excited state of the third organic compound to a triplet excited state of the first organic compound by the Förster mechanism can be ignored, and only a process of energy transfer to a singlet excited state of the first organic compound is considered.

The rate of energy transfer by the Forster mechanism is inversely proportional to the 6th power of the intermolecular distance R between the third organic compound and the first organic compound, according to Equation (1). As described above, when R is less than or equal to 1 nm, energy transfer by the Dexter mechanism is dominant. Therefore, to increase the rate of energy transfer by the Förster mechanism while inhibiting energy transfer by the Dexter mechanism, the intermolecular distance is preferably greater than or equal to 1 nm and less than or equal to 10 nm. This requires the above protecting groups to be not too bulky; thus, the number of carbon atoms of the protecting groups is preferably 3 to 10.

Next, energy transfer by the Dexter mechanism is considered. According to Equation (2), in order to increase the rate constant $k_{h^* \to g}$, it is preferable that the emission spectrum of the third organic compound (the fluorescent spectrum in the case where energy transfer from a singlet excited state is discussed, or the phosphorescent spectrum in the case where energy transfer from a triplet excited state is discussed) largely overlap with an absorption spectrum of the first organic compound (absorption corresponding to transition from a singlet ground state to a singlet excited state). Therefore, the energy transfer efficiency can be optimized by making the emission spectrum of the third organic compound overlap with the absorption band of the first organic compound which is on the longest wavelength side.

When Equation (2) is substituted into Equation (3), it is found that the energy transfer efficiency $\phi_{ET}$ in the Dexter mechanism depends on τ. In the Dexter mechanism, which is a process of energy transfer based on the electron exchange, as well as the energy transfer from the singlet excited state of the third organic compound to the singlet excited state of the first organic compound, energy transfer from the triplet excited state of the third organic compound to the triplet excited state of the first organic compound occurs.

In the light-emitting device of one embodiment of the present invention in which the first organic compound is a fluorescent substance, the efficiency of energy transfer to the triplet excited state of the first organic compound is preferably low. That is, the efficiency of energy transfer based on the Dexter mechanism from the third organic compound to the first organic compound is preferably low and the efficiency of energy transfer based on the Förster mechanism from the third organic compound to the first organic compound is preferably high.

As described above, the energy transfer efficiency in the Förster mechanism does not depend on the lifetime r of the third organic compound in the excited state. In contrast, the energy transfer efficiency in the Dexter mechanism depends on the excitation lifetime r of the third organic compound; to reduce the energy transfer efficiency in the Dexter mechanism, the excitation lifetime r of the third organic compound is preferably short.

In the light-emitting device of one embodiment of the present invention, a fluorescent substance having protecting groups is used as the first organic compound. This can increase the intermolecular distance between the third organic compound and the first organic compound and inhibit energy transfer by the Dexter mechanism, thereby inhibiting the triplet excitation energy of the third organic compound from being transferred to the first organic compound by the Dexter mechanism and being deactivated. Thus, a light-emitting device with high emission efficiency can be provided.

Embodiment 2

A light-emitting layer of a light-emitting device of one embodiment of the present invention includes a host material and a guest material; and as the guest material, the first organic compound 121, which is a material (a fluorescent substance) having a function of converting singlet excitation energy into light emission, and the second organic compound 122, which is a material (a phosphorescent substance or a TADF material) having a function of converting triplet excitation energy into light emission, are used. In this embodiment, the first organic compound 121 is specifically described in detail.

The first organic compound 121, which is a material (a fluorescent substance) having a function of converting singlet excitation energy into light emission, includes the luminophore 130b and the protecting group 131. Note that a condensed aromatic ring or a condensed heteroaromatic ring can be used as the luminophore 130b.

The protecting group 131 included in the first organic compound 121 is preferably an alkyl group having 1 to 10 carbon atoms, a cycloalkyl group having 3 to 10 carbon atoms, a branched-chain alkyl group having 3 to 10 carbon atoms, or a trialkylsilyl group having 3 to 12 carbon atoms. When the first organic compound 121 includes the protecting group 131, energy transfer from a host material to the first organic compound 121 serving as a guest material by the Dexter mechanism can be inhibited in the light-emitting layer.

In the first organic compound 121, it is preferable that the luminophore 130b be bonded to two or more diarylamino groups having aryl groups, and each of the aryl groups have at least two protecting groups 131. When the two or more diarylamino groups are bonded to the luminophore 130b at symmetric positions, the quantum yield of the first organic compound 121 can be increased. A diphenylamino group is preferable as a specific example of the diarylamino group included in the first organic compound 121. The use of the diphenylamino group inhibits an increase in the molecular weight of the first organic compound 121, allowing maintaining the sublimability.

The aforementioned structure in which the diarylamino groups are bonded to the protecting groups 131 via the aryl groups is preferable because the protecting groups 131 can be arranged to cover the luminophore 130b, allowing the host material and the luminophore 130b to be away from each other from any direction. Note that the first organic compound 121 preferably has a structure in which one luminophore 130b includes four or more protecting groups 131.

In the case where diphenylamino groups are used as specific examples of the diarylamino groups included in the first organic compound 121, the protecting groups 131 are preferably positioned at the 3-position and the 5-position of the phenyl groups in the diphenylamino groups. In that case, the protecting groups 131 cover above and below the luminophore 130b included in the first organic compound 121 in the plane direction, so that energy transfer from the host material to the luminophore 130b by the Dexter mechanism can be inhibited.

One embodiment of the aforementioned first organic compound 121 is represented by General Formula (G1) below.

[Chemical Formula 5]

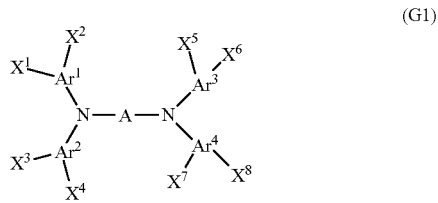

(G1)

In General Formula (G1) above, A represents a substituted or unsubstituted condensed aromatic ring having 10 to 30 carbon atoms or a substituted or unsubstituted condensed heteroaromatic ring having 10 to 30 carbon atoms, $Ar^1$ to $Ar^5$ each independently represent a substituted or unsubstituted aromatic hydrocarbon group having 6 to 13 carbon atoms, $X^1$ to $X^8$ each independently represent any one of an alkyl group having 1 to 10 carbon atoms, a substituted or unsubstituted cycloalkyl group having 3 to 10 carbon atoms, and a trialkylsilyl group having 3 to 10 carbon atoms.

Another embodiment of the aforementioned first organic compound 121 is represented by General Formula (G2) below.

[Chemical Formula 6]

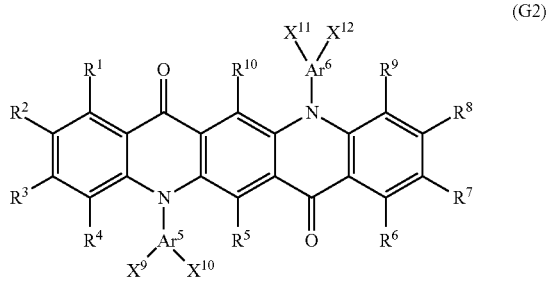

(G2)

In General Formula (G2) above, $Ar^5$ or $Ar^6$ each independently represent a substituted or unsubstituted aromatic hydrocarbon group having 6 to 13 carbon atoms, $X^9$ to $X^{12}$ each independently represent any one of an alkyl group having 1 to 10 carbon atoms, a substituted or unsubstituted cycloalkyl group having 3 to 10 carbon atoms, and a trialkylsilyl group having 3 to 10 carbon atoms, and $R^1$ to $R^{10}$ each independently represent any one of hydrogen, an alkyl group having 3 to 10 carbon atoms, a substituted or unsubstituted cycloalkyl group having 3 to 10 carbon atoms, and a trialkylsilyl group having 3 to 12 carbon atoms.

Note that the first organic compound 121 shown in General Formula (G2) has a structure in which the protecting groups 131 represented by $X^9$ to $X^{12}$ are bonded to a quinacridone skeleton, which is the luminophore 130b, via aromatic hydrocarbon groups represented by $Ar^5$ or $Ar^6$. With this structure, the protecting groups 131 can be arranged to cover the luminophore 130b; thus, energy transfer by the Dexter mechanism can be inhibited. Note that any of the protecting groups 131 may be directly bonded to the luminophore 130b.

Another embodiment of the aforementioned first organic compound 121 is represented by General Formula (G3) below.

[Chemical Formula 7]

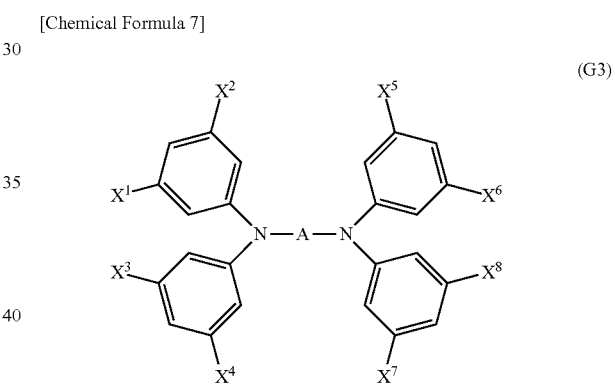

(G3)

In General Formula (G3) above, A represents a substituted or unsubstituted condensed aromatic ring having 10 to 30 carbon atoms or a substituted or unsubstituted condensed heteroaromatic ring having 10 to 30 carbon atoms, and $X^1$ to $X^8$ each independently represent any one of an alkyl group having 1 to 10 carbon atoms, a substituted or unsubstituted cycloalkyl group having 3 to 10 carbon atoms, and a trialkylsilyl group having 3 to 10 carbon atoms.

Note that the first organic compound 121 shown in General Formula (G3) has a structure in which the protecting groups 131 represented by $X^1$ to $X^8$ are bonded to the luminophore 130b represented by A via a phenylene group. The two protecting groups 131 bonded to one phenylene group are preferably bonded at the meta-position of the phenylene group. With this structure, the protecting groups 131 can be arranged to cover the luminophore 130b; thus, energy transfer by the Dexter mechanism can be inhibited. Note that any of the protecting groups 131 may be directly bonded to the luminophore 130b.

Another embodiment of the aforementioned first organic compound 121 is represented by General Formula (G4) below.

[Chemical Formula 8]

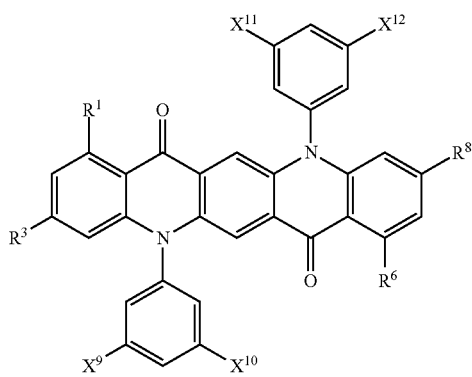

(G4)

In General Formula (G4) above, $X^9$ to $X^{12}$ each independently represent any one of an alkyl group having 1 to 10 carbon atoms, a substituted or unsubstituted cycloalkyl group having 3 to 10 carbon atoms, and a trialkylsilyl group having 3 to 10 carbon atoms. $R^1$, $R^3$, $R^6$, and $R^8$ each independently represent any one of hydrogen, an alkyl group having 3 to 10 carbon atoms, a substituted or unsubstituted cycloalkyl group having 3 to 10 carbon atoms, and a trialkylsilyl group having 3 to 12 carbon atoms.

Note that the first organic compound 121 shown in General Formula (G4) has a structure in which the protecting groups 131 represented by $X^9$ to $X^{12}$ are bonded to a quinacridone skeleton, which is the luminophore 130b, via a phenylene group. The two protecting groups 131 bonded to one phenylene group are preferably bonded at the meta-position of the phenylene group. With this structure, the protecting groups 131 can be arranged to cover the luminophore 130b; thus, energy transfer by the Dexter mechanism can be inhibited. Note that any of the protecting groups 131 may be directly bonded to the luminophore 130b.

Another embodiment of the aforementioned first organic compound 121 is represented by General Formula (G5) below.

[Chemical Formula 9]

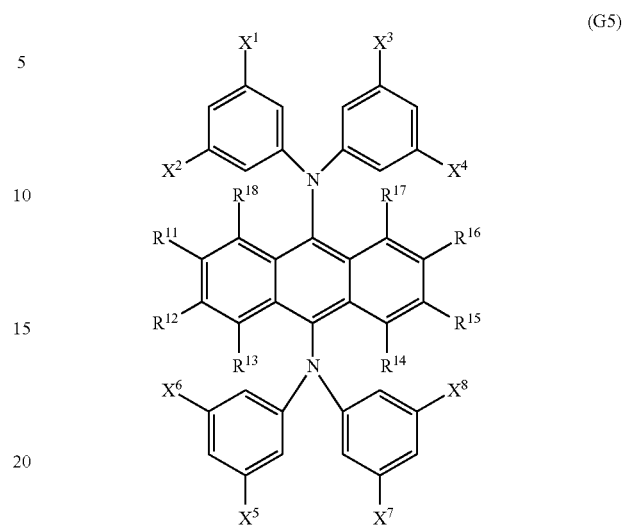

(G5)

In General Formula (G5) above, $X^1$ to $X^8$ each independently represent any one of an alkyl group having 1 to 10 carbon atoms, a substituted or unsubstituted cycloalkyl group having 3 to 10 carbon atoms, and a trialkylsilyl group having 3 to 10 carbon atoms, and $R^{11}$ to $R^{18}$ each independently represent any one of hydrogen, a branched-chain alkyl group having 3 to 10 carbon atoms, a substituted or unsubstituted cycloalkyl group having 3 to 10 carbon atoms, a trialkylsilyl group having 3 to 10 carbon atoms, and a substituted or unsubstituted aryl group having 6 to 25 carbon atoms.

Note that the luminophore 130b included in the first organic compound 121 represented by General Formula (G1) and General Formula (G3) above is represented by a substituted or unsubstituted condensed aromatic ring having 10 to 30 carbon atoms or a substituted or unsubstituted condensed heteroaromatic ring having 10 to 30 carbon atoms. The luminophore 130b included in the first organic compound 121 represented by General Formula (G2), General Formula (G4), and General Formula (G5) above is a quinacridone skeleton shown in the formulae. In General Formula (G1), General Formula (G2), General Formula (G3), General Formula (G4), and General Formula (G5), $X^1$ to $X^{12}$ represent the protecting groups 131 included in the first organic compound 121.

In General Formula (G1) and General Formula (G3) above, as the substituted or unsubstituted condensed aromatic ring having 10 to 30 carbon atoms or the substituted or unsubstituted condensed heteroaromatic ring having 10 to 30 carbon atoms, a phenanthrene skeleton, a stilbene skeleton, an acridone skeleton, a phenoxazine skeleton, a phenothiazine skeleton, and the like are given. It is also possible to use a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, a naphthobisbenzofuran skeleton, and the like, which can increase the fluorescence quantum yield.

In General Formula (G1), General Formula (G2), General Formula (G3), and General Formula (G4) above, as the aromatic hydrocarbon group having 6 to 13 carbon atoms, a phenyl group, a biphenyl group, a naphthyl group, a fluorenyl group, and the like can be given.

In General Formulae (G1) and (G2), General Formula (G3), and General Formula (G4) above, specific examples of the alkyl group having 1 to 10 carbon atoms include a methyl group, an ethyl group, a propyl group, a pentyl group, and a hexyl group.

In General Formula (G1), General Formula (G2), General Formula (G3), General Formula (G4), and General Formula (G5) above, specific examples of the cycloalkyl group having 3 to 10 carbon atoms include a cyclopropyl group, a cyclobutyl group, a cyclohexyl group, a norbornyl group, and an adamantyl group. In the case where the cycloalkyl group has a substituent, specific examples of the substituent include an alkyl group having 1 to 7 carbon atoms, such as a methyl group, an ethyl group, a propyl group, an isopropyl group, a butyl group, an isobutyl group, a sec-butyl group, a tert-butyl group, a pentyl group, or a hexyl group, a cycloalkyl group having 5 to 7 carbon atoms, such as a cyclopentyl group, a cyclohexyl group, a cycloheptyl group, or a 8,9,10-trinorbornanyl group, and an aryl group having 6 to 12 carbon atoms, such as a phenyl group, a naphthyl group, or a biphenyl group.

In General Formula (G5), specific examples of the branched-chain alkyl group having 3 to 10 carbon atoms include an isopropyl group, a sec-butyl group, an isobutyl group, a tert-butyl group, an isopentyl group, a sec-pentyl group, a tert-pentyl group, a neopentyl group, an isohexyl group, a 3-methylpentyl group, a 2-methylpentyl group, a 2-ethylbutyl group, a 1,2-dimethylbutyl group, and a 2,3-dimethylbutyl group.

In General Formula (G1), General Formula (G2), General Formula (G3), General Formula (G4), and General Formula (G5) above, specific examples of the trialkylsilyl group having 3 to 12 carbon atoms include a trimethylsilyl group, a triethylsilyl group, and a tert-butyl dimethylsilyl group.

In General Formula (G1), General Formula (G2), General Formula (G3), and General Formula (G4) above, in the case where the condensed aromatic ring, the condensed heteroaromatic ring, the aromatic hydrocarbon group having 6 to 13 carbon atoms, or the cycloalkyl group having 3 to 10 carbon atoms has a substituent, examples of the substituent include an alkyl group having 1 to 7 carbon atoms, such as a methyl group, an ethyl group, a propyl group, an isopropyl group, a butyl group, an isobutyl group, a sec-butyl group, a tert-butyl group, a pentyl group, or a hexyl group, a cycloalkyl group having 5 to 7 carbon atoms, such as a cyclopentyl group, a cyclohexyl group, a cycloheptyl group, or a 8,9,10-trinorbornanyl group, and an aryl group having 6 to 12 carbon atoms, such as a phenyl group, a naphthyl group, or a biphenyl group.

In General Formula (G5) above, specific examples of the aryl group having 6 to 25 carbon atoms include a phenyl group, a naphthyl group, a biphenyl group, a fluorenyl group, and a spirofluorenyl group. In the case where the aryl group has a substituent, examples of the substituent include the alkyl group having 1 to 10 carbon atoms, the branched-chain alkyl group having 3 to 10 carbon atoms, the substituted or unsubstituted cycloalkyl group having 3 to 10 carbon atoms, and the trialkylsilyl group having 3 to 10 carbon atoms, which are described above.

Note that the first organic compound 121 shown in General Formula (G5) has a structure in which the protecting groups 131 represented by $X^1$ to $X^8$ are bonded to an anthracene skeleton, which is the luminophore 130b, via a phenylene group. The two protecting groups 131 bonded to one phenylene group are preferably bonded at the meta-position of the phenylene group. With this structure, the luminophore 130b can be efficiently covered with the protecting groups 131 because the anthracene skeleton has a small emission area; thus, energy transfer by the Dexter mechanism can be inhibited.

Specific examples of the first organic compound 121 shown in General Formula (G1) to General Formula (G5) are shown in Structural Formula (100) to Structural Formula (105) and Structural Formula (200) to Structural Formula (284) below. Note that specific examples of the first organic compound 121 shown in General Formula (G1) to General Formula (G5) are not limited to those shown below.

[Chemical Formula 10]

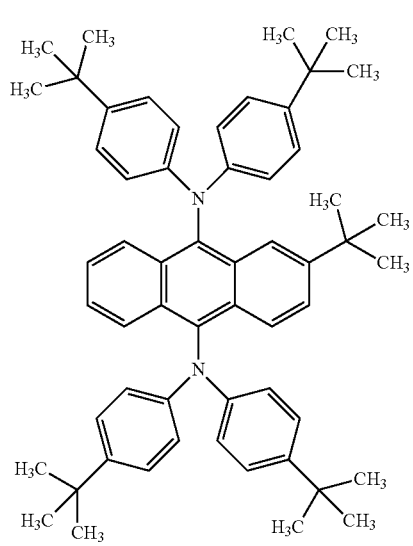

(100)

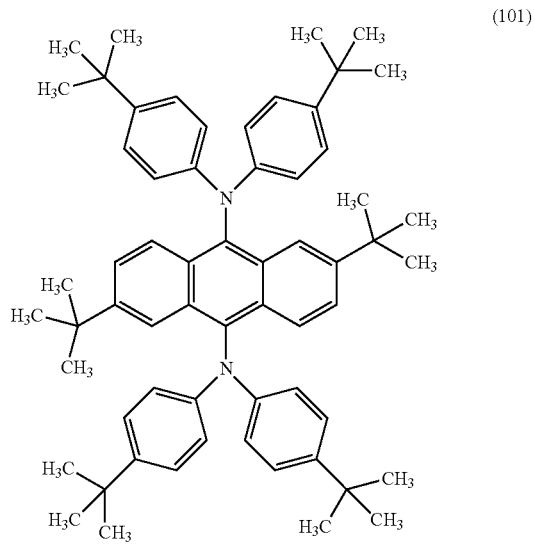

(101)

(102)
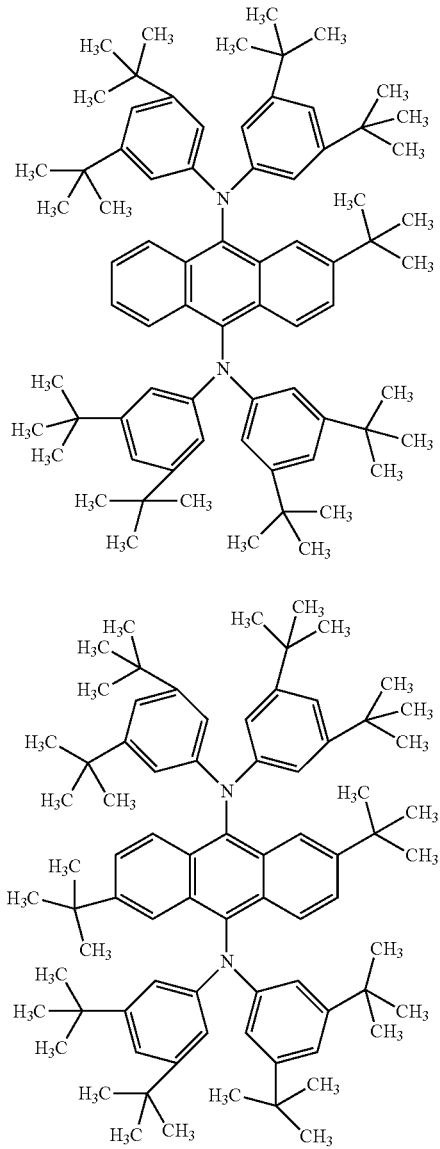
(103)
(104)
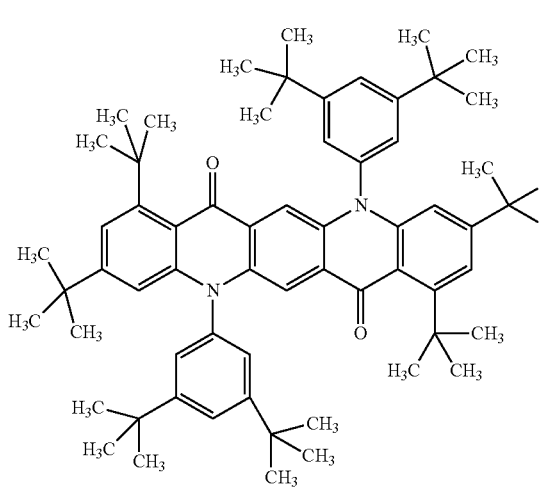
(105)
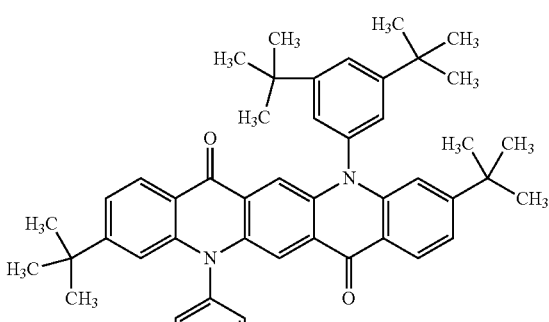
[Chemical Formula 11]
(200)
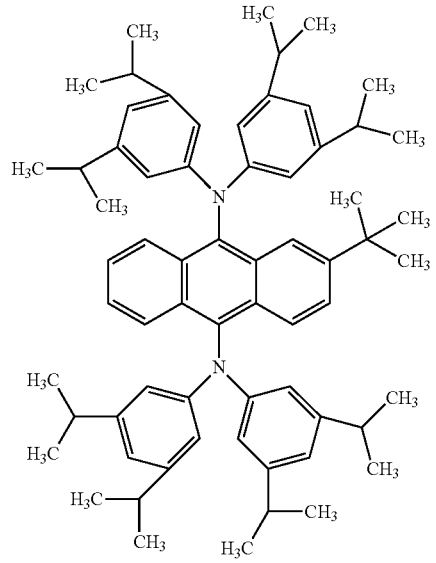
(201)
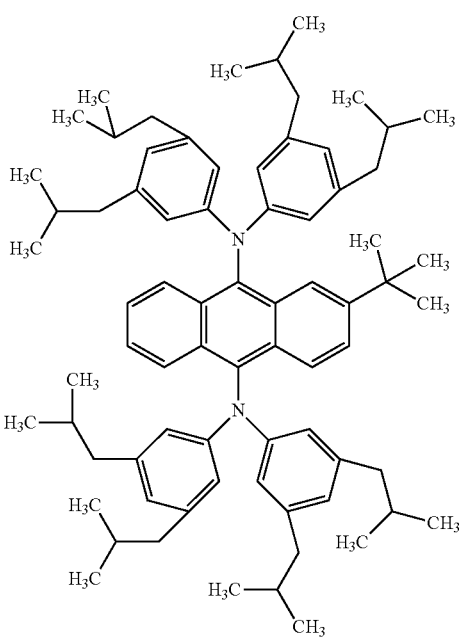

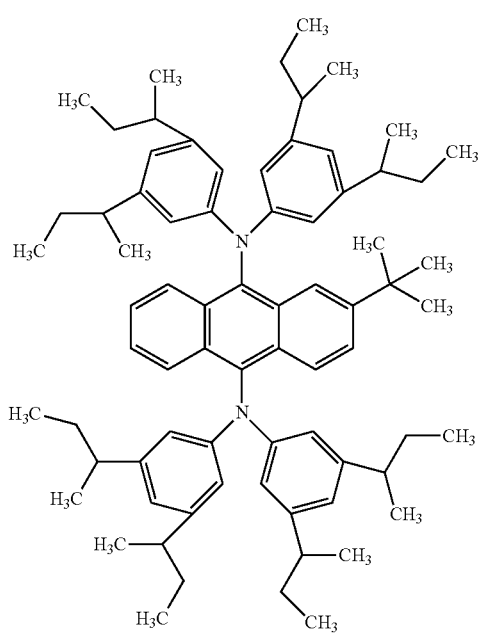
(202)
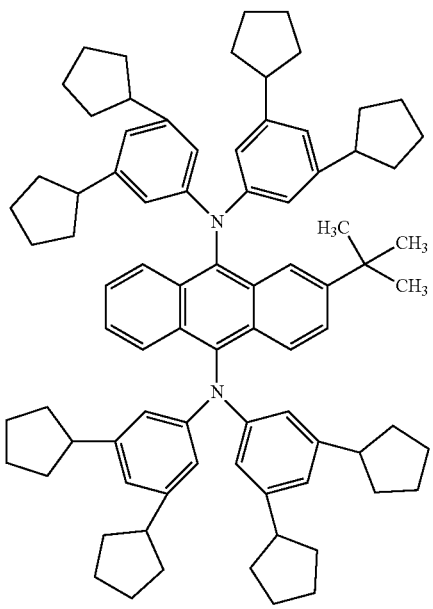
(204)
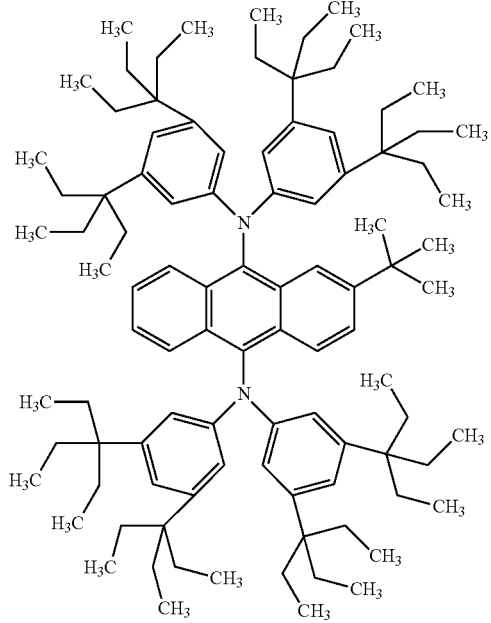
(203)
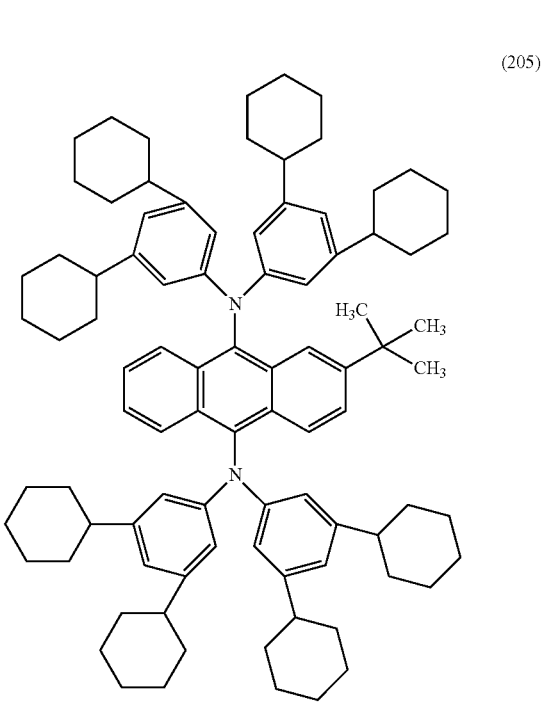
(205)

[Chemical Formula 12]
(206)
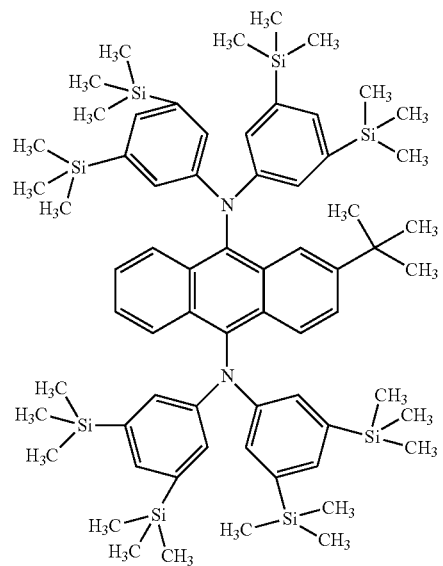
(207)
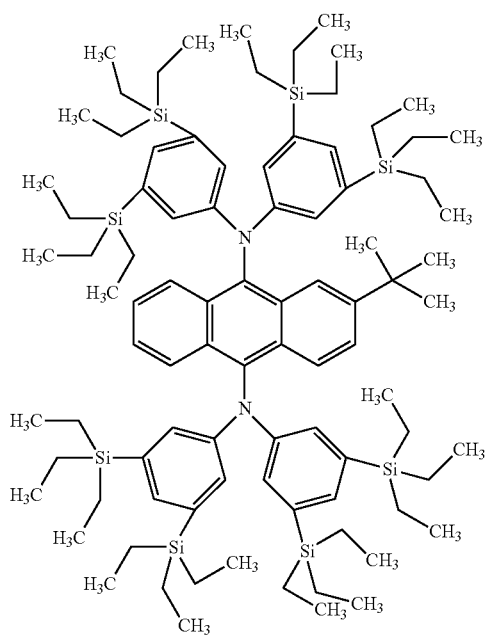
(208)
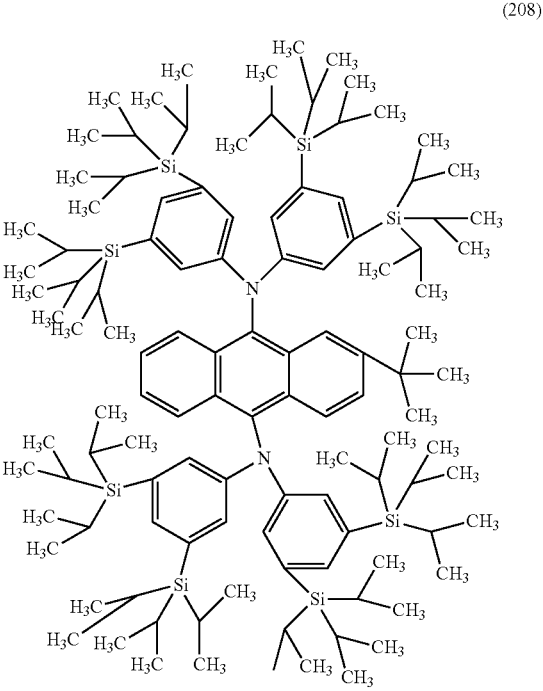
(209)
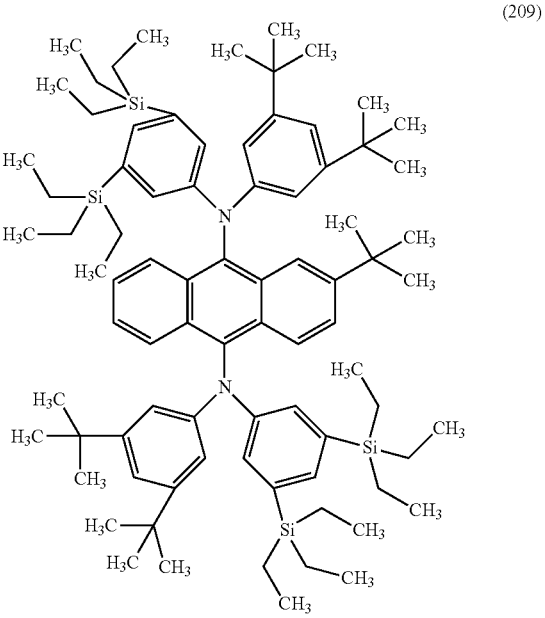

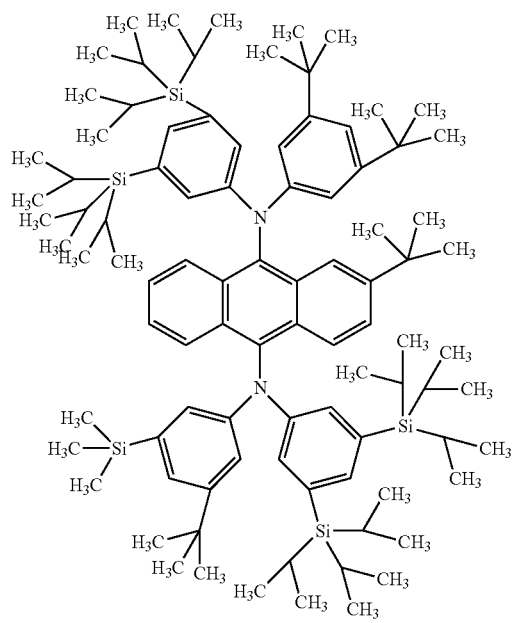
(210)
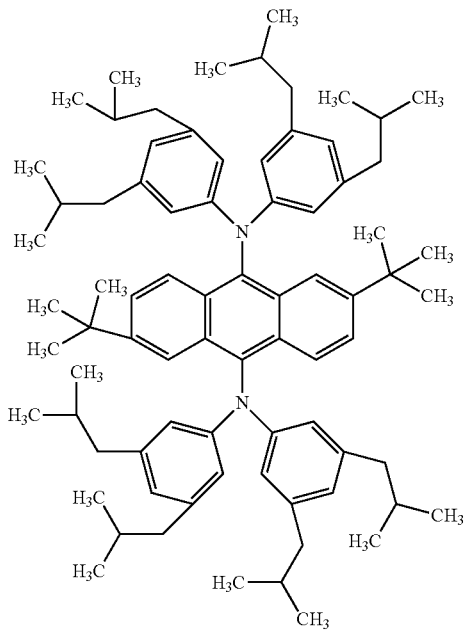
(212)
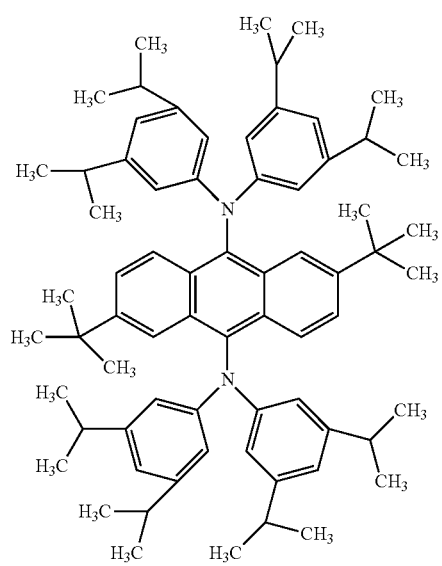
(211)
(213)

[Chemical Formula 13]
(214)
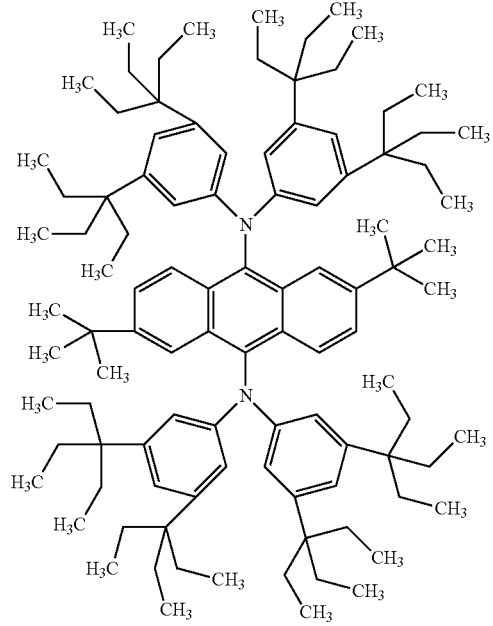
(215)
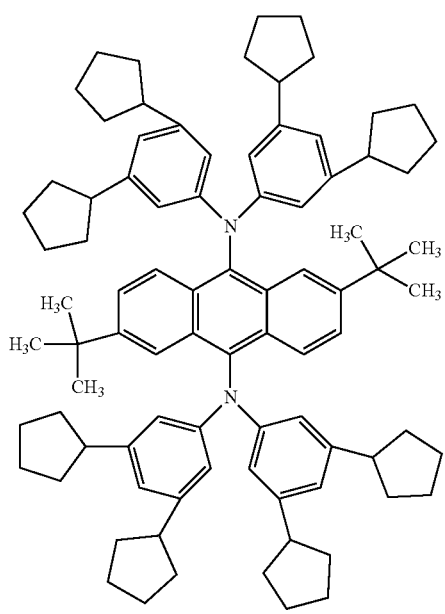
(216)
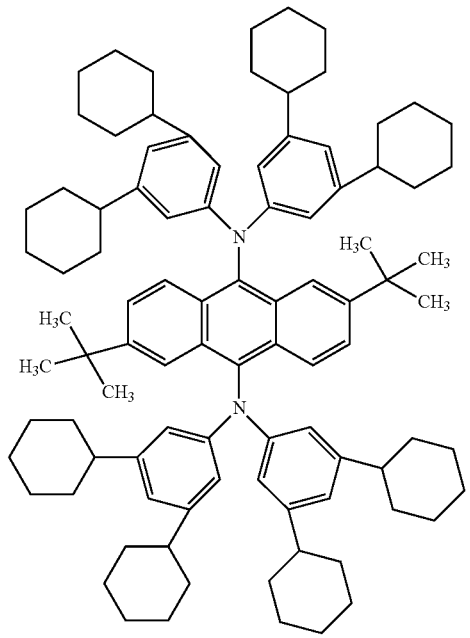
(217)
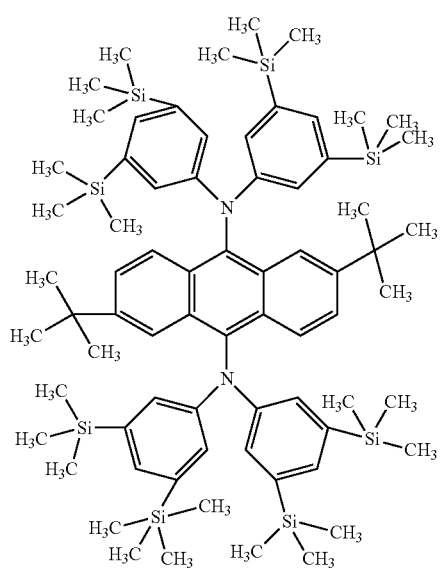

(218)
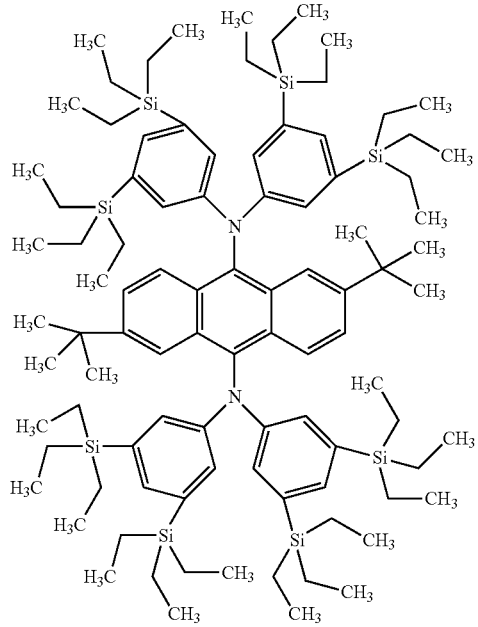
(220)
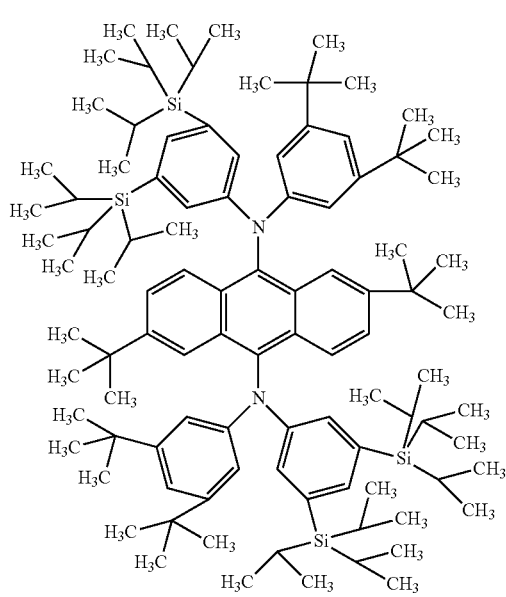
(219)
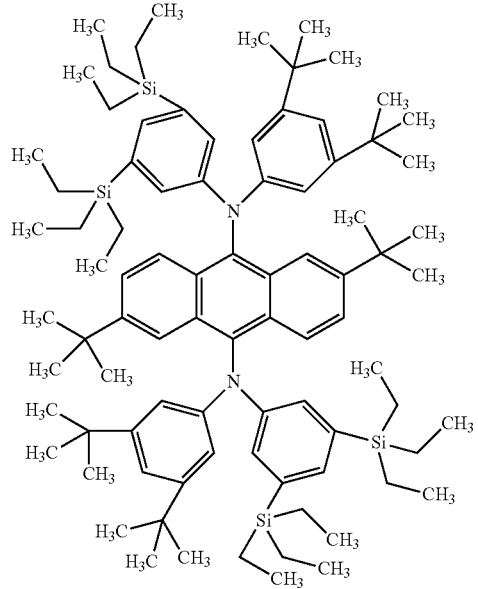
(221)
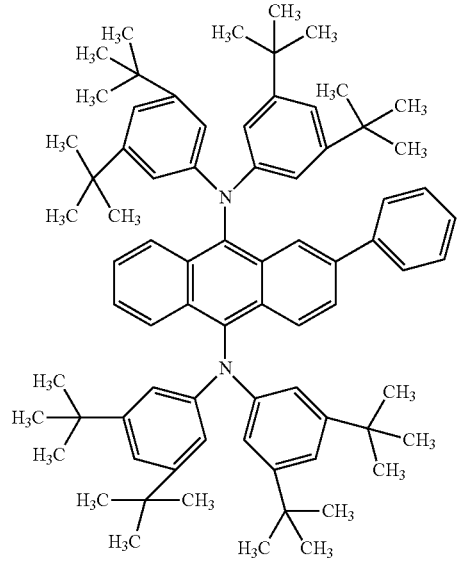

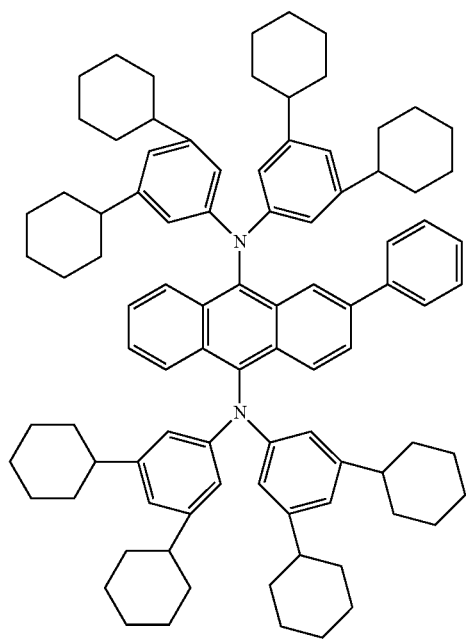
(222)
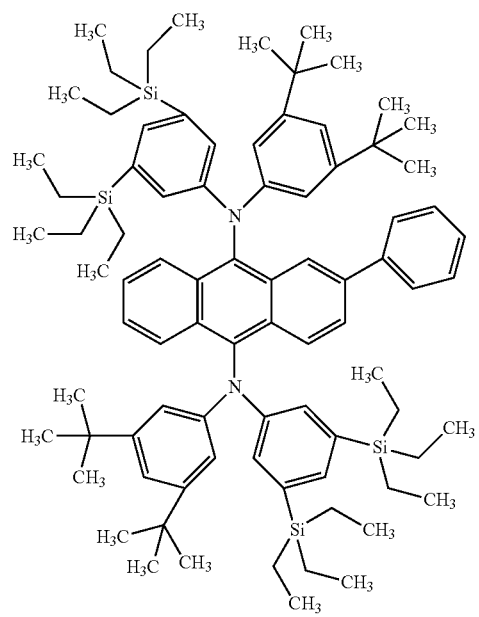
(224)
[Chemical Formula 14]
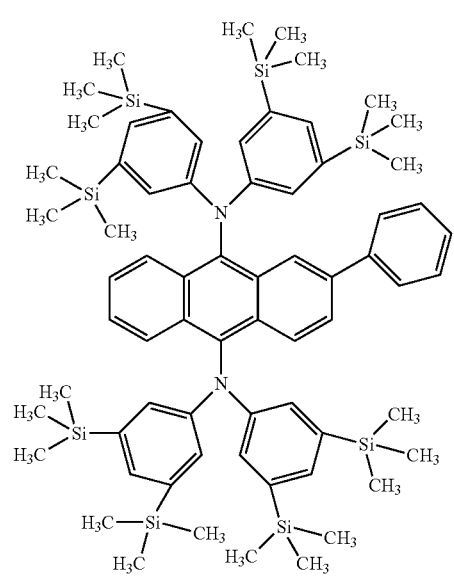
(223)
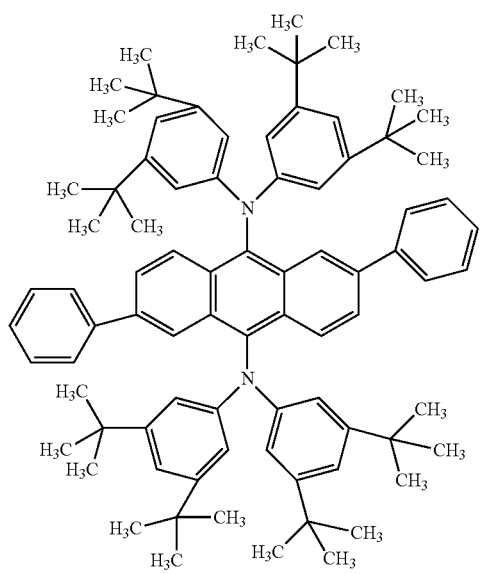
(225)

(226)
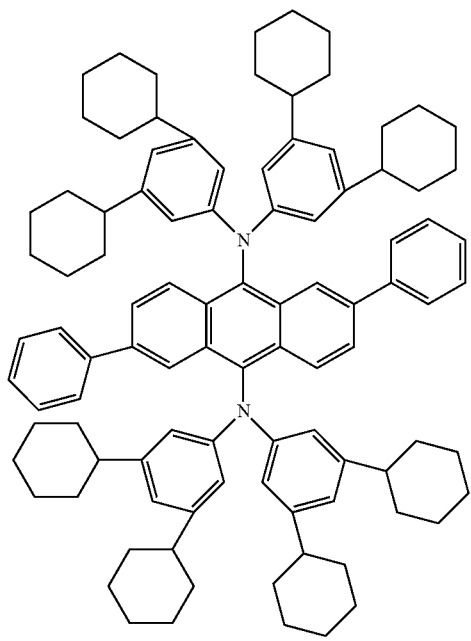
(227)
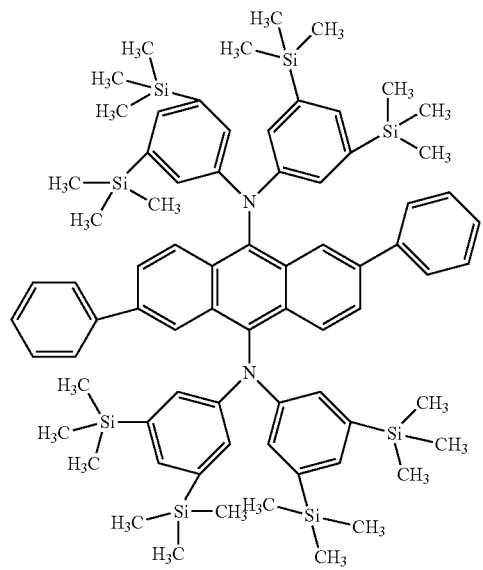
(228)
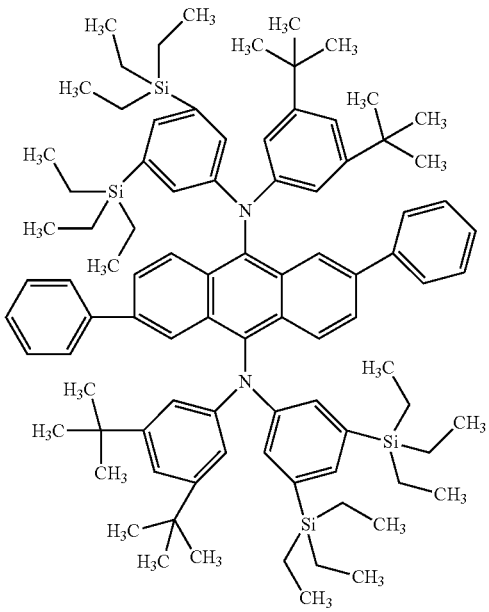
(229)
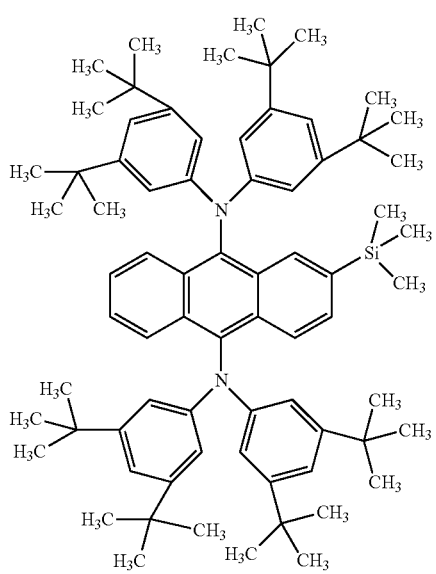

[Chemical Formula 15]
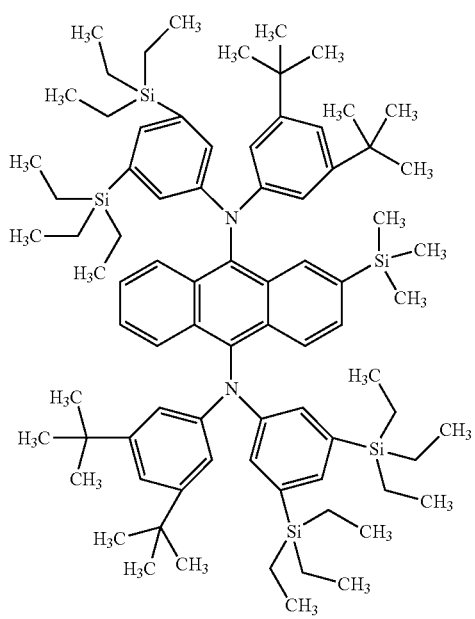
(230)
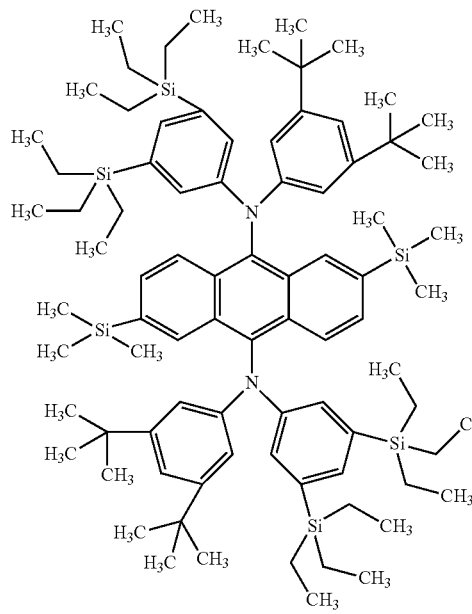
(232)
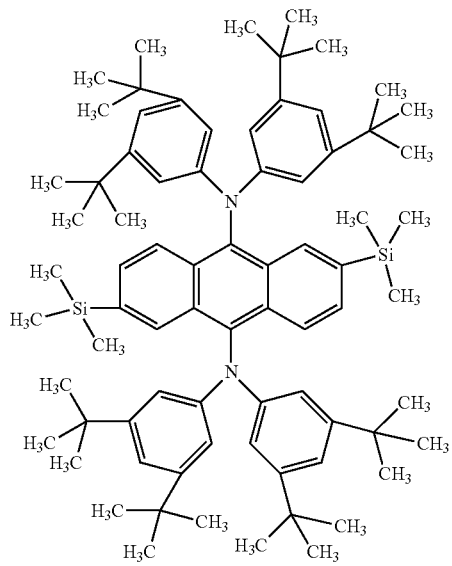
(231)
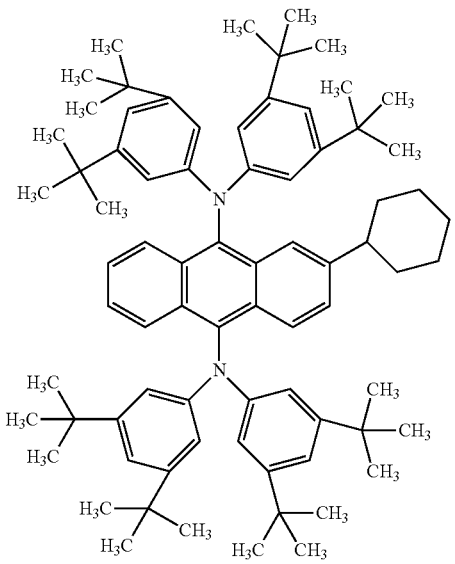
(233)

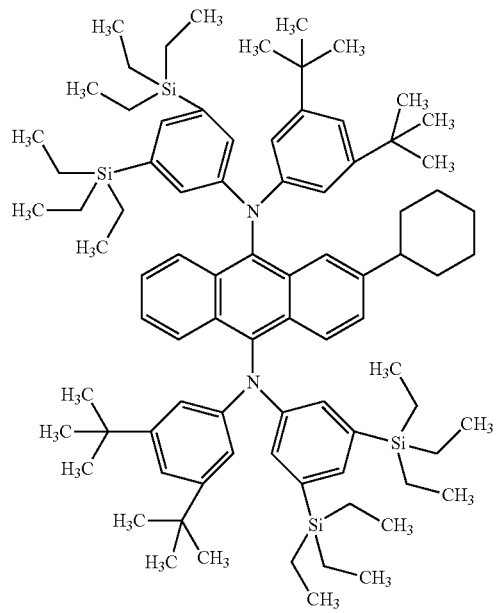
(234)
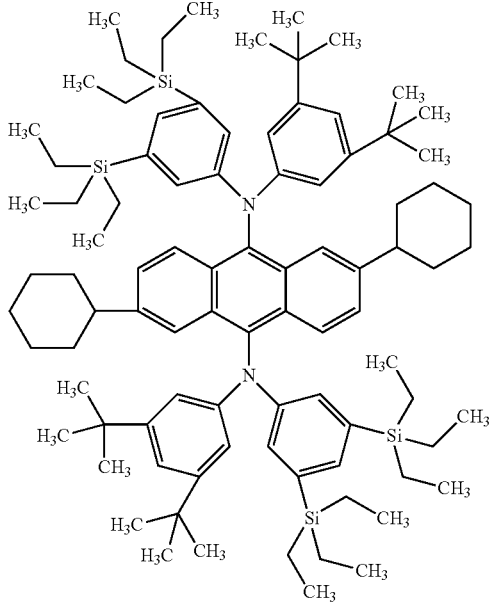
(236)
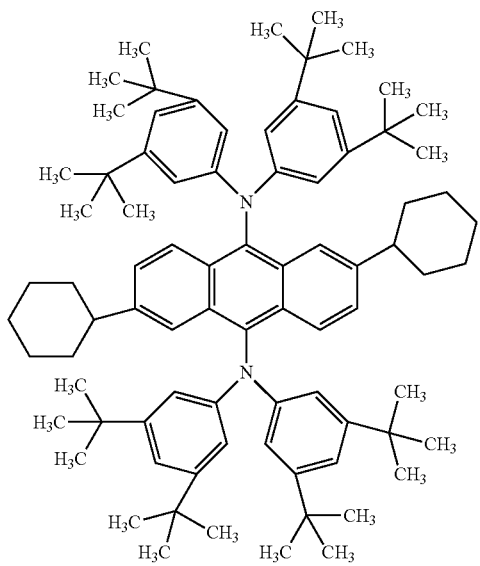
(235)
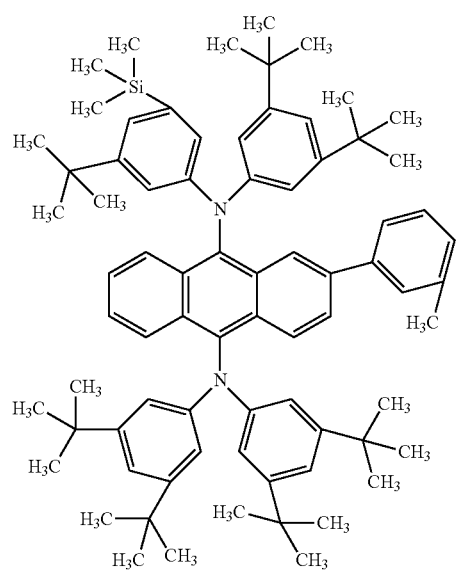
(237)

(238)
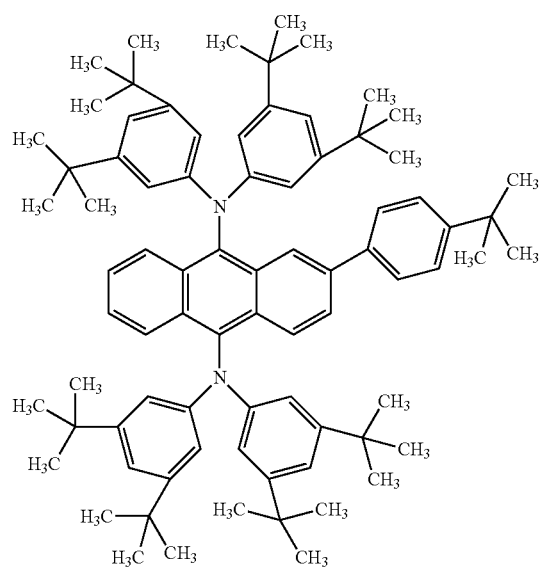
(239)
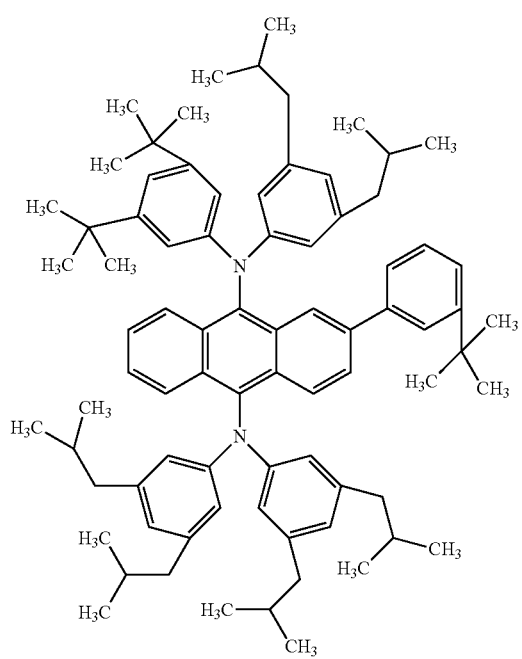
(240)
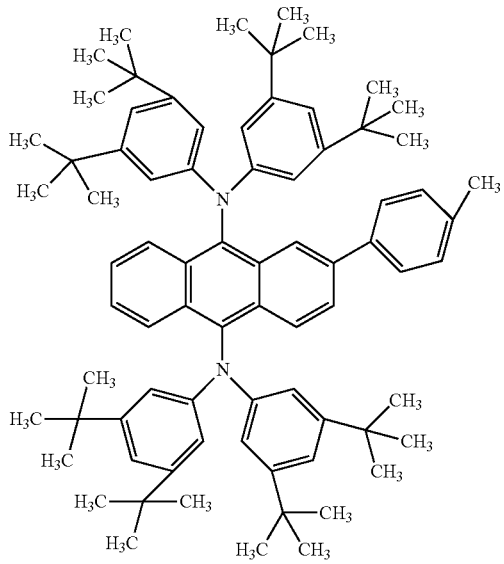
[Chemical Formula 16]
(241)
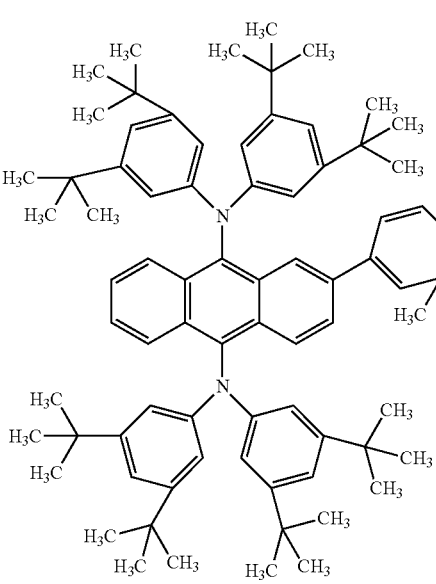

(242)
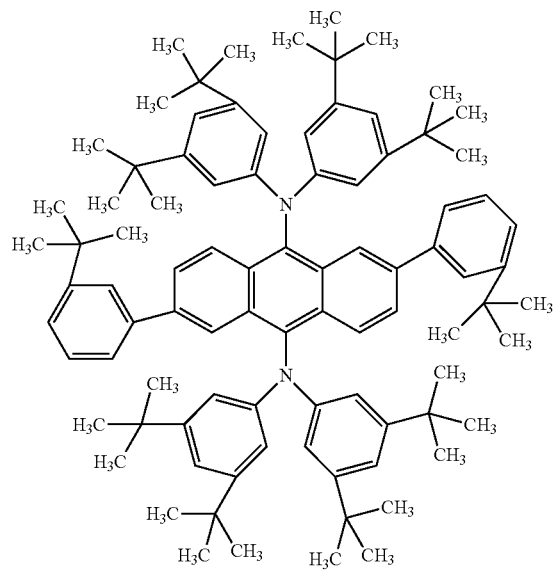
(243)
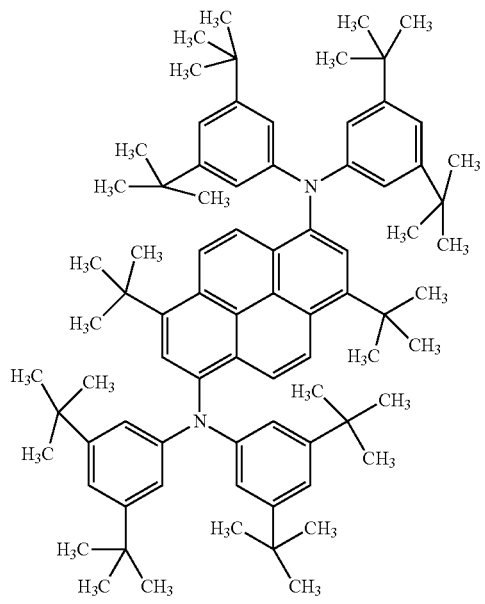
(244)
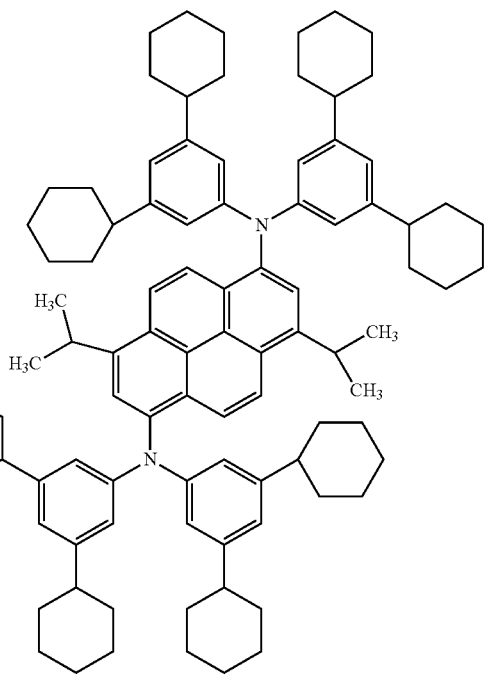
(245)
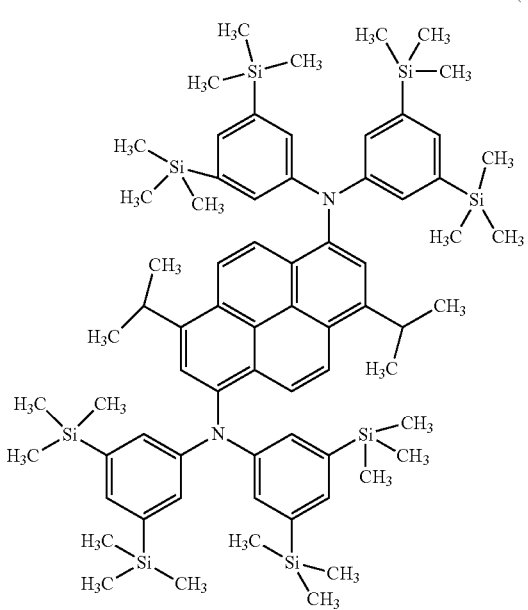

(246)
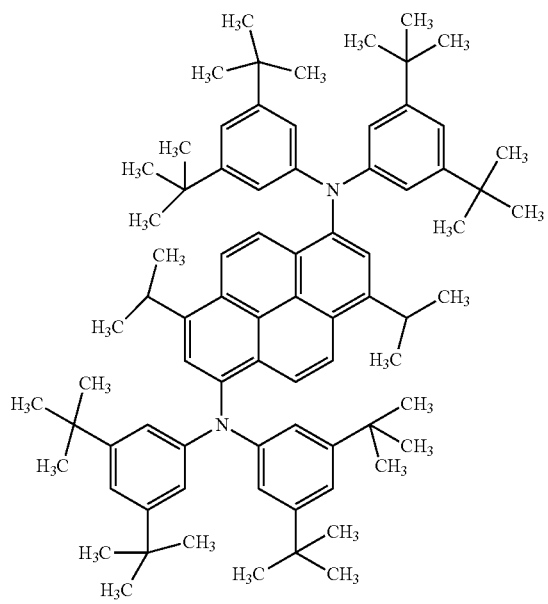
(247)
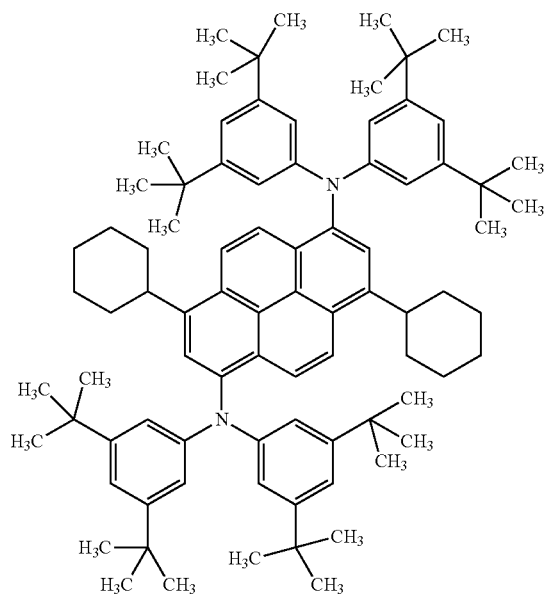
(248)
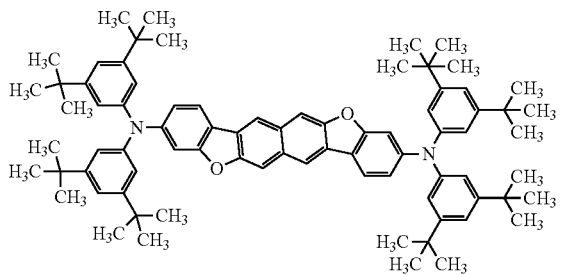
[Chemical Formula 17]
(249)
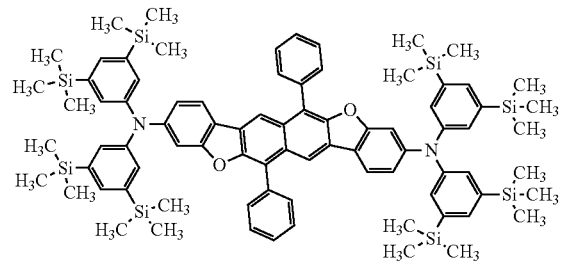
(250)
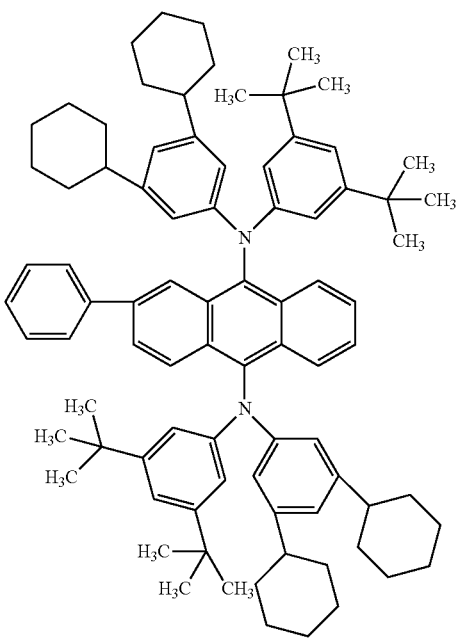
(251)
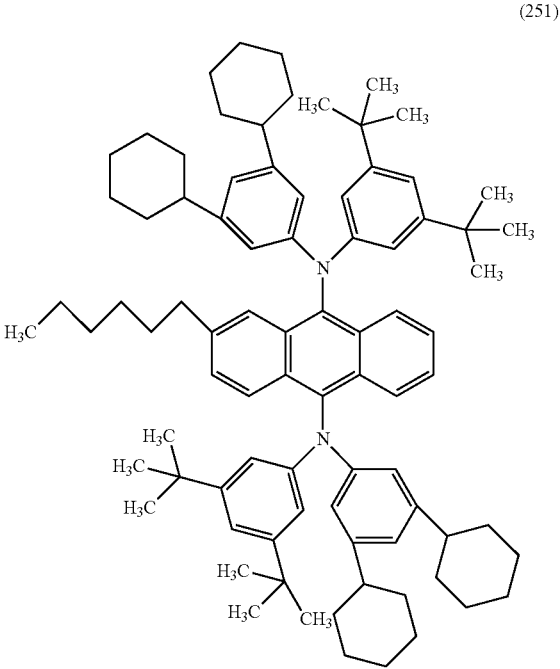

-continued
(252)
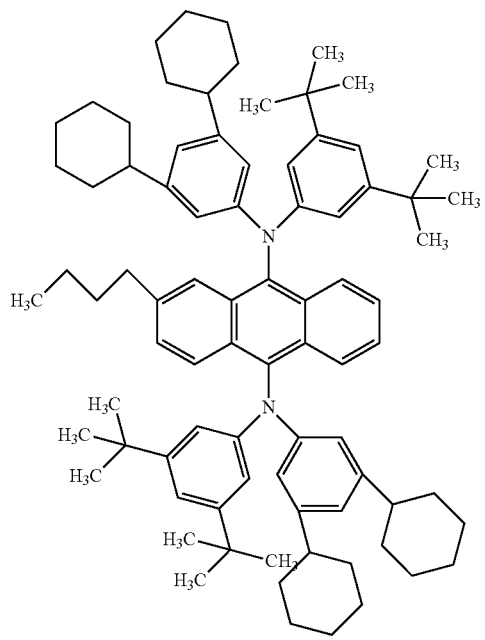
(253)
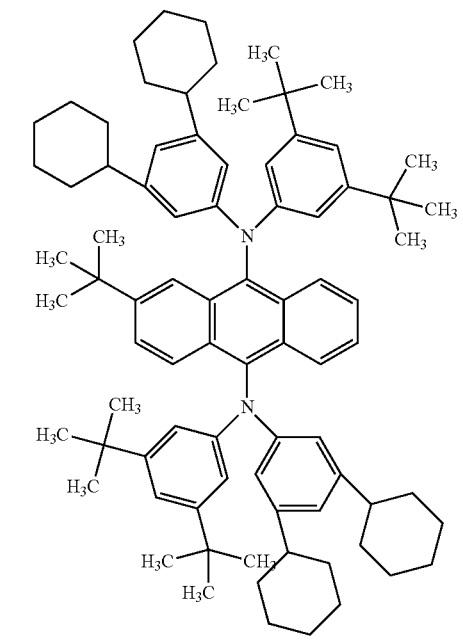
-continued
(254)
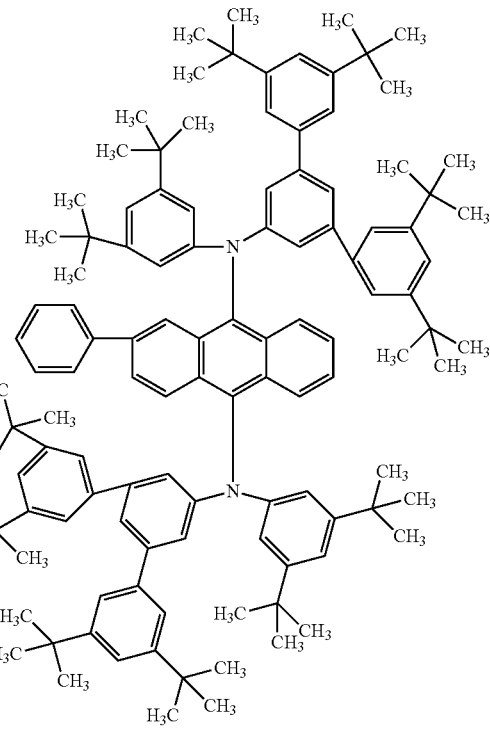
(255)
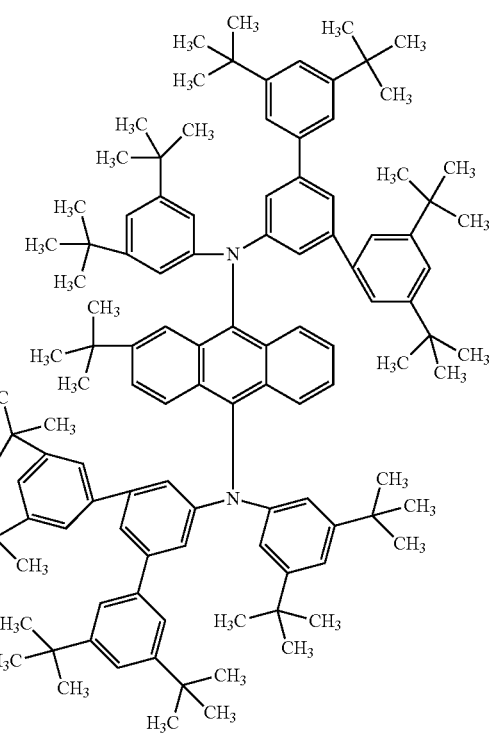

[Chemical Formula 18]
(256)
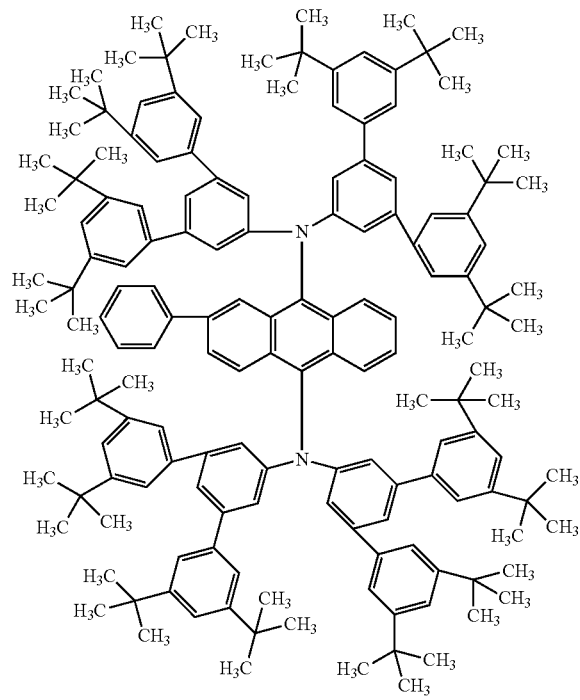
(257)
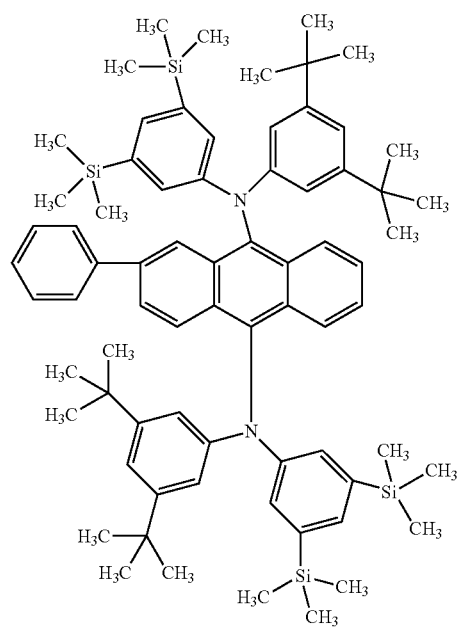
(258)
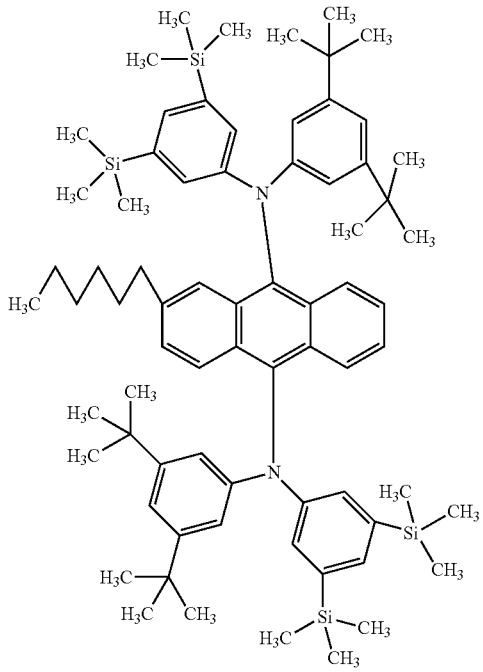
(259)
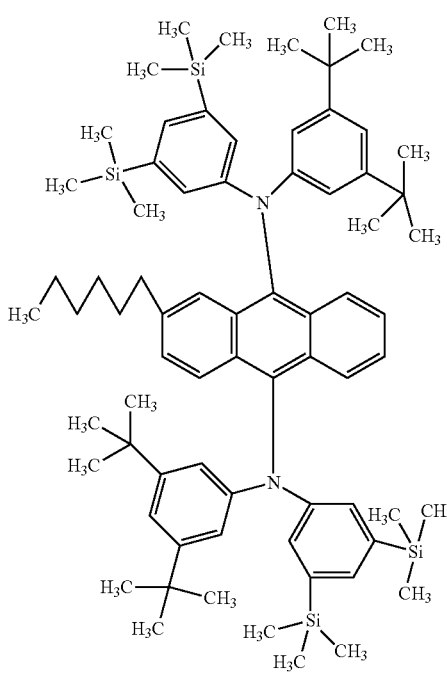

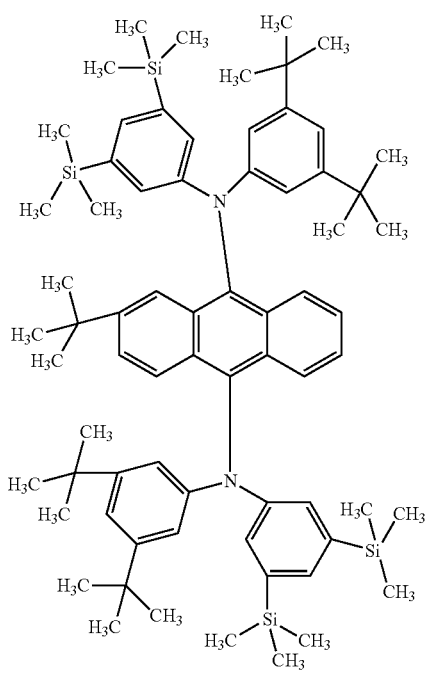
(260)
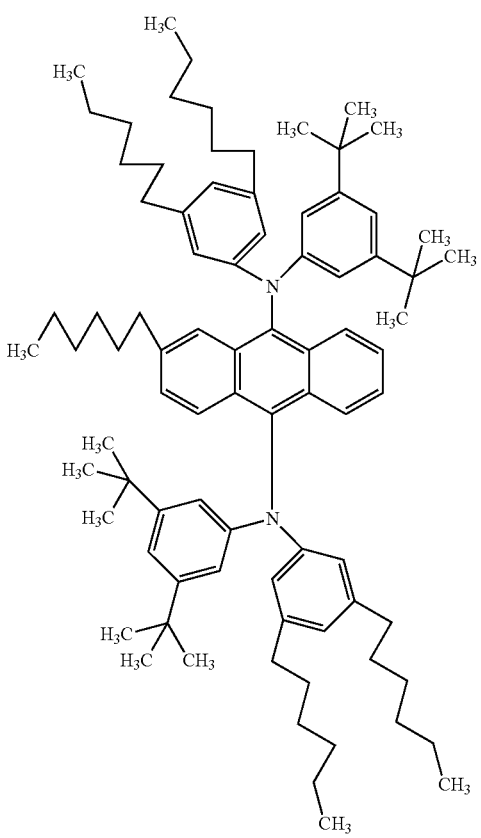
(262)
[Chemical Formula 19]
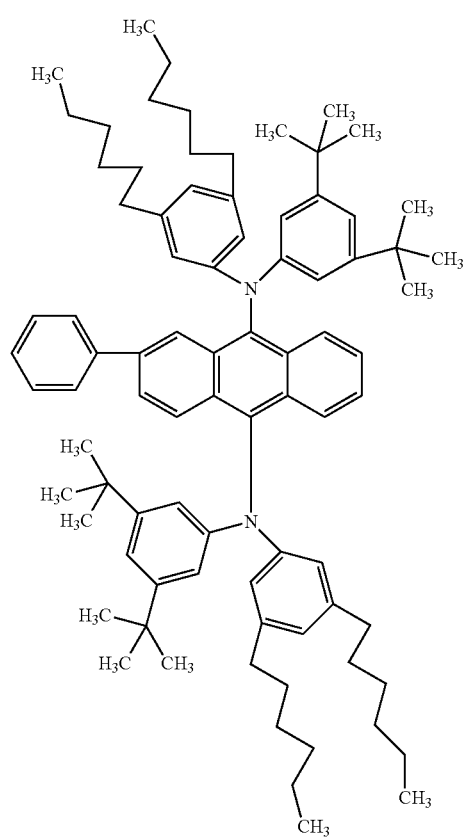
(261)
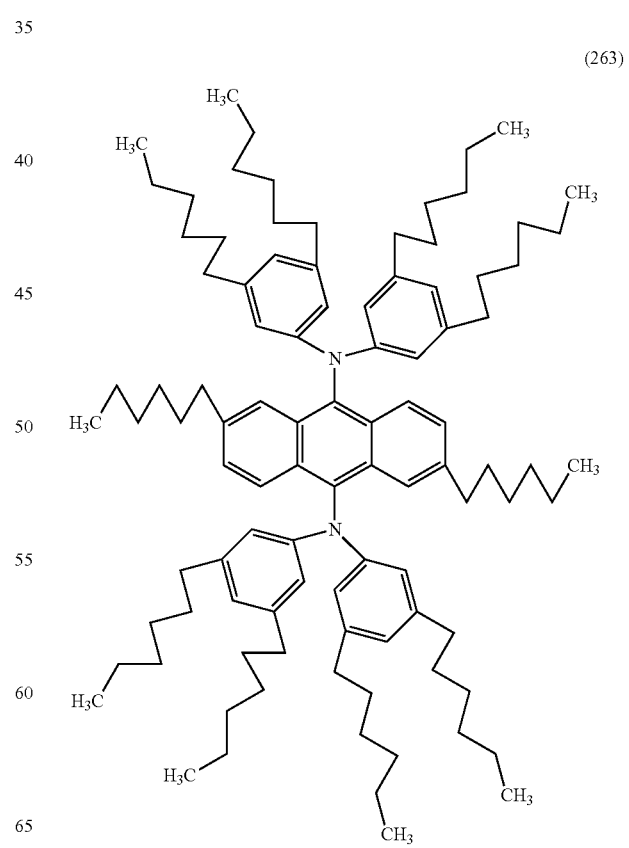
(263)

[Chemical Formula 20]
(264)
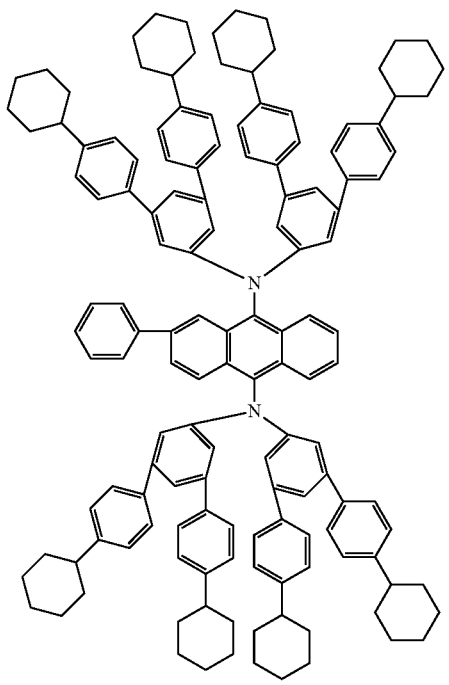
(265)
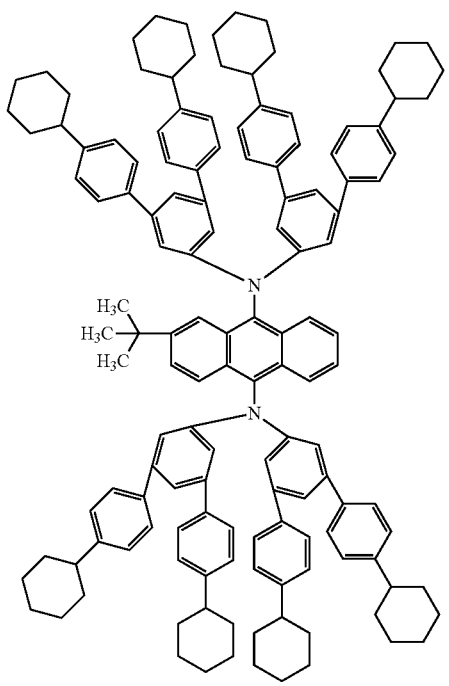
(266)
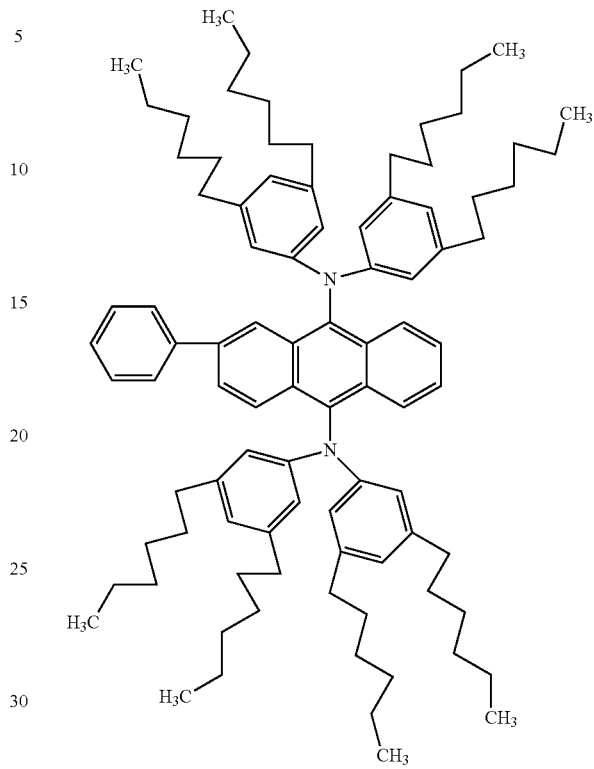
(267)
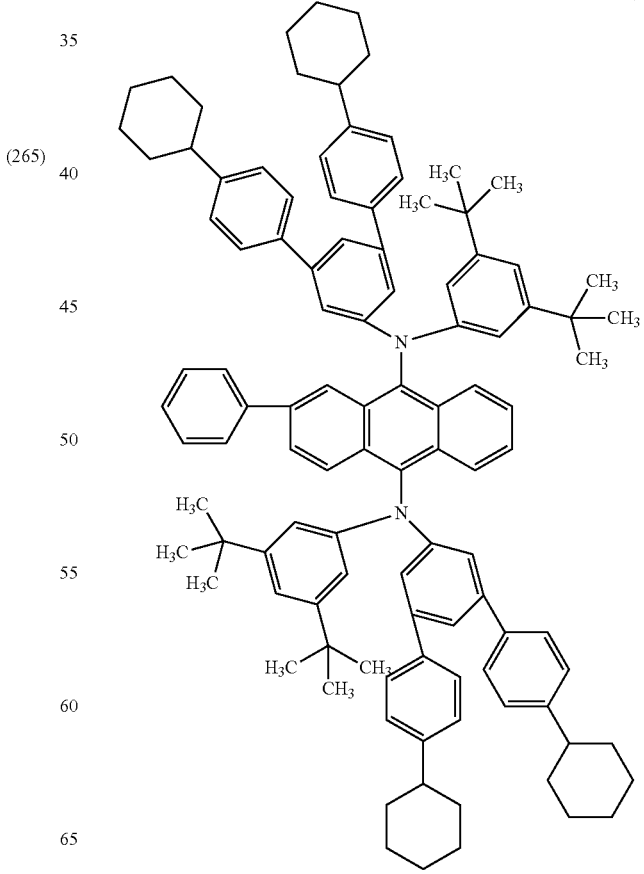

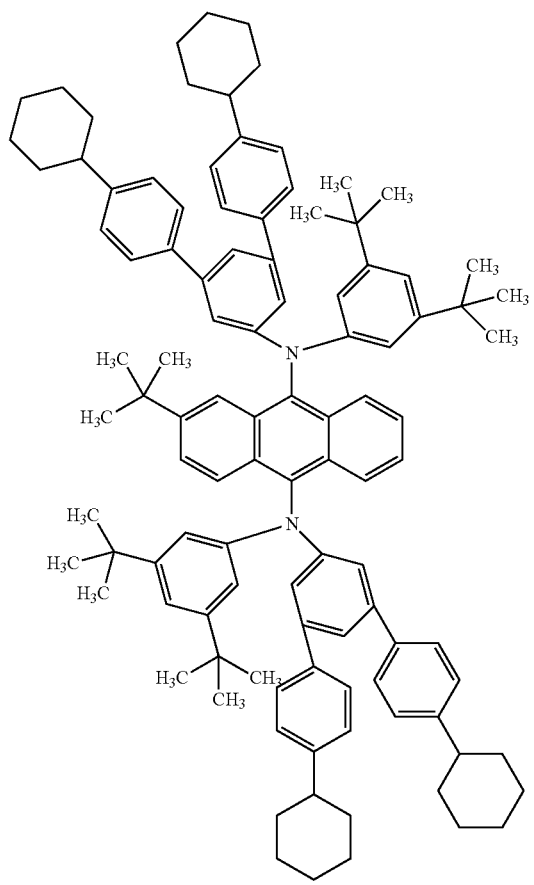
(268)
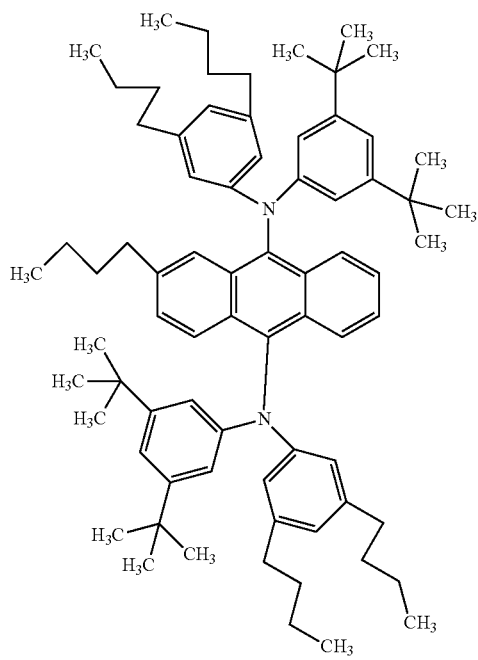
(270)
[Chemical Formula 21]
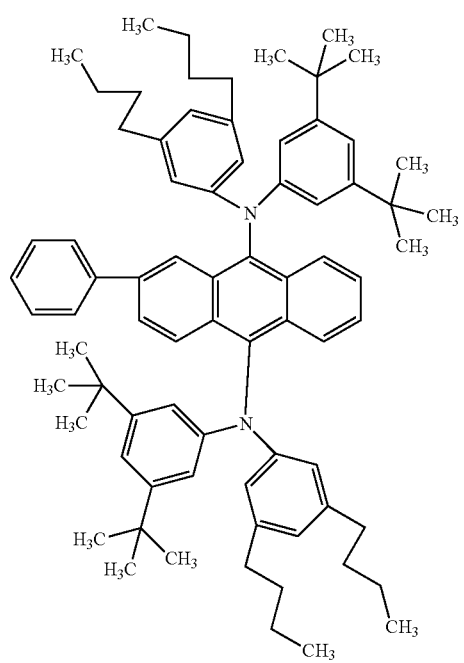
(269)
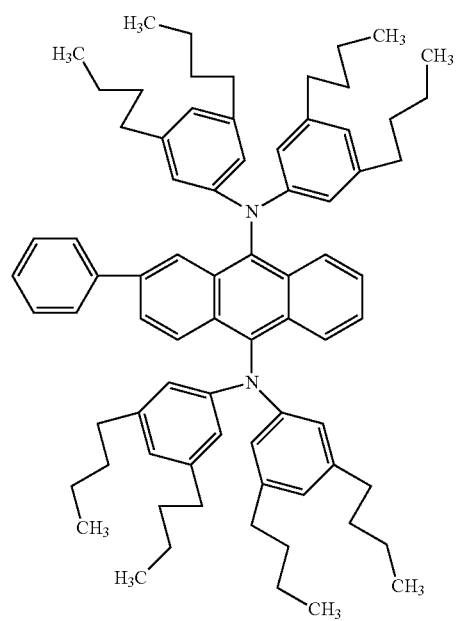
(271)

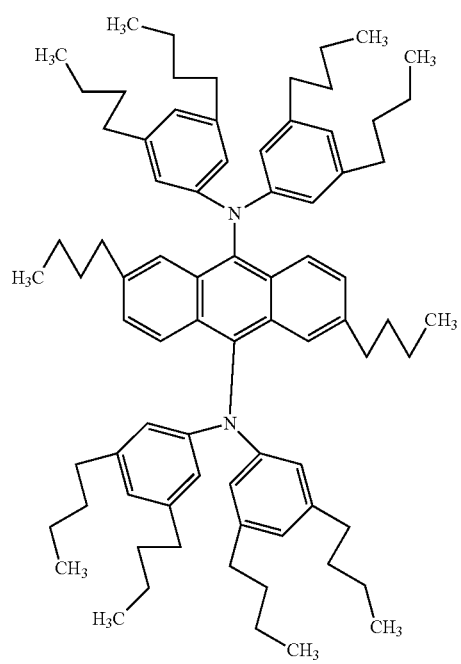
(272)
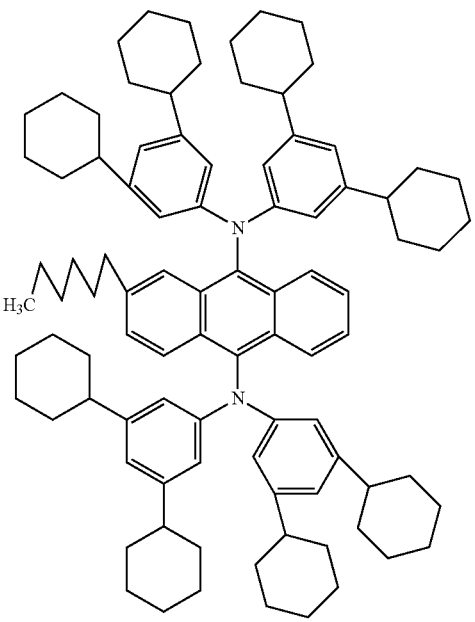
(274)
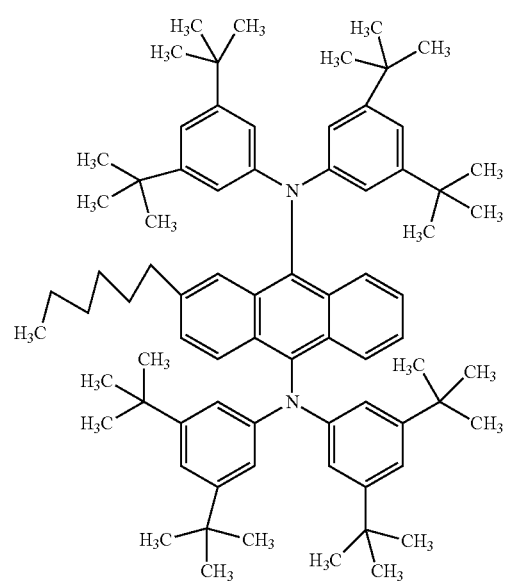
(273)
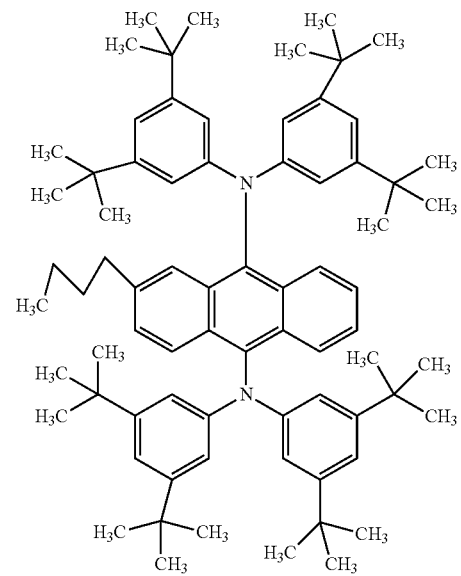
(275)

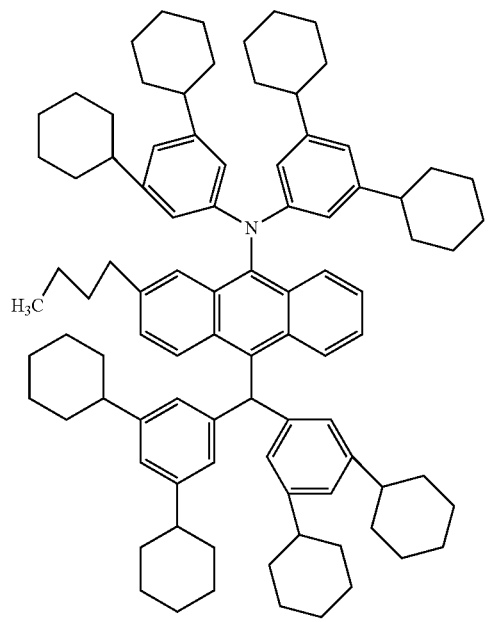
(276)
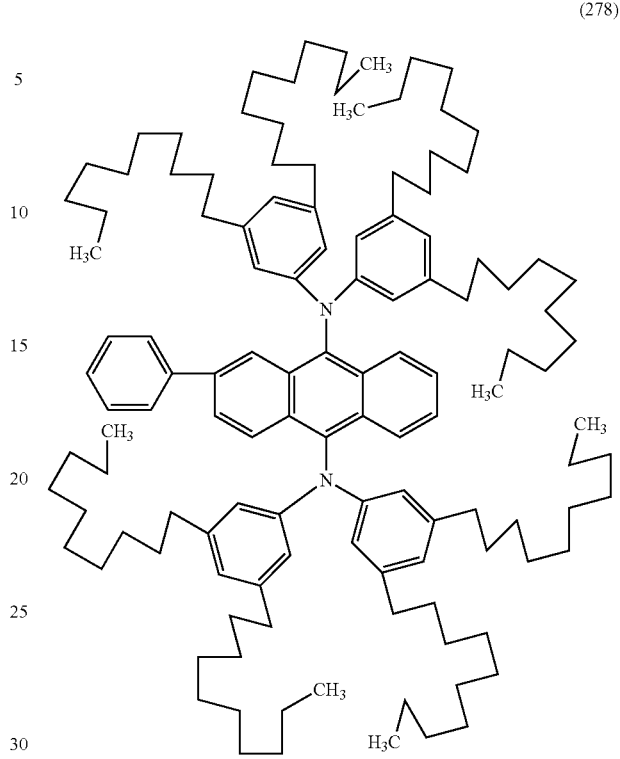
(278)
[Chemical Formula 22]
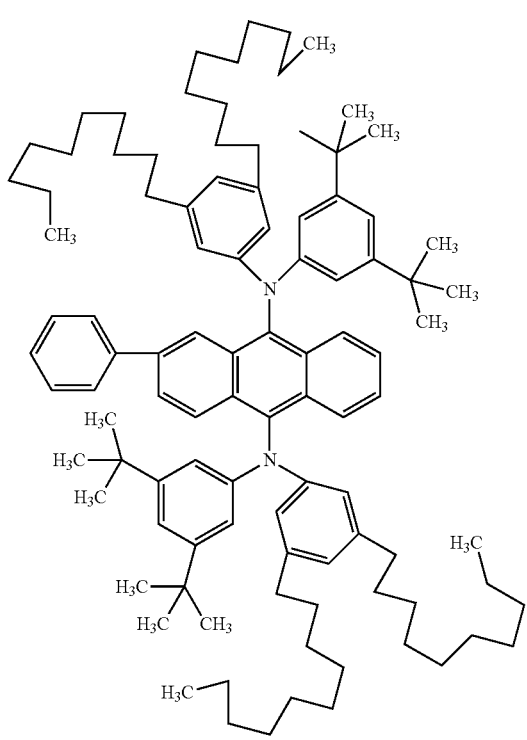
(277)
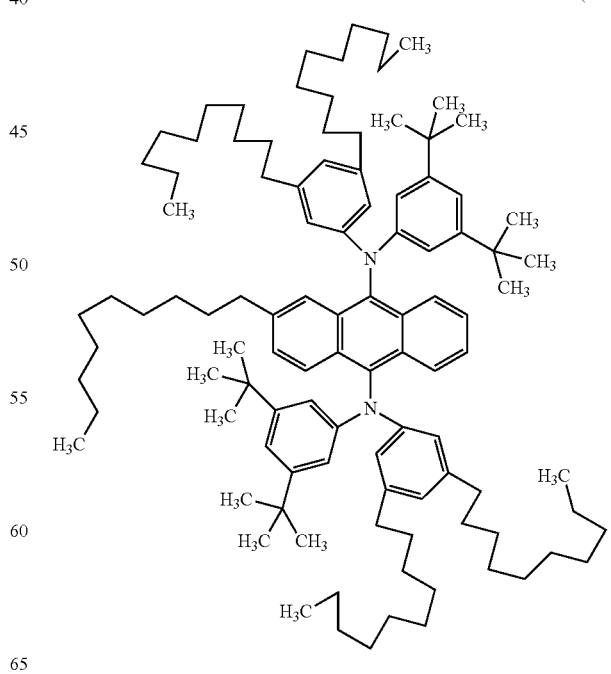
(279)

(280)
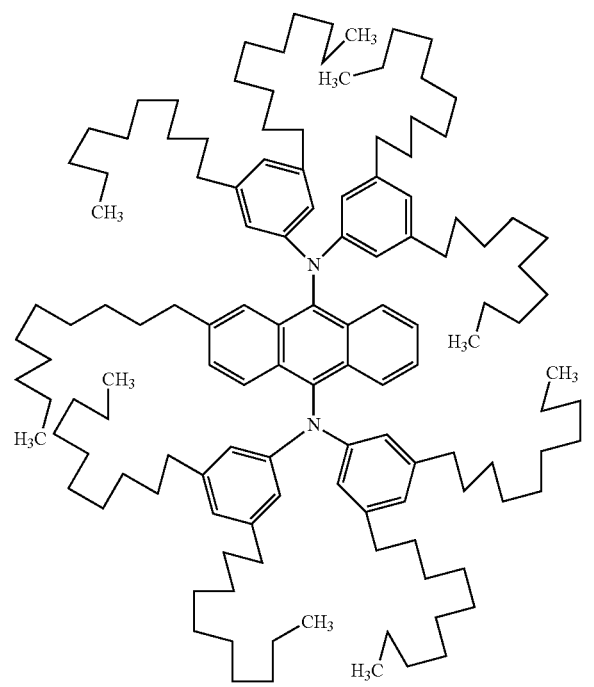
(282)
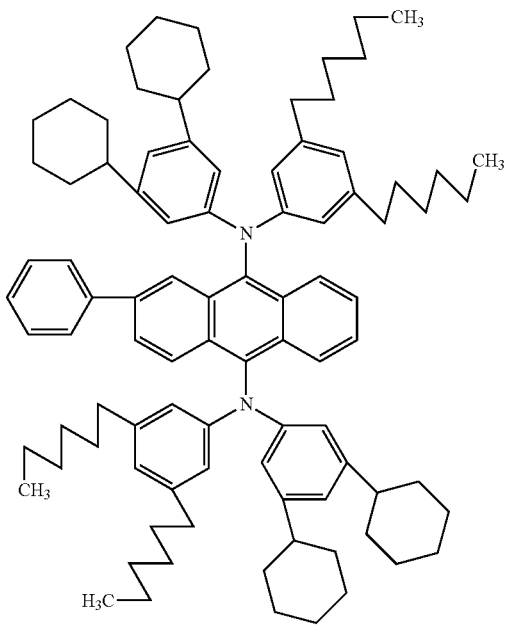
[Chemical Formula 23]
(281)
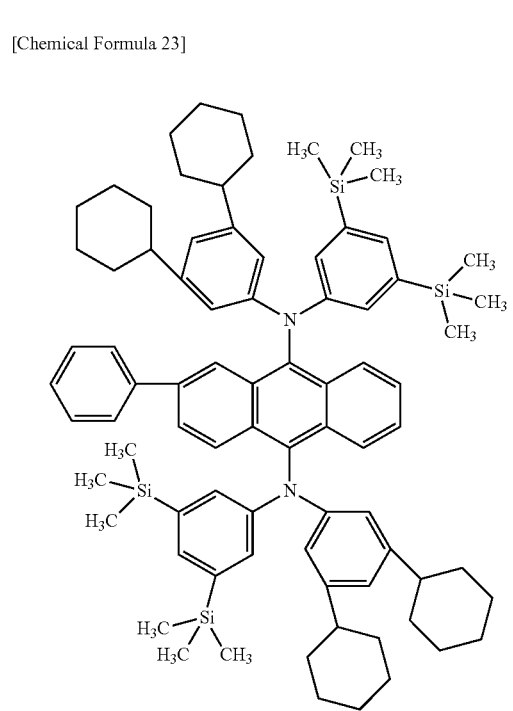
(283)
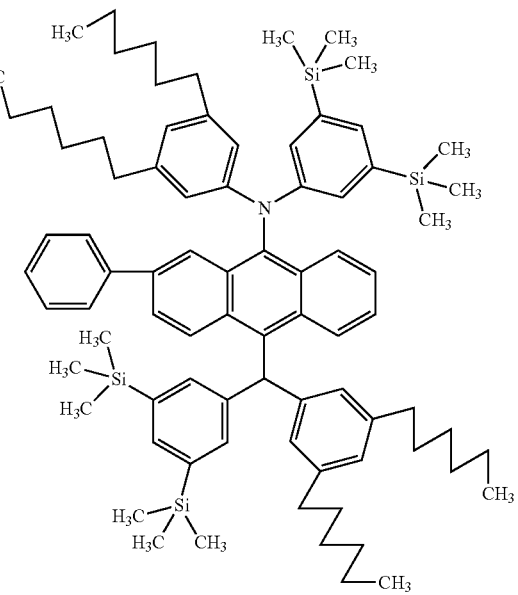

(284)

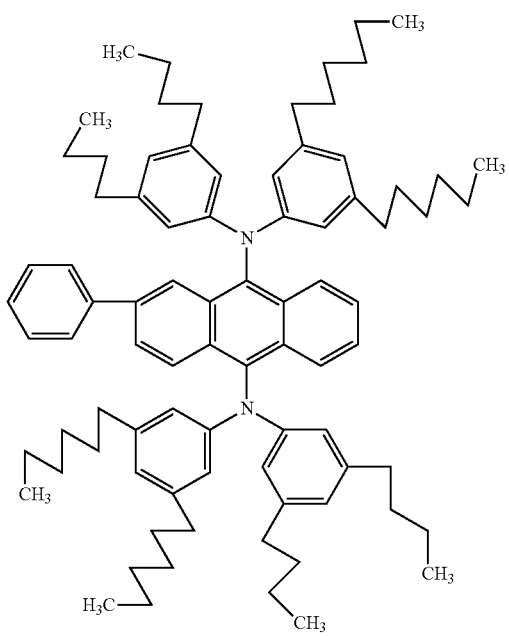

Among the aforementioned specific examples of the first organic compound 121, a structure of N,N'-[(2-tert-butylanthracene)-9,10-diyl]-N,N'-bis(3,5-di-tert-butylphenyl)amine (abbreviation: 2tBu-mmtBuDPhA2Anth), which is represented by Structural Formula (102) below, is described. Note that in 2tBu-mmtBuDPhA2Anth, the luminophore 130*b* is an anthracene ring and the protecting group 131 is a tertiary butyl (tBu) group.

[Chemical Formula 24]

(102)

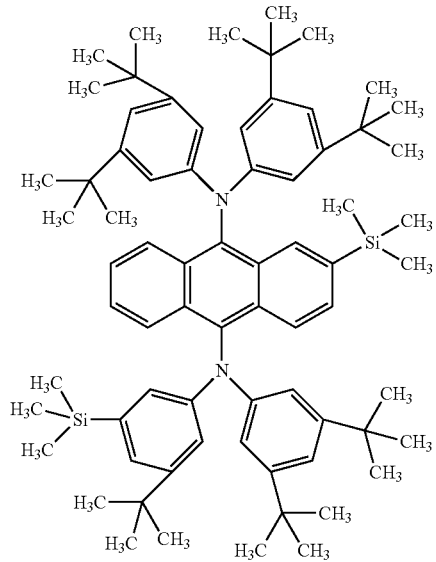

Figure 4A:
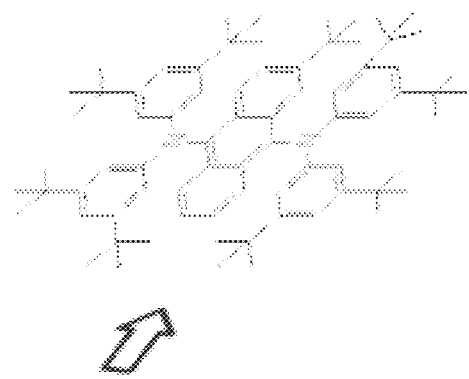
FIG. 4A shows a structural formula of a guest material used in a light-emitting layer.
Figure 4B:
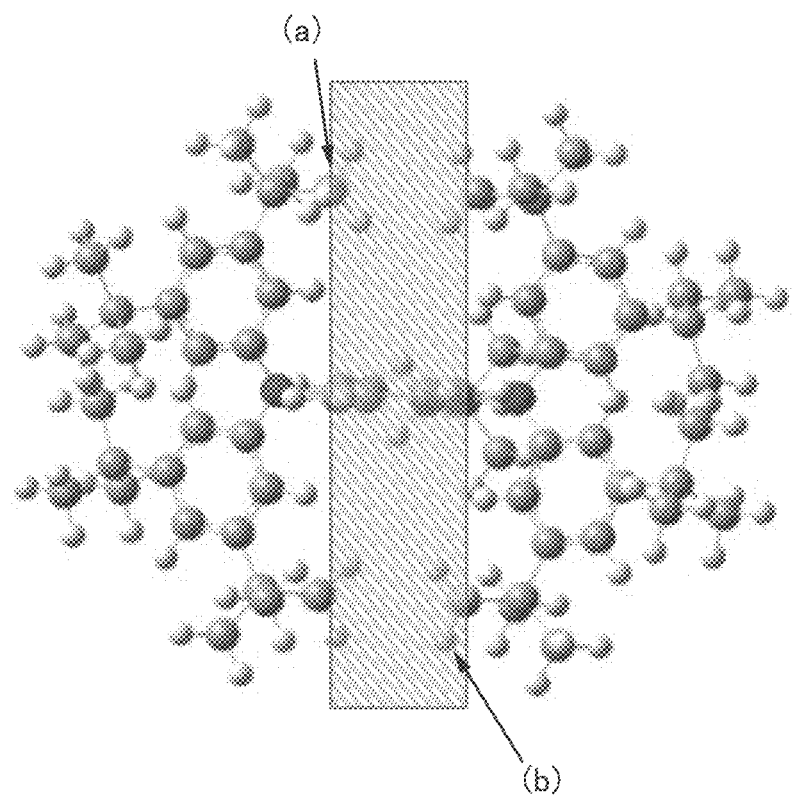
FIG. 4B shows a ball-and-stick model of the guest material used in the light-emitting layer.

FIG. 4A shows 2tBu-mmtBuDPhA2Anth. FIG. 4B shows a ball-and-stick model image of 2tBu-mmtBuDPhA2Anth that is viewed in the direction indicated by an arrow in FIG. 4A (the direction parallel to the anthracene ring plane).

The hatched portion in FIG. 4B represents an overhead portion of the anthracene ring plane, which is the luminophore 130*b*, and the overhead portion includes a region overlapping with tBu groups, which are protecting groups. For example, in FIG. 4B, an atom indicated by an arrow (a) is a carbon atom of the tBu group overlapping with the hatched portion, and an atom indicated by an arrow (b) is a hydrogen atom of the tBu group overlapping with the hatched portion. In other words, in 2tBu-mmtBuDPhA2Anth, atoms included in the protecting groups 131 are positioned over one plane of the luminophore 130*b*, and atoms included in the protecting groups 131 are also positioned over the other plane of the luminophore 130*b*. With such a structure, even in the state where the first organic compound 121 serving as a guest material is dispersed in the third organic compound 123 serving as a host material, the anthracene ring, which is the luminophore 130*b*, and the host material can be away from each other in both the horizontal direction and the vertical direction of the anthracene ring, leading to inhibition of energy transfer by the Dexter mechanism.

As for energy transfer by the Dexter mechanism, for example, when the transition related to energy transfer is transition between HOMO and LUMO, the overlap of the HOMOs of the host material and the guest material and the overlap of the LUMOs of the host material and the guest material significantly cause the Dexter mechanism. Therefore, the Dexter mechanism can be inhibited by inhibiting the overlap of the HOMOs of both of the materials and the overlap of the LUMOs thereof. In other words, the Dexter mechanism can be inhibited by increasing the distance between the skeleton and the guest material, which are related to the excited state. In the second organic compound 121, which is a fluorescent substance, the luminophore 130*b* has both HOMO and LUMO in many cases. Thus, in order to inhibit the Dexter mechanism, it is important for 2tBu-mmtBuDPhA2Anth shown in FIG. 4B to have a molecular structure in which HOMO and LUMO extending above and below the anthracene ring as the luminophore 130*b* are covered with the protecting groups 131.

Note that in the case where the luminophore 130*b* included in the first organic compound 121 is a condensed aromatic ring or a condensed heteroaromatic ring such as a pyrene ring or an anthracene ring, a transition dipole vector exists on a plane of the ring. Thus, as shown in FIG. 4B, 2tBu-mmtBuDPhA2Anth preferably includes a region overlapping with a tBu group as the protecting group 131 on the plane where the transition dipole vector is present, that is, over the plane of the anthracene ring as the luminophore 130*b*. Specifically, at least one of atoms of a plurality of protecting groups 131 (the tBu groups in FIG. 4B) is positioned over one plane of the condensed aromatic ring or the condensed heteroaromatic ring (the anthracene ring in FIG. 4B), and at least another one of the atoms of the plurality of protecting groups 131 is positioned over the other plane of the condensed aromatic ring or the condensed heteroaromatic ring.

Next, a method for synthesizing the first organic compound 121 represented by General Formula (G1) below will be described.

[Chemical Formula 25]

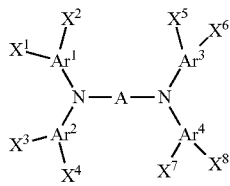

(G1)

In General Formula (G1) above, A represents a substituted or unsubstituted condensed aromatic ring having 10 to 30 carbon atoms or a substituted or unsubstituted condensed heteroaromatic ring having 10 to 30 carbon atoms, $Ar^1$ to $Ar^4$ each independently represent a substituted or unsubstituted aromatic hydrocarbon group having 6 to 13 carbon atoms, $X^1$ to $X^8$ each independently represent any one of an alkyl group having 1 to 10 carbon atoms, a substituted or unsubstituted cycloalkyl group having 3 to 10 carbon atoms, and a trialkylsilyl group having 3 to 10 carbon atoms.

The first organic compound 121 represented by General Formula (G1) above can be synthesized by, for example, Synthesis Scheme (S-1) and Synthesis Scheme (S-2) shown below.

First, as shown in Synthesis Scheme (S-1), a compound 1, a compound 2 (arylamine), and a compound 3 (arylamine) are coupled, whereby a compound 4 (diamine compound) is obtained.

[Chemical Formula 26]

(S-1)

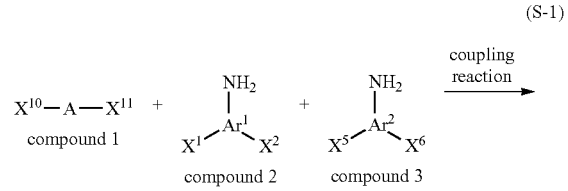

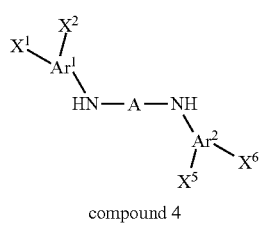

compound 4

Next, as shown in Synthesis Scheme (S-2), the compound 4 (diamine compound), the compound 5 (halogenated aryl), and the compound 6 (halogenated aryl) are coupled, whereby the first organic compound 121 represented by General Formula (G1) can be obtained.

[Chemical Formula 27]

(S-2)

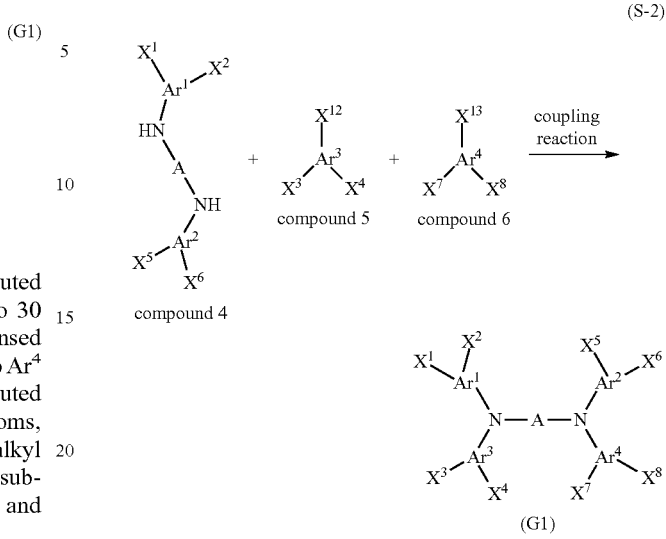

In Synthesis Schemes (S-1) and (S-2) above, A represents a substituted or unsubstituted condensed aromatic ring having 10 to 30 carbon atoms or a substituted or unsubstituted condensed heteroaromatic ring having 10 to 30 carbon atoms, $Ar^1$ to $Ar^4$ each independently represent a substituted or unsubstituted aromatic hydrocarbon group having 6 to 13 carbon atoms, $X^1$ to $X^8$ each independently represent any one of an alkyl group having 1 to 10 carbon atoms, a substituted or unsubstituted cycloalkyl group having 3 to 10 carbon atoms, and a trialkylsilyl group having 3 to 12 carbon atoms. Examples of the condensed ring or the condensed heteroaromatic ring include chrysene, phenanthrene, stilbene, acridone, phenoxazine, and phenothiazine. In particular, anthracene, pyrene, coumarin, quinacridone, perylene, tetracene, and naphthobisbenzofuran are preferable.

In the case where a Buchwald-Hartwig reaction using a palladium catalyst is performed in Synthesis Schemes (S-1) and (S-2) above, $X^{10}$ to $X^{13}$ each represent a halogen group or a triflate group, and the halogen is preferably iodine, bromine, or chlorine. In the reaction, a palladium compound such as bis(dibenzylideneacetone)palladium(0) or palladium (II) acetate and a ligand such as tri(tert-butyl)phosphine, tri(n-hexyl)phosphine, tricyclohexylphosphine, di(1-adamantyl)-n-butylphosphine, or 2-dicyclohexylphosphino-2', 6'-dimethoxy-1,1'-biphenyl can be used. In addition, an organic base such as sodium tert-butoxide, an inorganic base such as potassium carbonate, cesium carbonate, or sodium carbonate, or the like can be used. Furthermore, toluene, xylene, mesitylene, benzene, tetrahydrofuran, dioxane, or the like can be used as a solvent. Reagents that can be used in the reaction are not limited thereto.

The reaction performed in Synthesis Schemes (S-1) and (S-2) above is not limited to the Buchwald-Hartwig reaction. A Migita-Kosugi-Stille coupling reaction using an organotin compound, a coupling reaction using a Grignard reagent, an Ullmann reaction using copper or a copper compound, or the like can be used.

In the case where the compound 2 and the compound 3 have different structures in Synthesis Scheme (S-1) above, it is preferable that the compound 1 and the compound 2 be reacted first to form a coupling product and then the obtained coupling product and the compound 3 be reacted. In the case where the compound 1 is reacted with the compound 2 and the compound 3 in different stages, it is preferable that the compound 1 be a dihalogen compound and $X^{10}$ and $X^{11}$ be different halogens and selectively subjected to amination reactions one by one.

Furthermore, in the case where the compound 5 and the compound 6 have different structures in Synthesis Scheme (S-2) above, it is preferable that the compound 4 and the compound 5 be reacted first to form a coupling product and then the obtained coupling product and the compound 6 be reacted.

The above is the description of the synthesis method of General Formula (G1), which is an example of the first organic compound 121 and can be used for the light-emitting layer of the light-emitting device of one embodiment of the present invention; however, the present invention is not limited thereto and the synthesis may be performed by another synthesis method.

Embodiment 3

In this embodiment, a light-emitting device of one embodiment of the present invention will be described.
<Structure Example of Light-Emitting Device>

Figure 5A:
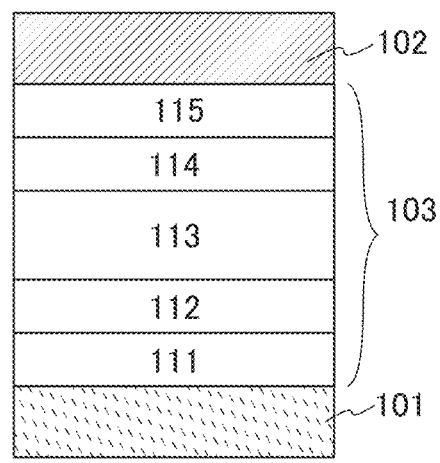
FIG. 5A and FIG. 5B are diagrams illustrating structures of light-emitting devices.

FIG. 5A shows an example of a light-emitting device including, between a pair of electrodes, an EL layer including a light-emitting layer. Specifically, the light-emitting device has a structure in which the EL layer 103 is sandwiched between the first electrode 101 and the second electrode 102. For example, in the case where the first electrode 101 serves as an anode, the EL layer 103 has a structure in which the hole-injection layer 111, the hole-transport layer 112, the light-emitting layer 113, the electron-transport layer 114, and the electron-injection layer 115 are sequentially stacked as functional layers. The light-emitting layer 113 includes a host material and a guest material; the third organic compound 123 is used as the host material; and as the guest material, the first organic compound 121, which is a material (a fluorescent substance) having a function of converting singlet excitation energy into light emission, and the second organic compound 122, which is a material (a phosphorescent substance or a TADF material) having a function of converting triplet excitation energy into light emission, are used.

Embodiments of the present invention also include light-emitting devices having other structures, for example, a light-emitting device that can be driven at a low voltage by having a structure in which a plurality of EL layers, between which a charge-generation layer is sandwiched, are provided between a pair of electrodes (a tandem structure), and a light-emitting device that has improved optical characteristics by having a micro-optical resonator (microcavity) structure between a pair of electrodes. Note that the charge-generation layer has a function of injecting electrons into one of the adjacent EL layers and injecting holes into the other of the EL layers when a voltage is applied to the first electrode 101 and the second electrode 102.

Note that at least one of the first electrode 101 and the second electrode 102 of the above light-emitting device is an electrode having a light-transmitting property (e.g., a transparent electrode or a transflective electrode). In the case where the electrode having a light-transmitting property is a transparent electrode, the visible light transmittance of the transparent electrode is 40% or higher. In the case where the electrode having a light-transmitting property is a transflective electrode, the visible light reflectance of the transflective electrode is higher than or equal to 20% and lower than or equal to 80%, preferably higher than or equal to 40% and lower than or equal to 70%. The resistivity of these electrodes is preferably $1\times10^{-2}$ Ωcm or lower.

In the case where one of the first electrode 101 and the second electrode 102 is an electrode having reflectivity (a reflective electrode) in the above light-emitting device of one embodiment of the present invention, the visible light reflectance of the electrode having reflectivity is higher than or equal to 40% and lower than or equal to 100%, preferably higher than or equal to 70% and lower than or equal to 100%. The resistivity of this electrode is preferably $1\times10^{-2}$ Ωcm or lower.

<First Electrode and Second Electrode>

As materials for forming the first electrode 101 and the second electrode 102, any of the following materials can be used in an appropriate combination as long as the functions of the electrodes described above can be fulfilled. For example, a metal, an alloy, an electrically conductive compound, and a mixture of these can be used as appropriate. Specific examples include In—Sn oxide (also referred to as ITO), In—Si—Sn oxide (also referred to as ITSO), In—Zn oxide, and In—W—Zn oxide. It is also possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use an element belonging to Group 1 or Group 2 in the periodic table, which is not listed above as an example (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

For fabrication of these electrodes, a sputtering method or a vacuum evaporation method can be used.

<Hole-Injection Layer>

The hole-injection layer 111 is a layer injecting holes from the first electrode 101 that is an anode to the EL layer 103, and is a layer containing an organic acceptor material or a material with a high hole-injection property.

The organic acceptor material is a material that allows holes to be generated in another organic compound whose HOMO level value is close to the LUMO level value of the organic acceptor material when charge separation is caused between the organic acceptor material and the organic compound. Thus, as the organic acceptor material, a compound having an electron-withdrawing group (a halogen group or a cyano group), such as a quinodimethane derivative, a chloranil derivative, or a hexaazatriphenylene derivative, can be used. For example, 7,7,8,8-tetracyano-2,3,5,6-tetrafluoroquinodimethane (abbreviation: $F_4$-TCNQ), 3,6-difluoro-2,5,7,7,8,8-hexacyanoquinodimethane, chloranil, 2,3,6,7,10,11-hexacyano-1,4,5,8,9,12-hexaazatriphenylene (abbreviation: HAT-CN), or 1,3,4,5,7,8-hexafluorotetracyano-naphthoquinodimethane (abbreviation: F6-TCNNQ) can be used. Among organic acceptor materials, HAT-CN, which has a high acceptor property and stable film quality against heat, is particularly favorable. Besides, a [3]radialene derivative has a very high electron-accepting property and thus is preferable; specifically, α,α',α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], α,α',α"-1,2,3-cyclopropanetriylidenetris[2,3,4,5,6-pentafluorobenzeneacetonitrile], or the like can be used.

Examples of the material with a high hole-injection property include transition metal oxides such as molybdenum oxide, vanadium oxide, ruthenium oxide, tungsten oxide, and manganese oxide. It is also possible to use a phthalocyanine-based compound such as phthalocyanine (abbreviation: H$_2$Pc) or copper phthalocyanine (abbreviation: CuPc), or the like.

In addition to the above materials, it is also possible to use an aromatic amine compound, which is a low molecular compound, such as 4,4',4''-tris(N,N'-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N-(3-methylphenyl)-N-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), or 3-[N-(1-naphthyl)-N-(9-phenylcarbazol-3-yl)amino]-9-phenylcarbazole (abbreviation: PCzPCN1).

It is also possible to use a high molecular compound (an oligomer, a dendrimer, a polymer, or the like) such as poly(N-vinylcarbazole) (abbreviation: PVK), poly(4-vinyltriphenylamine) (abbreviation: PVTPA), poly[N-(4-{NM-[4-(4-diphenylamino)phenyl]phenyl-N-phenylamino}phenyl)methacrylamide] (abbreviation: PTPDMA), or poly[N,N'-bis(4-butylphenyl)-N,N'-bis(phenyl)benzidine] (abbreviation: Poly-TPD). Alternatively, it is also possible to use a high molecular compound to which acid is added, such as poly(3,4-ethylenedioxythiophene)/poly(styrenesulfonic acid) (abbreviation: PEDOT/PSS) or polyaniline/poly(styrenesulfonic acid) (PAni/PSS).

Alternatively, as the material having a high hole-injection property, a composite material containing a hole-transport material and an acceptor material (electron-accepting material) can be used. In this case, the acceptor material extracts electrons from a hole-transport material, so that holes are generated in the hole-injection layer 111 and the holes are injected into the light-emitting layer 113 through the hole-transport layer 112. Note that the hole-injection layer 111 may be formed as a single layer made of a composite material containing a hole-transport material and an acceptor material (electron-accepting material), or may be formed by stacking a layer containing a hole-transport material and a layer containing an acceptor material (electron-accepting material).

As the hole-transport material, a substance having a hole mobility of greater than or equal to $1 \times 10^{-6}$ cm$^2$/Vs is preferable. Note that other substances can be used as long as they have a property of transporting more holes than electrons.

As the hole-transport material, materials having a high hole-transport property, such as a π-electron rich heteroaromatic compound (e.g., a carbazole derivative and a furan derivative) and an aromatic amine (a compound having an aromatic amine skeleton), are preferable.

Examples of the above carbazole derivative (a compound having a carbazole skeleton) include a bicarbazole derivative (e.g., a 3,3'-bicarbazole derivative) and an aromatic amine having a carbazolyl group.

Specific examples of the bicarbazole derivative (e.g., a 3,3'-bicarbazole derivative) include 3,3'-bis(9-phenyl-9H-carbazole) (abbreviation: PCCP), 9,9'-bis(1,1'-biphenyl-4-yl)-3,3'-bi-9H-carbazole, 9,9'-bis(1,1'-biphenyl-3-yl)-3,3'-bi-9H-carbazole, 9-(1,1'-biphenyl-3-yl)-9'-(1,1'-biphenyl-4-yl)-9H,9'H-3,3'-bicarbazole (abbreviation: mBPCCBP), and 9-(2-naphthyl)-9'-phenyl-9H,9'H-3,3'-bicarbazole (abbreviation: PNCCP).

Specific examples of the above aromatic amine having a carbazolyl group include 4-phenyl-4'-(9-phenyl-9H-carbazol-3-yl)triphenylamine (abbreviation: PCBA1BP), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N,N'-triphenyl-N,N,N'-tris(9-phenylcarbazol-3-yl)benzene-1,3,5-triamine (abbreviation: PCA3B), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 2-[N-(9-phenylcarbazol-3-yl)-N-phenylamino]spiro-9,9'-bifluorene (abbreviation: PCASF), N-[4-(9H-carbazol-9-yl)phenyl]-N-(4-phenyl)phenylaniline (abbreviation: YGA1BP), N,N'-bis[4-(carbazol-9-yl)phenyl]-N,N'-diphenyl-9,9-dimethylfluorene-2,7-diamine (abbreviation: YGA2F), and 4,4',4''-tris(carbazol-9-yl)triphenylamine (abbreviation: TCTA).

In addition to the above, other examples of the carbazole derivative include 3-[4-(9-phenanthryl)-phenyl]-9-phenyl-9H-carbazole (abbreviation: PCPPn), 3-[4-(1-naphthyl)-phenyl]-9-phenyl-9H-carbazole (abbreviation: PCPN), 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA).

Specific examples of the above furan derivative (a compound having a furan skeleton) include compounds having a thiophene skeleton, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV), 4,4',4''-(benzene-1,3,5-triyl)tri(dibenzofuran) (abbreviation: DBF3P-II), and 4-{3-[3-(9-phenyl-9H-fluoren-9-yl)phenyl]phenyl}dibenzofuran (abbreviation: mmDBFFLBi-II).

Specific examples of the above aromatic amine include 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[NV-phenyl-N-(9,9-dimethyl-9H-fluoren-2-yl) amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 2,7-bis[N-(4-diphenylaminophenyl)-N-phenylamino]-spiro-9,9'-bifluorene (abbreviation: DPA2SF), 4,4',4"-tris[N-(1-naphthyl)-N-phenylamino]triphenylamine (abbreviation: 1'-TNATA), 4,4',4"-tris(N,N'-diphenylamino)triphenylamine (abbreviation: TDATA), 4,4',4"-tris[N-(3-methylphenyl)-N-phenylamino]triphenylamine (abbreviation: m-MTDATA), N,N'-di(p-tolyl)-N, N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

As the hole-transport material, a high molecular compound such as poly(N-vinylcarbazole) (abbreviation: PVK), poly(4-vinyltriphenylamine) (abbreviation: PVTPA), poly[N-(4-{V-[4-(4-diphenylamino)phenyl]phenyl-N-phenylamino}phenyl)methacrylamide](abbreviation: PTPDMA), or poly[N,N'-bis(4-butylphenyl)-N,N'-bis(phenyl)benzidine](abbreviation: Poly-TPD) can also be used.

Note that the hole-transport material is not limited to the above, and one of or a combination of various known materials may be used as the hole-transport material.

As the acceptor material used for the hole-injection layer 111, an oxide of a metal belonging to any of Group 4 to Group 8 of the periodic table can be used. As specific examples, molybdenum oxide, vanadium oxide, niobium oxide, tantalum oxide, chromium oxide, tungsten oxide, manganese oxide, and rhenium oxide can be given. Among these, molybdenum oxide is particularly preferable since it is stable in the air, has a low hygroscopic property, and is easy to handle. It is also possible to use any of the above-described organic acceptors.

Note that the hole-injection layer 111 can be formed by any of various known deposition methods, and can be formed by a vacuum evaporation method, for example.

<Hole-Transport Layer>

The hole-transport layer 112 is a layer transporting holes, which are injected from the first electrode 101 through the hole-injection layer 111, to the light-emitting layer 113. Note that the hole-transport layer 112 is a layer containing a hole-transport material. Thus, for the hole-transport layer 112, a hole-transport material that can be used for the hole-injection layer 111 can be used.

Note that in the light-emitting device of one embodiment of the present invention, the same organic compound is preferably used for the hole-transport layer 112 and the light-emitting layer 113. This is because the use of the same organic compounds for the hole-transport layer 112 and the light-emitting layer 113 allows efficient hole transport from the hole-transport layer 112 to the light-emitting layer 113.

<Light-Emitting Layer>

The light-emitting layer 113 is a layer containing a light-emitting substance. In the light-emitting device of one embodiment of the present invention, the light-emitting layer 113 includes a host material and a guest material; the third organic compound 123 is used as the host material; and as the guest material, the first organic compound 121, which is a material (a fluorescent substance) having a function of converting singlet excitation energy into light emission, and the second organic compound 122, which is a material (a phosphorescent substance or a TADF material) having a function of converting triplet excitation energy into light emission, are used. The light-emitting substance that can be used for the light-emitting layer 113 is not particularly limited as long as the above condition is satisfied, and it is possible to use a substance that exhibits emission color of blue, purple, bluish purple, green, yellowish green, yellow, orange, red, or the like can be used as appropriate.

Note that a plurality of kinds of organic compounds may be used as host materials used for the light-emitting layer 113; alternatively, an exciplex formed by these compounds may be used. A substance that has an energy gap larger than that of the first organic compound 121 and that of the second organic compound 122, which are used as the guest material, is preferably used as the third organic compound 123 used as the host material. It is preferable that the lowest singlet excitation energy level (S1 level) of the third organic compound 123 be higher than the S1 level of the first organic compound 121 and that the lowest triplet excitation energy level (T1 level) of the third organic compound 123 be higher than the T1 level of the first organic compound 121. Furthermore, the lowest triplet excitation energy level (T1 level) of the third organic compound 123 is preferably higher than the T1 level of the second organic compound 122.

An organic compound such as the aforementioned hole-transport material that can be used in the hole-transport layer 112 or an electron-transport material described later that can be used in the electron-transport layer 114, or an exciplex formed by a plurality of kinds of organic compounds can be used as the one or more kinds of organic compounds used as the host material as long as requirements for the host material used in the light-emitting layer are satisfied. An exciplex (also referred to as Exciplex) whose excited state is formed by a plurality of kinds of organic compounds has an extremely small difference between the S1 level and the T1 level and functions as a TADF material that can convert triplet excitation energy into singlet excitation energy. As a combination of the plurality of kinds of organic compounds forming an exciplex, for example, it is preferable that one have a π-electron deficient heteroaromatic ring and the other have a π-electron rich heteroaromatic ring. A phosphorescent substance such as an iridium-, rhodium-, or platinum-based organometallic complex or a metal complex may be used as one of the combination forming an exciplex.

Note that the first organic compound 121 and the second organic compound 122, which are used as the guest materials of the light-emitting layer 113, preferably exhibit different emission colors. Alternatively, complementary emission colors may be combined to obtain white light emission.

The material described in Embodiment 2 can be used as the first organic compound 121, which is the first guest material of the light-emitting layer 113 and has a function of converting singlet excitation energy into light emission, in the combination satisfying requirements for the guest materials used in the light-emitting layer. Examples of the second organic compound 122, which is the second guest material of the light-emitting layer 113 and has a function of converting triplet excitation energy into light emission, include a substance that emits phosphorescence (a phosphorescent substance) and a thermally activated delayed fluorescence (TADF) material that exhibits thermally activated delayed fluorescence. Any of these materials can be used similarly in the combination satisfying the requirements for the guest materials used in the light-emitting layer. The lowest singlet excitation energy level (S1 level) of the first organic compound 121 is higher than the T1 level of the second organic compound 122. That is, a peak wavelength in the emission spectrum of light emitted from the second organic compound 122 is longer than that in the emission spectrum of light emitted from the first organic compound 121.

A phosphorescent substance refers to a compound that exhibits phosphorescence but does not exhibit fluorescence at a temperature higher than or equal to low temperatures (e.g., 77 K) and lower than or equal to room temperature (i.e., higher than or equal to 77 K and lower than or equal to 313 K). The phosphorescent substance preferably contains a metal element with large spin-orbit interaction, and can be an organometallic complex, a metal complex (platinum complex), a rare earth metal complex, or the like. Specifically, a transition metal element is preferable and it is particularly preferable that a platinum group element (ruthenium (Ru), rhodium (Rh), palladium (Pd), osmium (Os), iridium (Ir), or platinum (Pt)), especially iridium, be contained, in which case the transition probability relating to direct transition between the singlet ground state and the triplet excited state can be increased.

As a phosphorescent substance that emits blue or green light and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); organometallic complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)); and the like can be given.

As a phosphorescent substance that exhibits green or yellow and whose emission spectrum has a peak wavelength at greater than or equal to 495 nm and less than or equal to 590 nm, the following substances can be given.

For example, organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(t-Buppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-κN3]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), bis(2-phenylquinolinato-N,C$^{2'}$)iridium(III) acetylacetonate (abbreviation: [Ir(pq)$_2$(acac)]), bis[2-(2-pyridinyl-κN)phenyl-κC][2-(4-phenyl-2-pyridinyl-κN)phenyl-κC]iridium(III) (abbreviation: [Ir(ppy)$_2$(4dppy)]), and bis[2-(2-pyridinyl-κN)phenyl-KC][2-(4-methyl-5-phenyl-2-pyridinyl-N)phenyl-κC]; organometallic complexes such as bis(2,4-diphenyl-1,3-oxazolato-N,C$^2$)iridium(III) acetylacetonate (abbreviation: [Ir(dpo)$_2$(acac)]), bis{2-[4'-(perfluorophenyl)phenyl]pyridinato-N,C$^{2'}$}iridium(III) acetylacetonate (abbreviation: [Ir(p-PF-ph)$_2$(acac)]), and bis(2-phenylbenzothiazolato-N,C$^2$)iridium(III) acetylacetonate (abbreviation: [Ir(bt)$_2$(acac)]); and rare earth metal complexes such as tris(acetylacetonato)(monophenanthroline)terbium(III) (abbreviation: [Tb(acac)$_3$(Phen)]) can be given.

As a phosphorescent substance that exhibits yellow or red and whose emission spectrum has a peak wavelength at greater than or equal to 570 nm and less than or equal to 750 nm, the following substances can be given.

For example, organometallic complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and (dipivaloylmethanato)bis[4,6-di(naphthalen-1-yl)pyrimidinato]iridium(III) (abbreviation: [Ir(dlnpm)$_2$(dpm)]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), bis{4,6-dimethyl-2-[3-(3,5-dimethylphenyl)-5-phenyl-2-pyrazinyl-κN]phenyl-κC}(2,6-dimethyl-3,5- heptanedionato-κ²O,O')iridium(III) (abbreviation: [Ir(dmdppr-P)₂(dibm)]), bis{4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ²O, O')iridium(III) (abbreviation: [Ir(dmdppr-dmCP)₂(dpm)]), bis[2-[5-(2,6-dimethylphenyl)-3-(3,5-dimethylphenyl)-2-pyrazinyl-κN]-4,6-dimethylphenyl-κC](2,2',6,6'-tetramethyl-3,5-heptadionato-κ²O,O')iridium(III) (abbreviation: [Ir(dmdppr-dmp)₂(dpm)]), (acetylacetonato)bis[2-methyl-3-phenylquinoxalinato-N,C²']iridium(III) (abbreviation: [Ir(mpq)₂(acac)]), (acetylacetonato)bis(2,3-diphenylquinoxalinato-N,C²')iridium(III) (abbreviation: [Ir(dpq)₂(acac)]), and (acetylacetonato)bis[2,3-bis(4-fluorophenyl)quinoxalinato]iridium(III) (abbreviation: [Ir(Fdpq)₂(acac)]); organometallic complexes having a pyridine skeleton, such as tris(1-phenylisoquinolinato-N,C²')iridium(III) (abbreviation: [Ir(piq)₃]), bis(1-phenylisoquinolinato-N,C²')iridium(III) acetylacetonate (abbreviation: [Ir(piq)₂(acac)]), and bis[4,6-dimethyl-2-(2-quinolinyl-κN)phenyl-κC](2,4-pentanedionato-κ²O,O')iridium(III) (abbreviation: [Ir(dmpqn)₂(acac)]); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1,3-propanedionato)(monophenanthroline)europium(III) (abbreviation: [Eu(DBM)₃(Phen)]) and tris[1-(2-thenoyl)-3,3,3-trifluoroacetonato](monophenanthroline)europium(III) (abbreviation: [Eu(TTA)₃(Phen)]) can be given.

Any of materials shown below can be used as the TADF material. The TADF material refers to a material that has a small difference (preferably, less than or equal to 0.2 eV) between the S1 level and the T1 level, can up-convert triplet excited state into singlet excited state (reverse intersystem crossing) using a little thermal energy, and efficiently exhibits light emission (fluorescence) from the singlet excited state. The thermally activated delayed fluorescence is efficiently obtained under the condition where the difference in energy between the triplet excited level and the singlet excited level is greater than or equal to 0 eV and less than or equal to 0.2 eV, preferably greater than or equal to 0 eV and less than or equal to 0.1 eV. Delayed fluorescence by the TADF material refers to light emission having a spectrum similar to that of normal fluorescence and an extremely long lifetime. The lifetime is $1\times10^{-6}$ seconds or longer, preferably $1\times10^{-3}$ seconds or longer.

Examples of the TADF material include fullerene, a derivative thereof, an acridine derivative such as proflavine, and eosin. Other examples include a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: SnF₂(Proto IX)), a mesoporphyrin-tin fluoride complex (abbreviation: SnF₂(Meso IX)), a hematoporphyrin-tin fluoride complex (abbreviation: SnF₂(Hemato IX)), a coproporphyrin tetramethyl ester-tin fluoride complex (abbreviation: SnF₂(Copro III-4Me)), an octaethylporphyrin-tin fluoride complex (abbreviation: SnF₂(OEP)), an etioporphyrin-tin fluoride complex (abbreviation: SnF₂(Etio I)), and an octaethylporphyrin-platinum chloride complex (abbreviation: PtCl₂OEP).

[Chemical Formula 28]

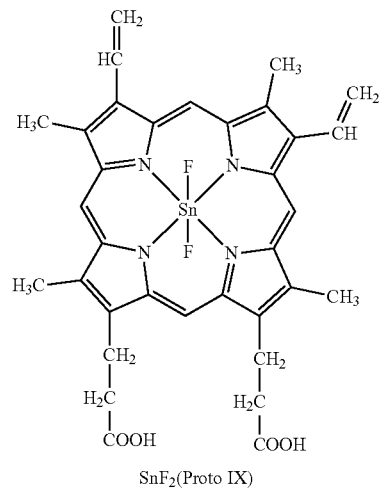

SnF₂(Proto IX)

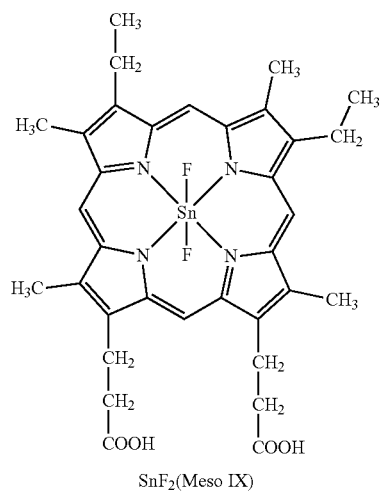

SnF₂(Meso IX)

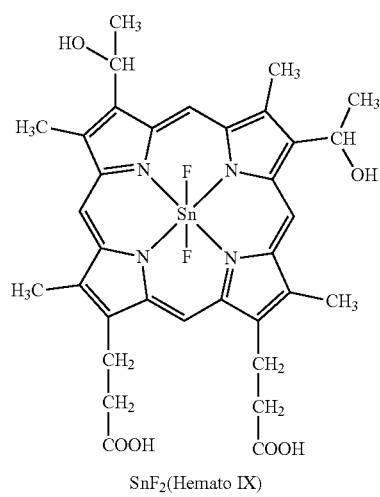

SnF₂(Hemato IX)

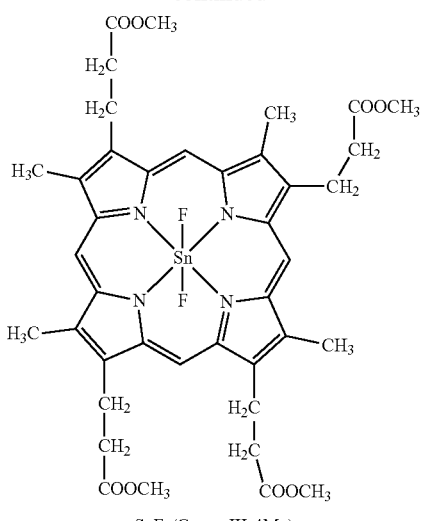

SnF₂(Copro III-4Me)

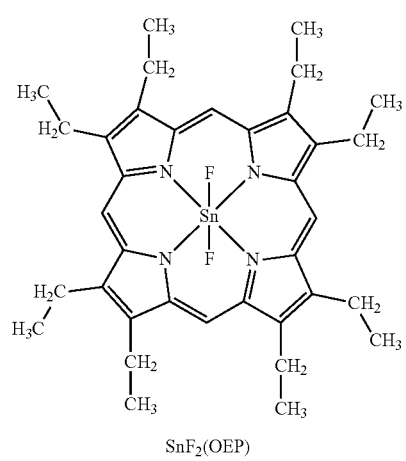

SnF₂(OEP)

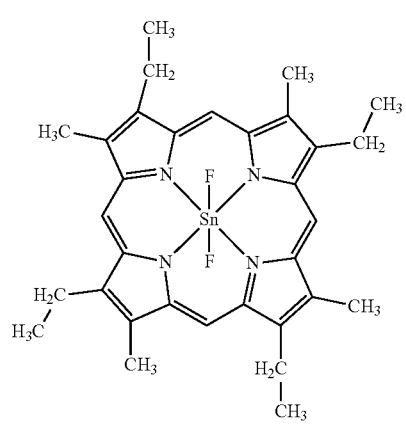

SnF₂(Etio I)

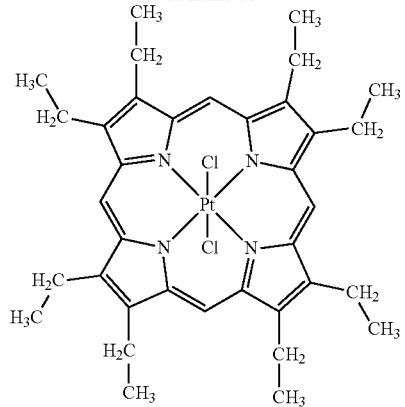

PtCl₂OEP

Alternatively, a heterocyclic compound having a π-electron rich heteroaromatic ring and a π-electron deficient heteroaromatic ring, such as 2-(biphenyl-4-yl)-4,6-bis(12-phenylindolo[2,3-α]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), 10-phenyl-10H,10'H-spiro[acridin-9,9'-anthracen]-10'-one (abbreviation: ACRSA), 4-(9'-phenyl-3,3'-bi-9H-carbazol-9-yl)benzofuro[3,2-d]pyrimidine (abbreviation: 4PCCzBfpm), 4-[4-(9'-phenyl-3,3'-bi-9H-carbazol-9-yl)phenyl]benzofuro[3,2-d]pyrimidine (abbreviation: 4PCCzPBfpm), and 9-[3-(4,6-diphenyl-1,3,5-triazin-2-yl)phenyl]-9'-phenyl-2,3'-bi-9H-carbazole (abbreviation: mPCCzPTzn-02), may be used.

Note that a substance in which a π-electron rich heteroaromatic ring is directly bonded to a π-electron deficient heteroaromatic ring is particularly preferable because both the donor property of the π-electron rich heteroaromatic ring and the acceptor property of the π-electron deficient heteroaromatic ring are improved and the energy difference between the singlet excited state and the triplet excited state becomes small.

[Chemical Formula 29]

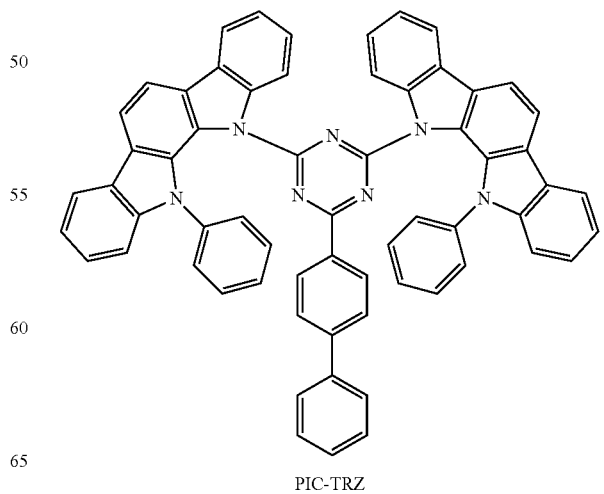

PIC-TRZ

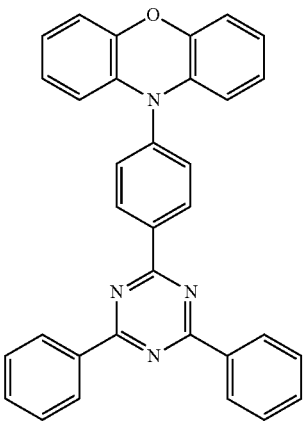
PXZ-TRZ
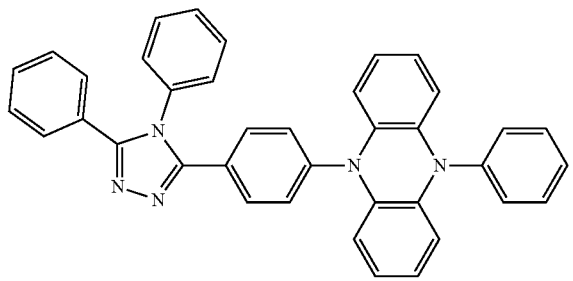
PPZ-3TPT
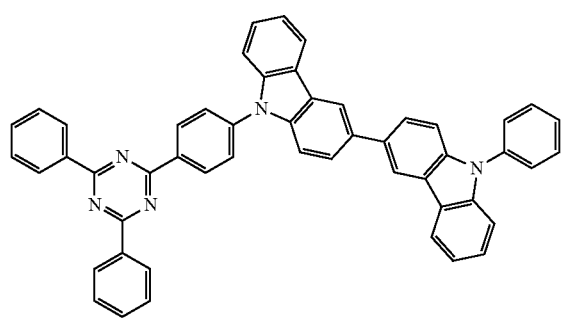
PCCzPTzn
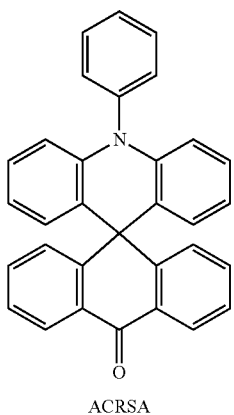
ACRSA
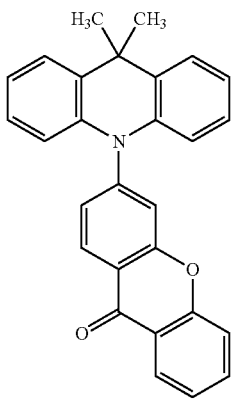
ACRXTN
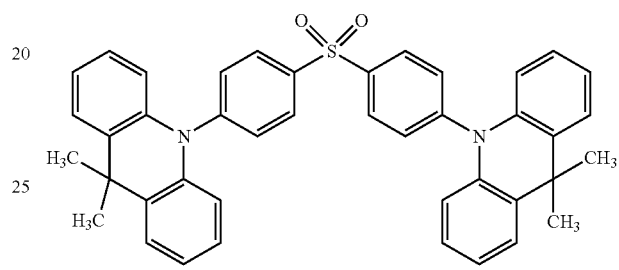
DMAC-DPS
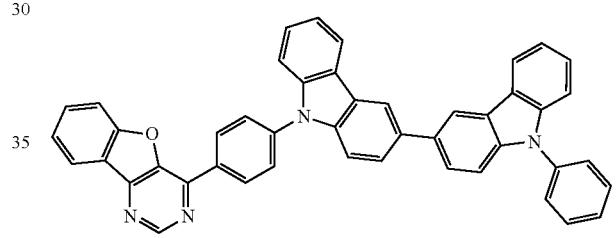
4PCCzPBfpm
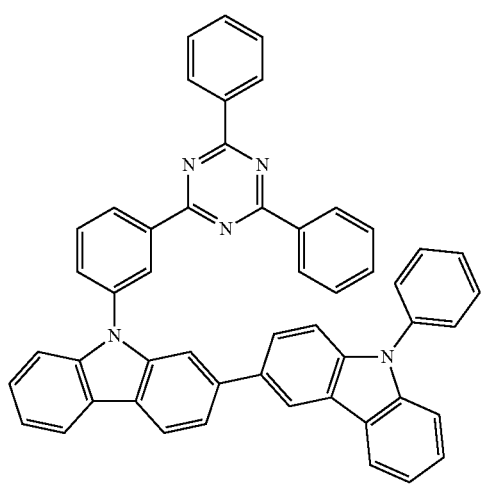
mPCCzPTzn-02

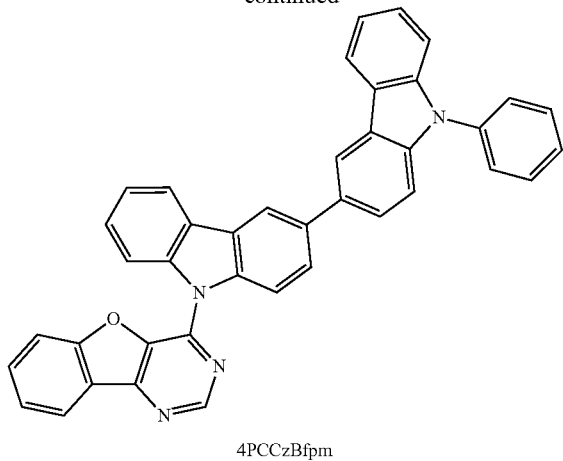

4PCCzBfpm

As the second organic compound 122, which is the material having a function of converting triplet excitation energy into light emission, a nanostructure of a transition metal compound having a perovskite structure is also given in addition to the above. In particular, a nanostructure of a metal-halide perovskite material is preferable. The nanostructure is preferably a nanoparticle or a nanorod.

Other than the above, the following substances emitting fluorescence (fluorescent substances) can be given as the light-emitting substance that can be used for the light-emitting layer 113 and convert singlet excitation energy into light emission. Examples include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of pyrene derivatives include N,N'-bis(3-methylphenyl)-N,N'-bis[3-(9-phenyl-9H-fluoren-9-yl)phenyl]pyrene-1,6-diamine (abbreviation: 1,6mMemFLPAPm), N,N'-diphenyl-N,N'-bis[4-(9-phenyl-9H-fluoren-9-yl)phenyl]pyrene-1,6-diamine (abbreviation: 1,6FLPAPm), N,N'-bis(dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis[(N-phenylbenzo[b]naphtho[1,2-d]furan)-6-amine] (abbreviation: 1,6BnfAPm), N,N'-(pyrene-1,6-diyl)bis[(N-phenylbenzo[b]naphtho[1,2-d]furan)-8-amine] (abbreviation: 1,6BnfAPrn-02), and N,N'-(pyrene-1,6-diyl)bis[(6,N-diphenylbenzo[b]naphtho[1,2-d]furan)-8-amine] (abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra-tert-butylperylene (abbreviation: TBP), N,N'-(2-tert-butylanthracene-9,10-diyldi-4,1-phenylene)bis[N,N,N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), or the like.

Examples of the third organic compound 123, which is the host material of the light-emitting layer 113, include condensed polycyclic aromatic compounds such as an anthracene derivative, a tetracene derivative, a phenanthrene derivative, a pyrene derivative, a chrysene derivative, and a dibenzo[g,p]chrysene derivative.

Specific examples of the above include 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), 3-[4-(1-naphthyl)phenyl]-9-phenyl-9H-carbazole (abbreviation: PCPN), 9,10-diphenylanthracene (abbreviation: DPAnth), N,N'-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenylchrysene, N,N,N',N',N'',N'',N''',N'''-octaphenyldibenzo[g,p]rysene-2,7,10,15-tetraamine (abbreviation: DBC1), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)-biphenyl-4'-yl}-anthracene (abbreviation: FLPPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), 5,12-diphenyltetracene, and 5,12-bis(biphenyl-2-yl)tetracene.

In addition, examples of the third organic compound 123, which is the host material of the light-emitting layer 113, include an aromatic amine, a carbazole derivative, a dibenzothiophene derivative, a dibenzofuran derivative, a zinc- or aluminum-based metal complex, an oxadiazole derivative, a triazole derivative, a benzimidazole derivative, a quinoxaline derivative, a dibenzoquinoxaline derivative, a pyrimidine derivative, a pyrazine derivative, a triazine derivative, a pyridine derivative, a bipyridine derivative, and a phenanthroline derivative.

Specific examples include triazole derivatives such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), and 3-(4-tert-butylphenyl)-4-(4-ethylphenyl)-5-(4-biphenylyl)-1,2,4-triazole (abbreviation: p-EtTAZ); and quinoxaline derivatives or dibenzoquinoxaline derivatives, such as 2,2',2''-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), 4,4'-bis(5-methylbenzoxazol-2-yl)stilbene (abbreviation:

BzOs), bathophenanthroline (abbreviation: Bphen), bathocuproine (abbreviation: BCP), 2,9-bis(naphthalen-2-yl)-4,7-diphenyl-1,10-phenanthroline (abbreviation: NBphen), 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Examples further include pyrimidine derivatives such as 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,6-bis[3-(9H-carbazol-9-yl)phenyl]pyrimidine (abbreviation: 4,6mCzP2Pm); triazine derivatives such as 2-{4-[3-(N-phenyl-9H-carbazol-3-yl)-9H-carbazol-9-yl]phenyl}-4,6-diphenyl-1,3,5-triazine (abbreviation: PCCzPTzn); triazine derivatives such as 9-[3-(4,6-diphenyl-1,3,5-triazin-2-yl)phenyl]-9'-phenyl-2,3'-bi-9H-carbazole (abbreviation: mPCCzPTzn-02); and pyridine derivatives such as 3,5-bis[3-(9H-carbazol-9-yl)phenyl]pyridine (abbreviation: 35DCzPPy), and 1,3,5-tri[3-(3-pyridyl)phenyl]benzene (abbreviation: TmPyPB).

Furthermore, a high molecular compound such as poly (2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used.

<Electron-Transport Layer>

The electron-transport layer 114 is a layer transporting electrons, which are injected from the second electrode 102 through the electron-injection layer 115 to be described later, to the light-emitting layer 113. Note that the electron-transport layer 114 is a layer containing an electron-transport material. The electron-transport material used in the electron-transport layer 114 is preferably a substance having an electron mobility of greater than or equal to $1\times10^{-6}$ cm$^2$/Vs. Note that other substances can be used as long as they have a property of transporting more electrons than holes. Electron-transport layers (114, 114a, and 114b) each function even with a single-layer structure, but can improve the device characteristics when having a stacked-layer structure of two or more layers as needed.

As the organic compound that can be used for the electron-transport layer 114, it is possible to use, in addition to the organic compounds having a structure in which an aromatic ring is fused to a furan ring of a furodiazine skeleton, a metal complex having a quinoline skeleton, a metal complex having a benzoquinoline skeleton, a metal complex having an oxazole skeleton, a metal complex having a thiazole skeleton, an oxadiazole derivative, a triazole derivative, an imidazole derivative, an oxazole derivative, a thiazole derivative, a phenanthroline derivative, a quinoline derivative having a quinoline ligand, a benzoquinoline derivative, a quinoxaline derivative, a dibenzoquinoxaline derivative, a pyridine derivative, a bipyridine derivative, a pyrimidine derivative, or a π-electron deficient heteroaromatic compound such as a nitrogen-containing heteroaromatic compound.

Specific examples of the electron-transport material include metal complexes having a quinoline skeleton or a benzoquinoline skeleton, such as 2-[3'-(dibenzothiophen-4-yl)biphenyl-3-yl]dibenzo[f,h]quinoxaline (abbreviation: 2mDBTBPDBq-II), 2-[3'-(dibenzothiophen-4-yl)biphenyl-3-yl]dibenzo[f,h]quinoxaline (abbreviation: 2mDBTBPDBq-II), 5-[3-(4,6-diphenyl-1,3,5-triazin-2yl)phenyl]-7,7-dimethyl-5H,7H-indeno[2,1-b]carbazole (abbreviation: mINc(II)PTzn), 4-[3-(dibenzothiophen-4-yl)phenyl]-8-(naphthalen-2-yl)-[1]benzofuro[3,2-d]pyrimidine (abbreviation: 8βN-4mDBtPBfpm), 3,8-bis[3-(dibenzothiophen-4-yl)phenyl]benzofuro[2,3-b]pyrazine (abbreviation: 3,8mDBtP2Bfpr), 4,8-bis[3-(dibenzothiophen-4-yl)phenyl]-[1]benzofuro[3,2-d]pyrimidine (abbreviation: 4,8mDBtP2Bfpm), 9-[(3'-dibenzothiophen-4-yl)biphenyl-3-yl]naphtho[1',2':4,5]furo[2,3-b]pyrazine (abbreviation: 9mDBtBPNfpr), 8-[3'-(dibenzothiophen-4-yl) (1,1'-biphenyl-3-yl)]naphtho[1',2':4,5]furo[3,2-d]pyrimidine (abbreviation: 8mDBtBPNfpm), 8-[(2,2'-binaphthalen)-6-yl]-4-[3-(dibenzothiophen-4-yl)phenyl]-[1]benzofuro[3,2-d]pyrimidine (abbreviation: 8(βN2)-4mDBtPBfpm), tris(8-quinolinolato)aluminum(III) (abbreviation: Alq$_3$), tris(4-methyl-8-quinolinolato)aluminum(III) (abbreviation: Almq$_3$), bis(10-hydroxybenzo[h]quinolinato)beryllium (abbreviation: BeBq$_2$), bis(2-methyl-8-quinolinolato) (4-phenylphenolato)aluminum(III) (abbreviation: BAlq), and bis (8-quinolinolato)zinc(II) (abbreviation: Znq), and metal complexes having an oxazole skeleton or a thiazole skeleton, such as bis[2-(2-benzoxazolyl)phenolato]zinc(II) (abbreviation: ZnPBO) and bis[2-(2-benzothiazolyl)phenolato]zinc(II) (abbreviation: ZnBTZ).

Other than the metal complexes, it is possible to use oxadiazole derivatives such as PBD, OXD-7, and CO11, triazole derivatives such as TAZ and p-EtTAZ, imidazole derivatives (including benzimidazole derivatives) such as TPBI and mDBTBIm-II, an oxazole derivative such as BzOs, phenanthroline derivatives such as Bphen, BCP, and NBphen, quinoxaline derivatives and dibenzoquinoxaline derivatives, such as 2mDBTPDBq-II, 2mDBTBPDBq-II, 2mCzBPDBq, 2CzPDBq-III, 7mDBTPDBq-II, and 6mDBTPDBq-II, pyridine derivatives such as 35DCzPPy and TmPyPB, pyrimidine derivatives such as 4,6mPnP2Pm, 4,6mDBTP2Pm-II, and 4,6mCzP2Pm, and triazine derivatives such as PCCzPTzn and mPCCzPTzn-02.

It is also possible to use high molecular compounds such as PPy, PF-Py, and PF-BPy.

<Electron-Injection Layer>

The electron-injection layer 115 is a layer for increasing the efficiency of electron injection from the cathode 102, and thus is preferably formed using a material whose LUMO level value has a small difference (0.5 eV or less) from the work function value of a material of the cathode 102. Thus, the electron-injection layer 115 can be formed using an alkali metal, an alkaline earth metal, or a compound thereof, such as lithium, cesium, lithium fluoride (LiF), cesium fluoride (CsF), calcium fluoride (CaF2), 8-(hydroxyquinolinato)lithium (abbreviation: Liq), 2-(2-pyridyl)phenolatolithium (abbreviation: LiPP), 2-(2-pyridyl)-3-pyridinolatolithium (abbreviation: LiPPy), 4-phenyl-2-(2-pyridyl)phenolatolithium (abbreviation: LiPPP), lithium oxide (LiOx), or cesium carbonate. A rare earth metal compound like erbium fluoride (ErF3) can also be used.

Figure 5B:
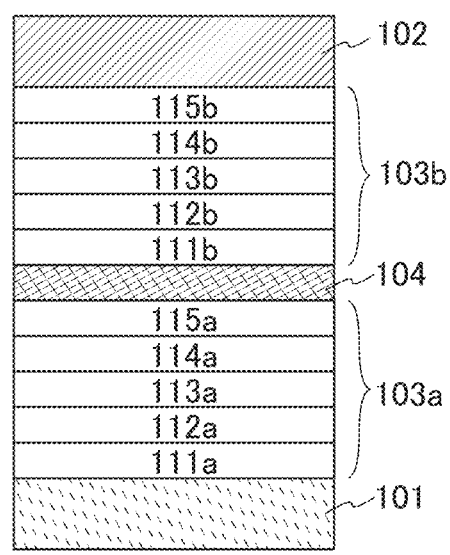

When a charge-generation layer 104 is provided between two EL layers (103a and 103b) as in the light-emitting device shown in FIG. 5B, a structure in which a plurality of EL layers are stacked between the pair of electrodes (also referred to as a tandem structure) can be employed. Note that in this embodiment, functions and materials of the hole-injection layer (111), the hole-transport layer (112), the light-emitting layer (113), the electron-transport layer (114), and the electron-injection layer (115) that are illustrated in FIG. 5A are the same as those of hole-injection layers (111a and 111b), hole-transport layers (112a and 112b), light-emitting layers (113a and 113b), the electron-transport layers (114a and 114b), and electron-injection layers (115a and 115b) that are illustrated in FIG. 5B.

<Charge-Generation Layer>

In the light-emitting device of FIG. 5B, the charge-generation layer 104 has a function of injecting electrons into the EL layer 103a and injecting holes into the EL layer 103b when voltage is applied between the first electrode (anode) 101 and the second electrode (cathode) 102. Note that the charge-generation layer 104 may have either a structure in which an electron acceptor (acceptor) is added to a hole-transport material or a structure in which an electron donor (donor) is added to an electron-transport material. Alternatively, both of these structures may be stacked. Note that forming the charge-generation layer 104 with the use of any of the above materials can inhibit an increase in drive voltage in the case where the EL layers are stacked.

In the case where the charge-generation layer 104 has a structure in which an electron acceptor is added to a hole-transport material, any of the materials described in this embodiment can be used as the hole-transport material. As the electron acceptor, 7,7,8,8-tetracyano-2,3,5,6-tetrafluoro-quinodimethane (abbreviation: $F_4$-TCNQ), chloranil, and the like can be given. Other examples include oxides of metals belonging to Group 4 to Group 8 of the periodic table. Specific examples are vanadium oxide, niobium oxide, tantalum oxide, chromium oxide, molybdenum oxide, tungsten oxide, manganese oxide, and rhenium oxide.

In the case where the charge-generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals belonging to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be used as the electron donor.

Although FIG. 5B shows the structure in which two EL layers 103 are stacked, a structure may be employed in which three or more EL layers are stacked with a charge-generation layer provided between different EL layers.

<Substrate>

The light-emitting device described in this embodiment can be formed over any of a variety of substrates. Note that the type of the substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, a laminate film, paper including a fibrous material, and a base material film.

Note that examples of the glass substrate include barium borosilicate glass, aluminoborosilicate glass, and soda lime glass. Examples of the flexible substrate, the laminate film, and the base material film include plastics typified by polyethylene terephthalate (PET), polyethylene naphthalate (PEN), and polyether sulfone (PES); a synthetic resin such as an acrylic resin; polypropylene; polyester; polyvinyl fluoride; polyvinyl chloride; polyamide; polyimide; an aramid resin; an epoxy resin; an inorganic vapor deposition film; and paper.

For fabrication of the light-emitting device in this embodiment, a vacuum process such as an evaporation method or a solution process such as a spin coating method or an ink-jet method can be used. In the case of using an evaporation method, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers (the hole-injection layers (111, 111a, and 111b), the hole-transport layers (112, 112a, and 112b), the light-emitting layers (113, 113a, 113b, and 113c), the electron-transport layers (114, 114a, and 114b), and the electron-injection layers (115, 115a, and 115b)) included in the EL layers and the charge-generation layers (104, 104a, and 104b) of the light-emitting device can be formed by an evaporation method (e.g., a vacuum evaporation method), a coating method (e.g., a dip coating method, a die coating method, a bar coating method, a spin coating method, or a spray coating method), a printing method (e.g., an ink-jet method, a screen printing (stencil) method, an offset printing (planography) method, a flexography (relief printing) method, a gravure printing method, a micro-contact printing method, or a nanoimprinting method), or the like.

Note that materials that can be used for the functional layers (the hole-injection layers (111, 111a, and 111b), the hole-transport layers (112, 112a, and 112b), the light-emitting layers (113, 113a, and 113b), the electron-transport layers (114, 114a, and 114b), and the electron-injection layers (115, 115a, and 115b)) included in the EL layers (103, 103a, and 103b) and the charge-generation layer 104 of the light-emitting device described in this embodiment are not limited to the above materials, and other materials can also be used in combination as long as the functions of the layers are fulfilled. For example, a high molecular compound (e.g., an oligomer, a dendrimer, and a polymer), a middle molecular compound (a compound between a low molecular compound and a high molecular compound with a molecular weight of 400 to 4000), or an inorganic compound (e.g., a quantum dot material) can be used. As the quantum dot material, a colloidal quantum dot material, an alloyed quantum dot material, a core-shell quantum dot material, a core quantum dot material, or the like can be used.

The structure described in this embodiment can be used in an appropriate combination with any of the structures described in the other embodiments.

Embodiment 4

Figure 6A:
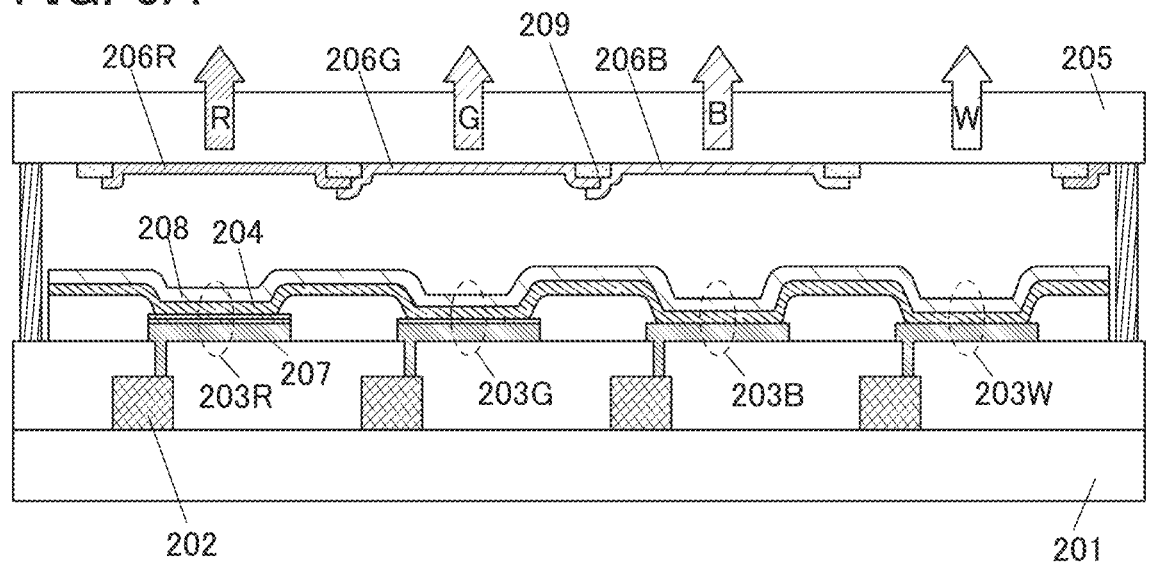
FIG. 6A, FIG. 6B, and FIG. 6C are diagrams illustrating light-emitting apparatuses.

In this embodiment, a light-emitting apparatus of one embodiment of the present invention will be described. A light-emitting apparatus shown in FIG. 6A is an active-matrix light-emitting apparatus in which transistors (FETs) 202 over a first substrate 201 are electrically connected to light-emitting devices (203R, 203G, 203B, and 203W); the light-emitting devices (203R, 203G, 203B, and 203W) include a common EL layer 204 and each have a microcavity structure where the optical path length between electrodes of each light-emitting device is adjusted according to the emission color of the light-emitting device. The light-emitting apparatus is a top-emission light-emitting apparatus in which light obtained from the EL layer 204 is emitted through color filters (206R, 206G, and 206B) formed on a second substrate 205.

In the light-emitting apparatus shown in FIG. 6A, a first electrode 207 is formed so as to function as a reflective electrode. A second electrode 208 is formed to function as a transfective electrode having both properties of transmitting and reflecting light (visible light or near-infrared light). Note that the description in the other embodiments can be referred to for electrode materials forming the first electrode 207 and the second electrode 208, and appropriate materials can be used.

Figure 6B:
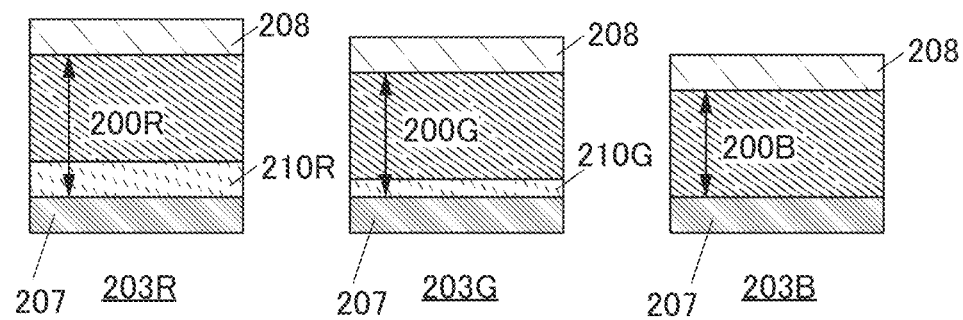

In the case where the light-emitting device 203R is a red-light-emitting device, the light-emitting device 203G is a green-light-emitting device, the light-emitting device 203B is a blue-light-emitting device, and the light-emitting device 203W is a white-light-emitting device in FIG. 6A, for example, the distance between the first electrode 207 and the second electrode 208 in the light-emitting device 203R is adjusted to have an optical path length 200R, the distance between the first electrode 207 and the second electrode 208 in the light-emitting device 203G is adjusted to have an optical path length 200G, and the distance between the first electrode 207 and the second electrode 208 in the light-emitting device 203B is adjusted to have an optical path length 200B, as shown in FIG. 6B. Note that optical adjustment can be performed in such a manner that a conductive layer 210R is stacked over the first electrode 207 in the light-emitting device 203R and a conductive layer 210G is stacked in the light-emitting device 203G as shown in FIG. 6B.

The color filters (206R, 206G, and 206B) are formed on the second substrate 205. Note that the color filter is a filter that transmits visible light in a specific wavelength range and blocks visible light in a specific wavelength range. Thus, as shown in FIG. 6A, the color filter 206R that transmits only light in the red wavelength range is provided in a position overlapping with the light-emitting device 203R, whereby red light emission can be obtained from the light-emitting device 203R. The color filter 206G that transmits only light in the green wavelength range is provided in a position overlapping with the light-emitting device 203G, whereby green light emission can be obtained from the light-emitting device 203G. The color filter 206B that transmits only light in the blue wavelength range is provided in a position overlapping with the light-emitting device 203B, whereby blue light emission can be obtained from the light-emitting device 203B. The light-emitting device 203W can emit white light without a color filter. Note that a black layer (black matrix) 209 may be provided at an end portion of one type of color filter. The color filters (206R, 206G, and 206B) and the black layer 209 may be covered with an overcoat layer using a transparent material.

Figure 6C:
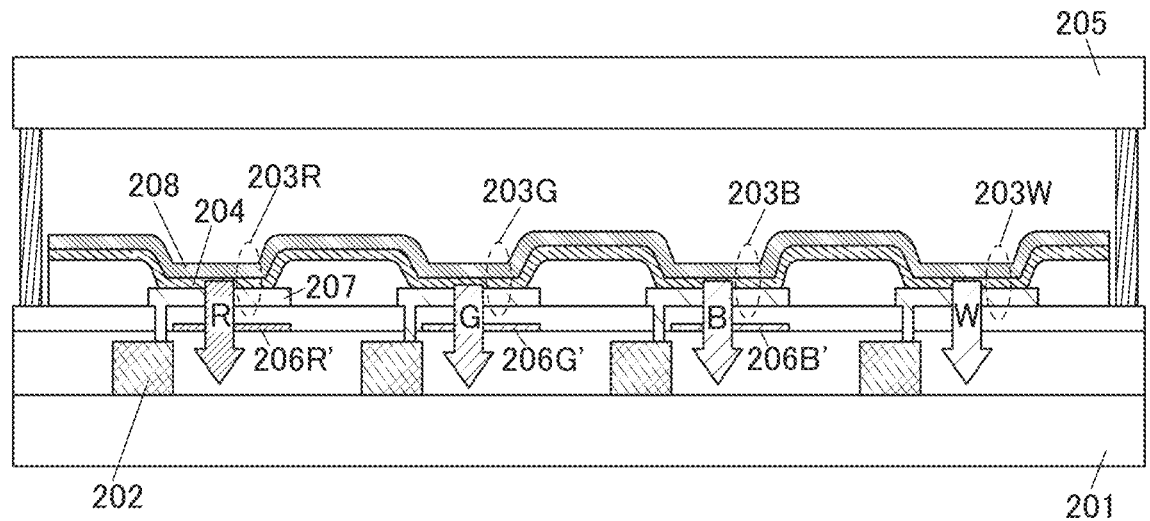

Although the light-emitting apparatus in FIG. 6A has a structure in which light is extracted from the second substrate 205 side (a top-emission structure), the light-emitting apparatus may have a structure in which light is extracted from the first substrate 201 side where the FETs 202 are formed (a bottom-emission structure) as shown in FIG. 6C. For a bottom-emission light-emitting apparatus, the first electrode 207 is formed so as to function as a transfective electrode and the second electrode 208 is formed so as to function as a reflective electrode. As the first substrate 201, a substrate having at least a light-transmitting property is used. As shown in FIG. 6C, color filters (206R', 206G', and 206B') are provided closer to the first substrate 201 than the light-emitting devices (203R, 203G, and 203B) are.

FIG. 6A shows the case where the light-emitting devices are the red-light-emitting device, the green-light-emitting device, the blue-light-emitting device, and the white-light-emitting device; however, the light-emitting devices of embodiments of the present invention are not limited to the above structures, and a yellow-light-emitting device or an orange-light-emitting device may be included. Note that the description in the other embodiments can be referred to for materials that are used for the EL layers (a light-emitting layer, a hole-injection layer, a hole-transport layer, an electron-transport layer, an electron-injection layer, a charge-generation layer, and the like) to fabricate each of the light-emitting devices, and appropriate materials can be used. In that case, a color filter needs to be appropriately selected according to the emission color of the light-emitting device.

With the above structure, a light-emitting apparatus including light-emitting devices that exhibit a plurality of emission colors can be obtained.

Note that the structure described in this embodiment can be used in an appropriate combination with any of the structures described in the other embodiments.

Embodiment 5

In this embodiment, a light-emitting apparatus of one embodiment of the present invention will be described.

The use of the device structure of the light-emitting device of one embodiment of the present invention allows fabrication of an active-matrix light-emitting apparatus and a passive-matrix light-emitting apparatus. Note that an active-matrix light-emitting apparatus has a structure including a combination of a light-emitting device and a transistor (an FET). Thus, each of a passive-matrix light-emitting apparatus and an active-matrix light-emitting apparatus is included in one embodiment of the present invention. Note that any of the light-emitting devices described in the other embodiments can be used in the light-emitting apparatus described in this embodiment.

In this embodiment, an active-matrix light-emitting apparatus will be described with reference to FIG. 7.

Figure 7A:
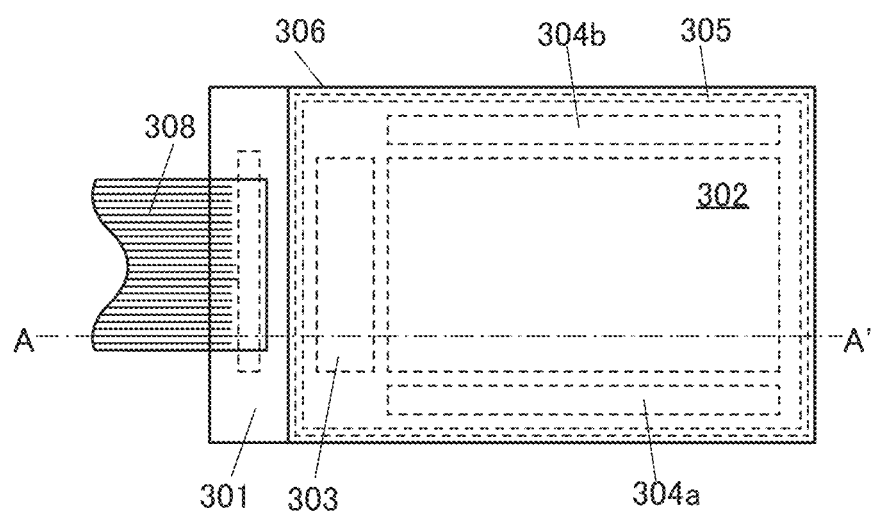
FIG. 7A is a top view illustrating a light-emitting apparatus.
Figure 7B:
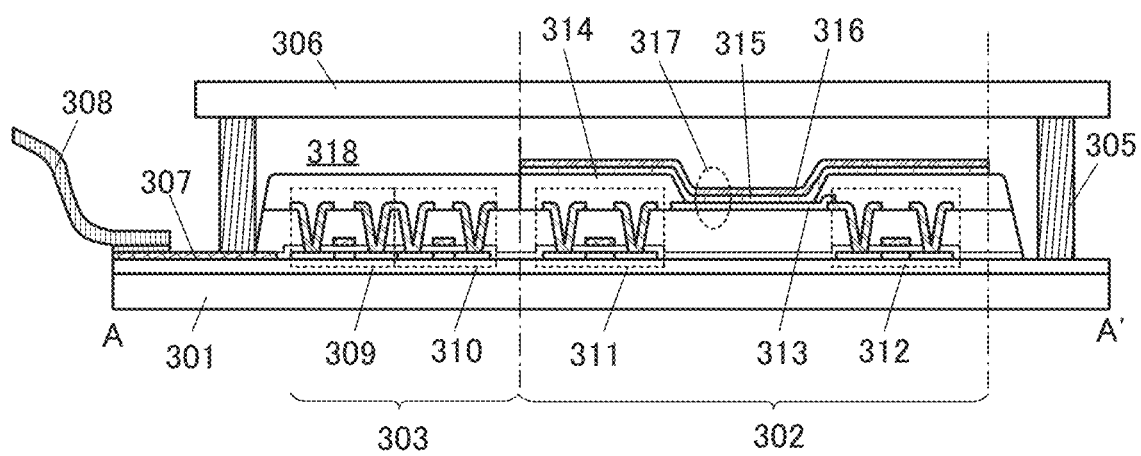
FIG. 7B is a cross-sectional view illustrating the light-emitting apparatus.

FIG. 7A is a top view showing a light-emitting apparatus, and FIG. 7B is a cross-sectional view taken along a chain line A-A' in FIG. 7A. The active-matrix light-emitting apparatus includes a pixel portion 302, a driver circuit portion (source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is electrically connected to an FPC 308 that is an external input terminal. The FPC 308 transmits a signal (e.g., a video signal, a clock signal, a start signal, and a reset signal) and a potential from the outside to the driver circuit portions (303, 304a, and 304b). The FPC 308 may be provided with a printed wiring board (PWB). Note that the light-emitting apparatus provided with an FPC or a PWB is included in the category of a light-emitting apparatus.

Next, FIG. 7B shows the cross-sectional structure.

The pixel portion 302 is made up of a plurality of pixels each including an FET (switching FET) 311, an FET (current control FET) 312, and a first electrode 313 electrically connected to the FET 312. Note that the number of FETs included in each pixel is not particularly limited and can be set appropriately as needed.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. The use of a semiconductor having crystallinity is preferable, in which case deterioration of the transistor characteristics can be inhibited.

For the semiconductor, a Group 14 element, a compound semiconductor, an oxide semiconductor, an organic semiconductor, or the like can be used, for example. Typically, a semiconductor containing silicon, a semiconductor containing gallium arsenide, an oxide semiconductor containing indium, or the like can be used.

The driver circuit portion 303 includes the FET 309 and the FET 310. The driver circuit portion 303 may be formed with a circuit including transistors having the same conductivity type (either only n-channel transistors or only p-channel transistors) or a CMOS circuit including an n-channel transistor and a p-channel transistor. Furthermore, a driver circuit may be provided outside.

An end portion of the first electrode 313 is covered with an insulator 314. For the insulator 314, an organic compound such as a negative photosensitive resin or a positive photosensitive resin (an acrylic resin), or an inorganic compound such as silicon oxide, silicon oxynitride, or silicon nitride can be used. An upper end portion or a lower end portion of the insulator 314 preferably has a curved surface with curvature. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in the other embodiments can be used for the structure of a light-emitting device 317 described in this embodiment. Although not shown here, the second electrode 316 is electrically connected to the FPC 308 that is an external input terminal.

Although the cross-sectional view in FIG. 7B shows only one light-emitting device 317, a plurality of light-emitting devices are arranged in a matrix in the pixel portion 302. Light-emitting devices from which light of three kinds of colors (R, G, and B) is obtained are selectively formed in the pixel portion 302, whereby a light-emitting apparatus capable of full-color display can be formed. In addition to the light-emitting devices from which light of three kinds of colors (R, G, and B) is obtained, for example, light-emitting devices from which light of white (W), yellow (Y), magenta (M), cyan (C), and the like is obtained may be formed. For example, when the light-emitting devices from which light of some of the above colors is obtained are added to the light-emitting devices from which light of three kinds of colors (R, G, and B) is obtained, effects such as an improvement in color purity and a reduction in power consumption can be obtained. Alternatively, a light-emitting apparatus that is capable of full-color display may be fabricated by a combination with color filters. As the kinds of color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting device 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy resin or glass frit can be used for the sealant 305. A material that transmits moisture and oxygen as little as possible is preferably used for the sealant 305. As the second substrate 306, a substrate that can be used as the first substrate 301 can be similarly used. Thus, any of the various substrates described in the other embodiments can be appropriately used. As the substrate, a glass substrate, a quartz substrate, or a plastic substrate made of FRP (Fiber-Reinforced Plastics), PVF (polyvinyl fluoride), polyester, an acrylic resin, or the like can be used. In the case where glass frit is used for the sealant, the first substrate 301 and the second substrate 306 are preferably glass substrates in terms of adhesion.

In the above manner, the active-matrix light-emitting apparatus can be obtained.

In the case where the active-matrix light-emitting apparatus is formed over a flexible substrate, the FETs and the light-emitting device may be directly formed over the flexible substrate; alternatively, the FETs and the light-emitting device may be formed over a substrate provided with a separation layer and then separated at the separation layer by application of heat, force, laser irradiation, or the like to be transferred to a flexible substrate. For the separation layer, a stack of inorganic films such as a tungsten film and a silicon oxide film, or an organic resin film of polyimide or the like can be used, for example. Examples of the flexible substrate include, in addition to a substrate where a transistor can be formed, a paper substrate, a cellophane substrate, an aramid film substrate, a polyimide film substrate, a cloth substrate (including a natural fiber (silk, cotton, and hemp), a synthetic fiber (nylon, polyurethane, and polyester), a regenerated fiber (acetate, cupro, rayon, and regenerated polyester), and the like), a leather substrate, and a rubber substrate. With the use of any of these substrates, high durability, high heat resistance, a reduction in weight, and a reduction in thickness can be achieved.

The light-emitting device included in the active-matrix light-emitting apparatus may be driven to emit light in a pulsed manner (using a frequency of kHz or MHz, for example) so that the light is used for display. The light-emitting device formed using any of the above organic compounds has excellent frequency characteristics; thus, the time for driving the light-emitting device can be shortened, and the power consumption can be reduced. Furthermore, a reduction in driving time leads to inhibition of heat generation, so that the degree of deterioration of the light-emitting device can be reduced.

Note that the structure described in this embodiment can be used in an appropriate combination with any of the structures described in the other embodiments.

Embodiment 6

In this embodiment, examples of a variety of electronic devices and an automobile completed using the light-emitting device of one embodiment of the present invention or a light-emitting apparatus including the light-emitting device of one embodiment of the present invention will be described. Note that the light-emitting apparatus can be used mainly in a display portion of the electronic device described in this embodiment.

Figure 8A:
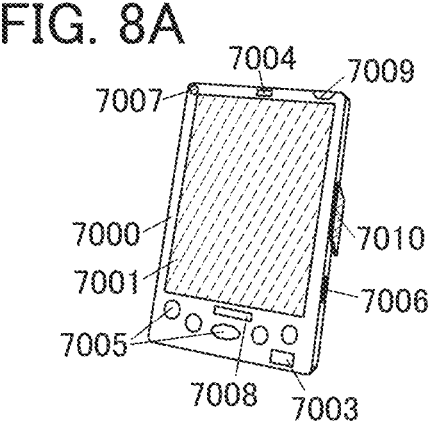
FIG. 8A is a diagram illustrating a mobile computer.
Figure 8B:
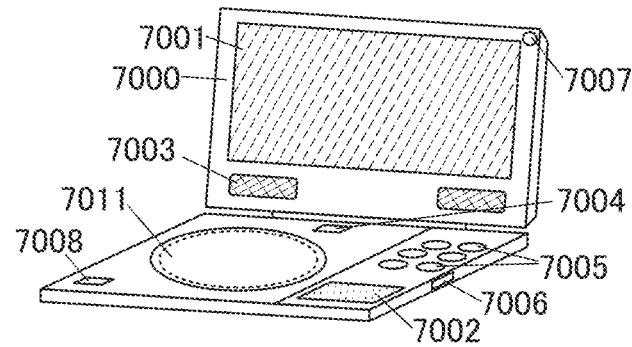
FIG. 8B is a diagram illustrating a portable image reproducing device.
Figure 8C:
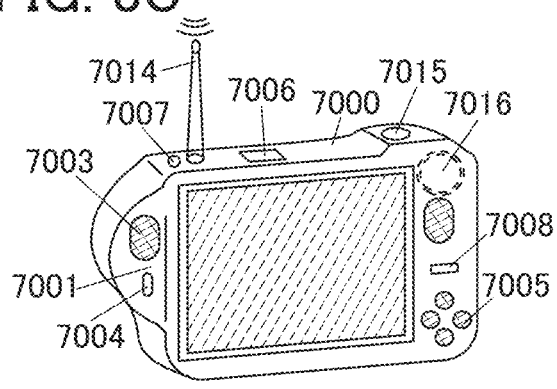
FIG. 8C is a diagram illustrating a digital camera.

Electronic devices shown in FIG. 8A to FIG. 8C can include a housing 7000, a display portion 7001, a speaker 7003, an LED lamp 7004, an operation key 7005 (including a power switch or an operation switch), a connection terminal 7006, a sensor 7007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone 7008, and the like.

FIG. 8A is a mobile computer that can include a switch 7009, an infrared port 7010, and the like in addition to the above components.

FIG. 8B is a portable image reproducing device (e.g., a DVD player) that is provided with a recording medium and can include a second display portion 7002, a recording medium reading portion 7011, and the like in addition to the above components.

FIG. 8C is a digital camera that has a television reception function and can include an antenna 7014, a shutter button 7015, an image receiving portion 7016, and the like in addition to the above components.

Figure 8D:
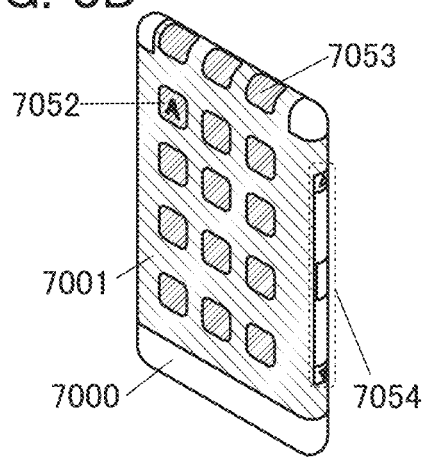
FIG. 8D is a diagram illustrating a portable information terminal.

FIG. 8D is a portable information terminal. The portable information terminal has a function of displaying information on three or more surfaces of the display portion 7001. Here, an example in which information 7052, information 7053, and information 7054 are displayed on different surfaces is shown. For example, the user can check the information 7053 displayed in a position that can be observed from above the portable information terminal, with the portable information terminal put in a breast pocket of his/her clothes. The user can see the display without taking out the portable information terminal from the pocket and decide whether to answer the call, for example.

Figure 8E:
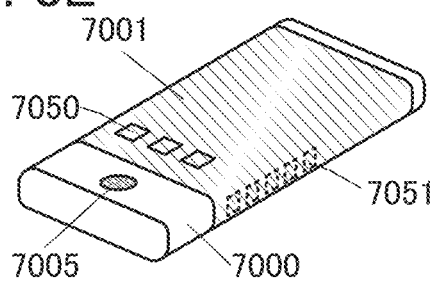
FIG. 8E is a diagram illustrating a portable information terminal.

FIG. 8E is a portable information terminal (e.g., a smartphone) that can include the display portion 7001, the operation key 7005, and the like in the housing 7000. Note that the speaker 7003, the connection terminal 7006, the sensor 7007, or the like may be provided in the portable information terminal. The portable information terminal can display text and image information on its plurality of surfaces. Here, an example in which three icons 7050 are displayed is shown. Information 7051 indicated by dashed rectangles can be displayed on another surface of the display portion 7001. Examples of the information 7051 include notification of reception of an e-mail, SNS, or an incoming call, the title and sender of an e-mail, SNS, or the like, the date, the time, remaining battery, and the reception strength of an antenna. Alternatively, the icon 7050 or the like may be displayed in the position where the information 7051 is displayed.

Figure 8F:
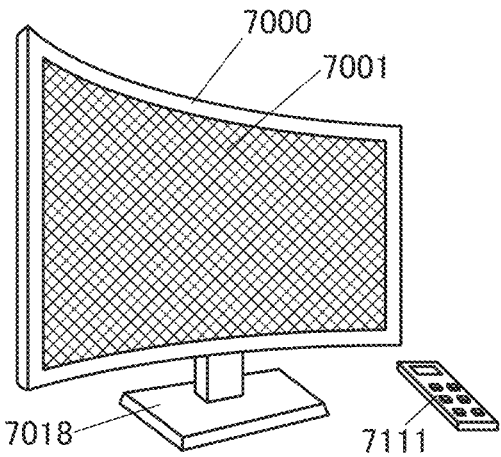
FIG. 8F is a diagram illustrating a television device.

FIG. 8F is a large-size television set (also referred to as TV or television receiver) that can include the housing 7000, the display portion 7001, and the like. Here, a structure in which the housing 7000 is supported by a stand 7018 is shown. The television set can be operated with a separate remote controller 7111 or the like. Note that the display portion 7001 may include a touch sensor, in which case the television set may be operated by touch on the display portion 7001 with a finger or the like. The remote controller 7111 may include a display portion for displaying information output from the remote controller 7111. With operation keys or a touch panel provided in the remote controller 7111, channels and volume can be controlled and images displayed on the display portion 7001 can be controlled.

The electronic devices shown in FIG. 8A to FIG. 8F can have a variety of functions. For example, they can have a function of displaying a variety of information (e.g., a still image, a moving image, and a text image) on the display portion, a touch panel function, a function of displaying a calendar, date, time, or the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion. Furthermore, the electronic device including a plurality of display portions can have a function of displaying image information mainly on one display portion while displaying text information mainly on another display portion, a function of displaying a three-dimensional image by displaying images on a plurality of display portions with a parallax taken into account, or the like. The electronic device including an image receiving portion can have a function of taking a still image, a function of taking a moving image, a function of automatically or manually correcting a taken image, a function of storing a taken image in a recording medium (an external recording medium or a recording medium incorporated in the camera), a function of displaying a taken image on the display portion, and the like. Note that functions that the electronic devices shown in FIG. 8A to FIG. 8F can have are not limited to those, and the electronic devices can have a variety of functions.

Figure 8G:
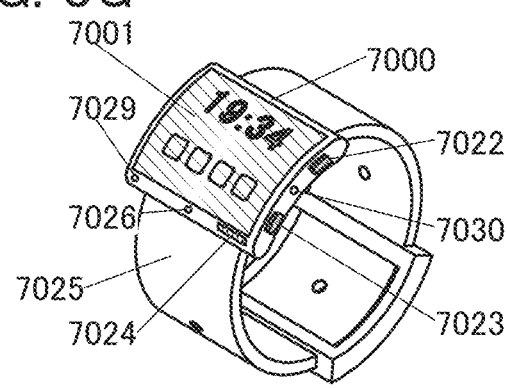
FIG. 8G is a diagram illustrating a portable information terminal.

FIG. 8G is a watch-type portable information terminal that can be used as a watch-type electronic device, for example. The watch-type portable information terminal includes the housing 7000, the display portion 7001, operation buttons 7022 and 7023, a connection terminal 7024, a band 7025, a microphone 7026, a sensor 7029, a speaker 7030, and the like. The display surface of the display portion 7001 is bent, and display can be performed along the bent display surface. The portable information terminal enables hands-free calling by mutually communicating with, for example, a headset capable of wireless communication. With the connection terminal 7024, the portable information terminal can perform mutual data transmission with another information terminal and be charged. Wireless power feeding can also be employed for the charging operation.

The display portion 7001 mounted in the housing 7000 also serving as a bezel includes a non-rectangular display region. The display portion 7001 can display an icon indicating time, another icon, and the like. The display portion 7001 may be a touch panel (an input/output device) including a touch sensor (an input device).

Note that the watch-type electronic device shown in FIG. 8G can have a variety of functions. For example, it can have a function of displaying a variety of information (e.g., a still image, a moving image, and a text image) on the display portion, a touch panel function, a function of displaying a calendar, date, time, or the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion.

Moreover, a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like can be included inside the housing 7000.

Note that the light-emitting apparatus of one embodiment of the present invention can be used in the display portions of the electronic devices described in this embodiment, enabling the electronic devices to have a long lifetime.

Figure 9A:
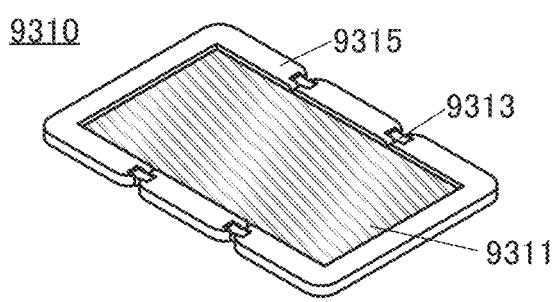
FIG. 9A, FIG. 9B, and FIG. 9C are diagrams illustrating a foldable portable information terminal.
Figure 9B:
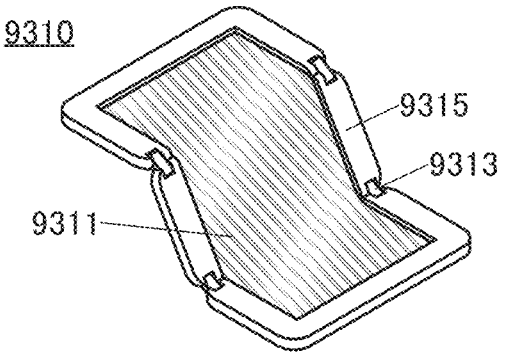
Figure 9C:
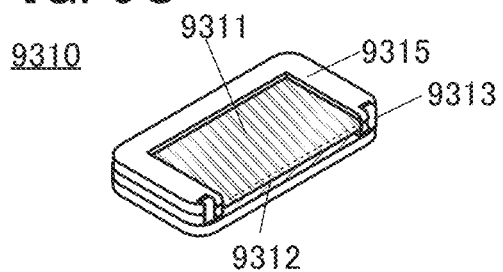

Another electronic device including the light-emitting apparatus is a foldable portable information terminal shown in FIG. 9A to FIG. 9C. FIG. 9A shows a portable information terminal 9310 that is opened. FIG. 9B shows the portable information terminal 9310 in a state in the middle of change from one of an opened state and a folded state to the other. FIG. 9C shows the portable information terminal 9310 that is folded. The portable information terminal 9310 is excellent in portability when folded, and is excellent in display browsability when opened because of a seamless large display region.

A display portion 9311 is supported by three housings 9315 joined together by hinges 9313. Note that the display portion 9311 may be a touch panel (an input/output device) including a touch sensor (an input device). By bending the display portion 9311 at a portion between two housings 9315 with the use of the hinges 9313, the portable information terminal 9310 can be reversibly changed in shape from an opened state to a folded state. The light-emitting apparatus of one embodiment of the present invention can be used in the display portion 9311. An electronic device having a long lifetime can be achieved. A display region 9312 in the display portion 9311 is a display region that is positioned at a side surface of the portable information terminal 9310 that is folded. On the display region 9312, information icons, file shortcuts of frequently used applications and programs, and the like can be displayed; hence, confirmation of information and start of an application can be smoothly performed.

Figure 10A:
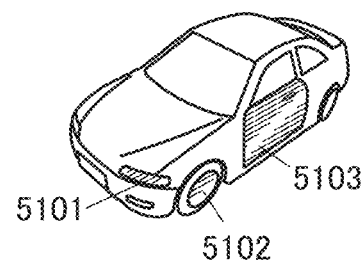
FIG. 10A and FIG. 10B are diagrams illustrating an automobile.
Figure 10B:
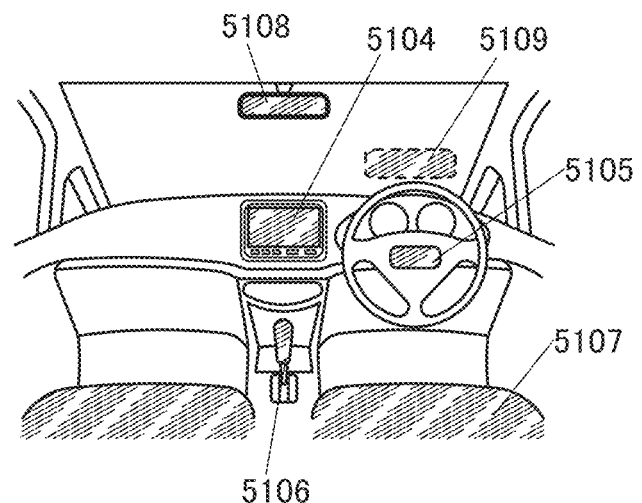

FIG. T0A and FIG. 10B show an automobile including the light-emitting apparatus. In other words, the light-emitting apparatus can be integrated into an automobile. Specifically, the light-emitting apparatus can be applied to lights 5101 (including lights of the rear part of the car), a tire wheel 5102, a part or the whole of a door 5103, or the like on the outer side of the automobile shown in FIG. 10A. The light-emitting apparatus can also be applied to a display portion 5104, a steering wheel 5105, a shifter 5106, a seat 5107, an inner rearview mirror 5108, a windshield 5109, or the like on the inner side of the automobile shown in FIG. 10B. The light-emitting apparatus may be applied to part of any of the other glass windows.

In the above manner, the electronic devices and the automobile each including the light-emitting apparatus of one embodiment of the present invention can be obtained. In that case, a long-lifetime electronic device can be achieved. In addition, the light-emitting apparatus can be used for electronic devices and automobiles in a variety of fields without being limited to those described in this embodiment.

Note that the structure described in this embodiment can be used in an appropriate combination with any of the structures described in the other embodiments.

Embodiment 7

In this embodiment, a structure of a lighting device fabricated using the light-emitting apparatus of one embodiment of the present invention or the light-emitting device which is part of the light-emitting apparatus will be described with reference to FIG. 11.

Figure 11A:
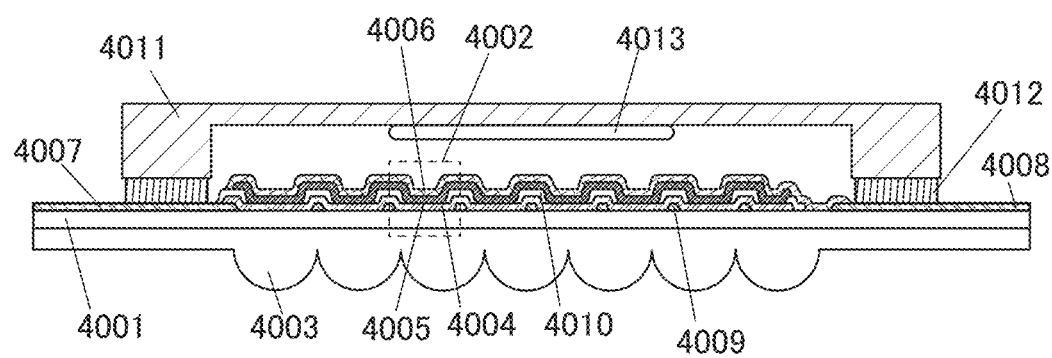
FIG. 11A and FIG. 11B are diagrams illustrating lighting devices.
Figure 11B:
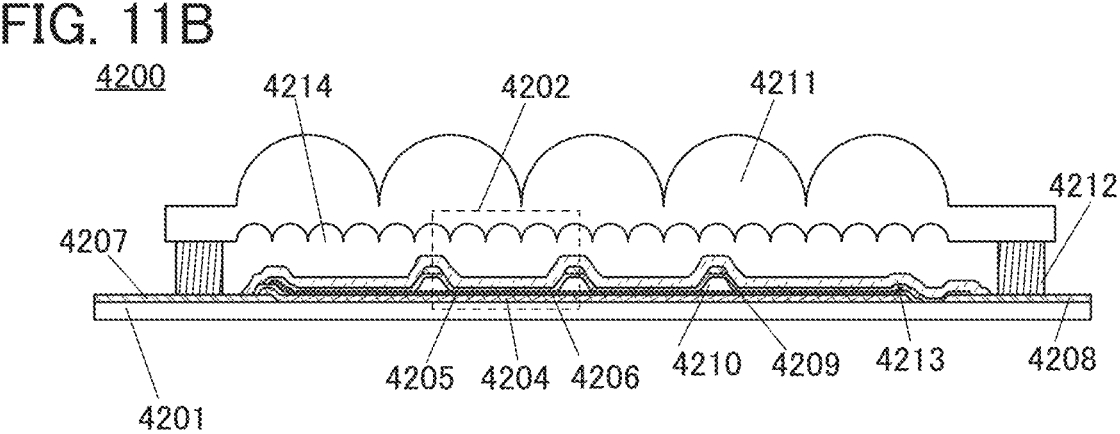

FIG. 11A and FIG. 11B show examples of cross-sectional views of lighting devices. FIG. 11A illustrates a bottom-emission lighting device in which light is extracted from the substrate side, and FIG. 11B illustrates a top-emission lighting device in which light is extracted from the sealing substrate side.

A lighting device 4000 shown in FIG. 11A includes a light-emitting device 4002 over a substrate 4001. In addition, the lighting device 4000 includes a substrate 4003 with unevenness on the outer side of the substrate 4001. The light-emitting device 4002 includes a first electrode 4004, an EL layer 4005, and a second electrode 4006.

The first electrode 4004 is electrically connected to an electrode 4007, and the second electrode 4006 is electrically connected to an electrode 4008. An auxiliary wiring 4009 electrically connected to the first electrode 4004 may be provided. An insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting device 4002. Since the substrate 4003 has the unevenness shown in FIG. 11A, the extraction efficiency of light generated in the light-emitting device 4002 can be increased.

A lighting device 4200 in FIG. 11B includes a light-emitting device 4202 over a substrate 4201. The light-emitting device 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting device 4202. Since the sealing substrate 4211 has the unevenness shown in FIG. 11B, the extraction efficiency of light generated in the light-emitting device 4202 can be increased.

Application examples of such lighting devices include ceiling lights for indoor lighting. Examples of the ceiling lights include a ceiling direct mount light and a ceiling embedded light. Such a lighting device is fabricated using the light-emitting apparatus and a housing or a cover in combination.

As another example, such lighting devices can be used for a foot light that illuminates a floor so that safety on the floor can be improved. The foot light can be effectively used in a bedroom, on a staircase, or on a passage, for example. In such a case, the size and shape of the foot light can be changed depending on the area or structure of a room. The foot light can also be a stationary lighting device fabricated using the light-emitting apparatus and a support base in combination.

Such lighting devices can also be used for a sheet-like lighting device (sheet-like lighting). The sheet-like lighting, which is attached to a wall when used, is space-saving and thus can be used for a wide variety of applications. The area of the sheet-like lighting can be easily increased. The sheet-like lighting can also be used on a wall and a housing that have a curved surface.

Besides the above examples, the light-emitting apparatus of one embodiment of the present invention or the light-emitting device which is a part of the light-emitting apparatus can be used as part of furniture in a room, whereby a lighting device that has a function of the furniture can be obtained.

As described above, a variety of lighting devices that include the light-emitting apparatus can be obtained. Note that these lighting devices are also embodiments of the present invention.

The structures described in this embodiment can be used in an appropriate combination with any of the structures described in the other embodiments.

[Chemical Formula 30]

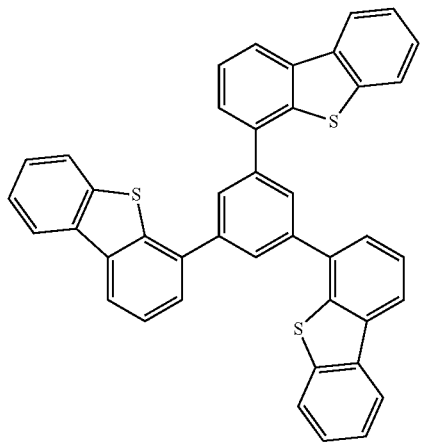

DBT3P-II

Example 1

In this example, a light-emitting device of one embodiment of the present invention and a comparative light-emitting device were fabricated and the operation characteristics of the devices were measured. Note that in a light-emitting layer of the light-emitting device 1 of one embodiment of the present invention, 4,6-bis[3-(9H-carbazol-9-yl)phenyl]pyrimidine (abbreviation: 4,6mCzP2Pm) was used as a host material, and 2-trimethylsilyl-N,N,N',N'-tetrakis(3,5-di-tert-butylphenyl)-9,10-anthracenediamine (abbreviation: 2TMS-mmtBuDPhA2Anth), which is an organic compound having a protecting group and a function of converting singlet excitation energy into light emission, and bis[2-[5-(2,6-dimethylphenyl)-3-(3,5-dimethylphenyl)-2-pyrazinyl-κN]-4,6-dimethylphenyl-κC](2,2',6,6'-tetramethyl-3,5-heptadionato-κ2O,O')iridium(III) (abbreviation: [Ir(dmdppr-dmp)$_2$(dpm)]), which is an organic compound having a function of converting triplet excitation energy into light emission, were used as guest materials. In a comparative light-emitting device 2 as a comparative device, 9,10-bis[phenyl(p-tolyl)-anilino]anthracene (abbreviation: MeDPhA2A) was used instead of 2TMS-mmtBuDPhA2Anth in the light-emitting device 1.

Figure 12:
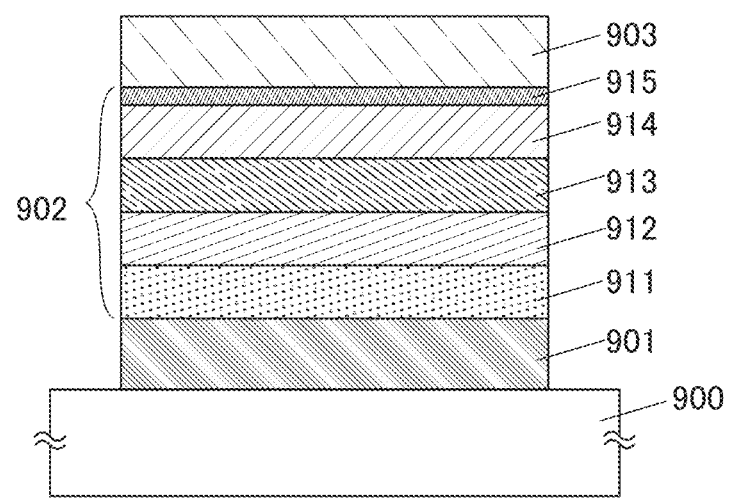
FIG. 12 is a diagram illustrating a light-emitting device.

Note that FIG. 12 shows the device structure of the light-emitting devices used in this example, and Table 1 shows specific compositions. Chemical formulae of materials used in this example are shown below.

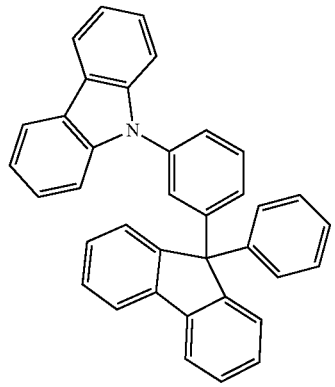

mCzFLP

TABLE 1

| | First electrode | Hole-injection layer | Hole-transport layer | Light-emitting layer | Electron-transport layer | | Electron-injection layer | Second electrode |
|---|---|---|---|---|---|---|---|---|
| Light-emitting device 1 | ITSO (70 nm) | DBT3P-II:MoOx (1:0.5 40 nm) | mCzFLP (20 nm) | * | 4,6mCzP2Pm (20 nm) | | NBphen (10 nm) | LiF (1 nm) Al (200 nm) |
| Comparative light-emitting device 2 | ITSO (70 nm) | DBT3P-II:MoOx (1:0.5 40 nm) | mCzFLP (20 nm) | ** | 4,6mCzP2Pm (20 nm) | | NBphen (10 nm) | LiF (1 nm) Al (200 nm) |

* 4,6mCzP2Pm:2TMS-mmtBuDPhA2Anth:[Ir(dmdppr-dmp)$_2$(dpm)] (1:0.025:0.005 40 nm)
** 4,6mCzP2Pm:MeDPhA2A:[Ir(dmdppr-dmp)$_2$(dpm)] (1:0.05:0.01 40 nm)

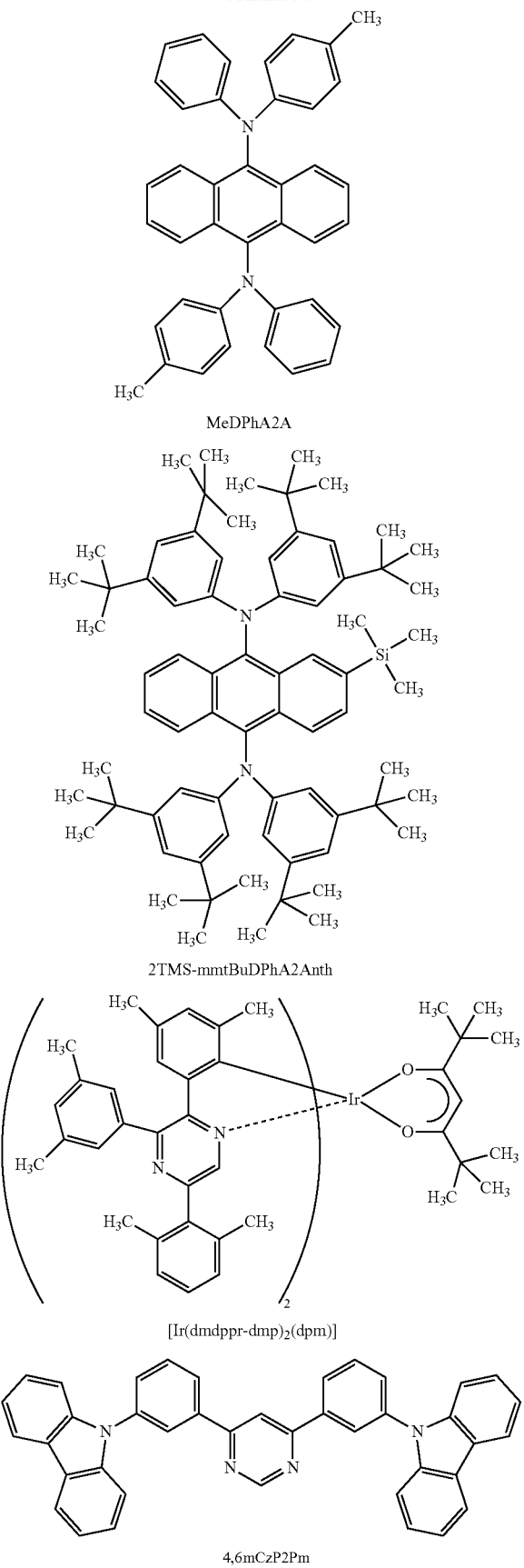

MeDPhA2A

2TMS-mmtBuDPhA2Anth

[Ir(dmdppr-dmp)₂(dpm)]

4,6mCzP2Pm

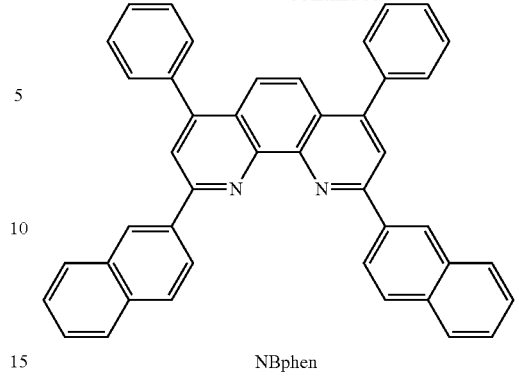

NBphen

<<Fabrication of Light-Emitting Devices>>

The light-emitting devices described in this example have a structure shown in FIG. 12, in which a hole-injection layer 911, a hole-transport layer 912, a light-emitting layer 913, an electron-transport layer 914, and an electron-injection layer 915 included in an EL layer 902 are stacked in this order over a first electrode 901 formed over a substrate 900, and a second electrode 903 is stacked over the electron-injection layer 915.

First, the first electrode 901 was formed over the substrate 900. The electrode area was set to 4 mm² (2 mm×2 mm). A glass substrate was used as the substrate 900. The first electrode 901 was formed to a thickness of 70 nm using indium tin oxide containing silicon oxide (ITSO) by a sputtering method.

As pretreatment, a surface of the substrate was washed with water, baking was performed at 200° C. for 1 hour, and then UV ozone treatment was performed for 370 seconds. After that, the substrate was transferred into a vacuum evaporation apparatus in which the pressure was reduced to about 1×10⁻⁴ Pa, vacuum baking at 170° C. for 30 minutes was performed in a heating chamber in the vacuum evaporation apparatus, and then the substrate was naturally cooled down for about 30 minutes.

Next, the hole-injection layer 911 was formed over the first electrode 901. For the formation of the hole-injection layer 911, the pressure in the vacuum evaporation apparatus was reduced to 1×10⁻⁴ Pa, and then 1,3,5-tri(dibenzothiophen-4-yl)benzene (abbreviation: DBT3P-II) and molybdenum oxide were co-evaporated such that DBT3P-II:molybdenum oxide was equal to 1:0.5 (mass ratio) and the thickness was 40 nm.

Then, the hole-transport layer 912 was formed over the hole-injection layer 911. The hole-transport layer 912 was formed to a thickness of 20 nm by evaporation using 9-[3-(9-phenyl-9H-fluoren-9-yl)phenyl]9H-carbazole (abbreviation: mCzFLP).

Next, the light-emitting layer 913 was formed over the hole-transport layer 912.

For the light-emitting layer 913 in the light-emitting device 1, 4,6mCzP2Pm was used as a host material and 2TMS-mmtBuDPhA2Anth, which is an organic compound having a protecting group and a function of converting singlet excitation energy into light emission, and [Ir(dmdppr-dmp)₂(dpm)], which is an organic compound having a function of converting triplet excitation energy into light emission, were used as guest materials; and co-evaporation was performed such that the weight ratio was 4,6mCzP2Pm: 2TMS-mmtBuDPhA2Anth: [Ir(dmdppr-dmp)$_2$(dpm)]=1:0.025:0.005. The thickness was set to 40 nm.

In the case of the comparative light-emitting device 2, 4,6mCzP2Pm was used as a host material and MeDPhA2A, which is an organic compound having a function of converting singlet excitation energy into light emission, and [Ir(dmdppr-dmp)$_2$(dpm)], which is an organic compound having a function of converting triplet excitation energy into light emission, were used as guest materials; and co-evaporation was performed such that the weight ratio was 4,6mCzP2Pm:MeDPhA2A:[Ir(dmdppr-dmp)$_2$(dpm)]=1: 0.05:0.01. The thickness was set to 40 nm.

Next, the electron-transport layer 914 was formed over the light-emitting layer 913. The electron-transport layer 914 was formed by sequential evaporation of 4,6mCzP2Pm and 2,9-bis(naphthalen-2-yl)-4,7-diphenyl-1,10-phenanthroline (abbreviation: NBphen) to thicknesses of 20 nm and 10 nm, respectively.

Then, the electron-injection layer 915 was formed over the electron-transport layer 914. The electron-injection layer 915 was formed to a thickness of 1 nm by evaporation using lithium fluoride (LiF).

After that, the second electrode 903 was formed over the electron-injection layer 915. The second electrode 903 was formed to a thickness of 200 nm by an evaporation method using aluminum. In this example, the second electrode 903 functions as a cathode.

Through the above steps, the light-emitting devices in each of which an EL layer was provided between a pair of electrodes were formed over the substrate 900. The hole-injection layer 911, the hole-transport layer 912, the light-emitting layer 913, the electron-transport layer 914, and the electron-injection layer 915 described in the above steps are functional layers forming the EL layer in one embodiment of the present invention. Furthermore, in all the evaporation steps in the above fabrication method, an evaporation method by a resistance-heating method was used.

The light-emitting devices fabricated as described above are sealed using a different substrate (not shown). At the time of the sealing using the different substrate (not shown), the different substrate (not shown) coated with a sealant that solidifies by ultraviolet light was fixed onto the substrate 900 in a glove box containing a nitrogen atmosphere, and the substrates were bonded to each other such that the sealant would be attached to the periphery of the light-emitting device formed over the substrate 900. At the time of the sealing, the sealant was irradiated with 365-nm ultraviolet light at 6 J/cm$^2$ to be solidified, and the sealant was subjected to heat treatment at 80° C. for 1 hour to be stabilized.

<<Operation Characteristics of Light-Emitting Devices>>

Figure 13:
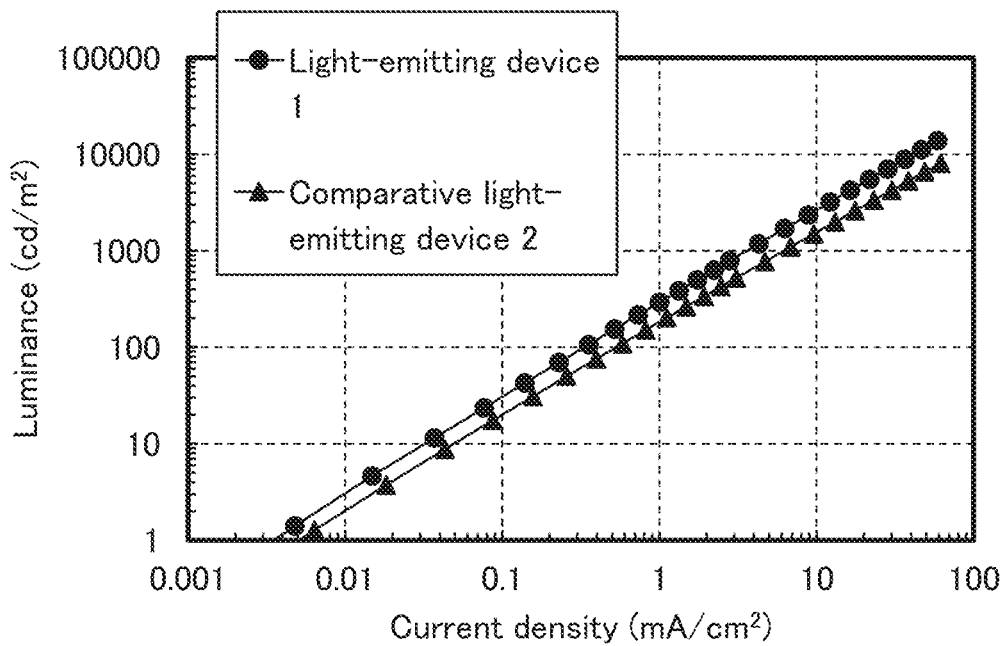
FIG. 13 is a graph showing the current density-luminance characteristics of a light-emitting device 1 and a comparative light-emitting device 2.
Figure 14:
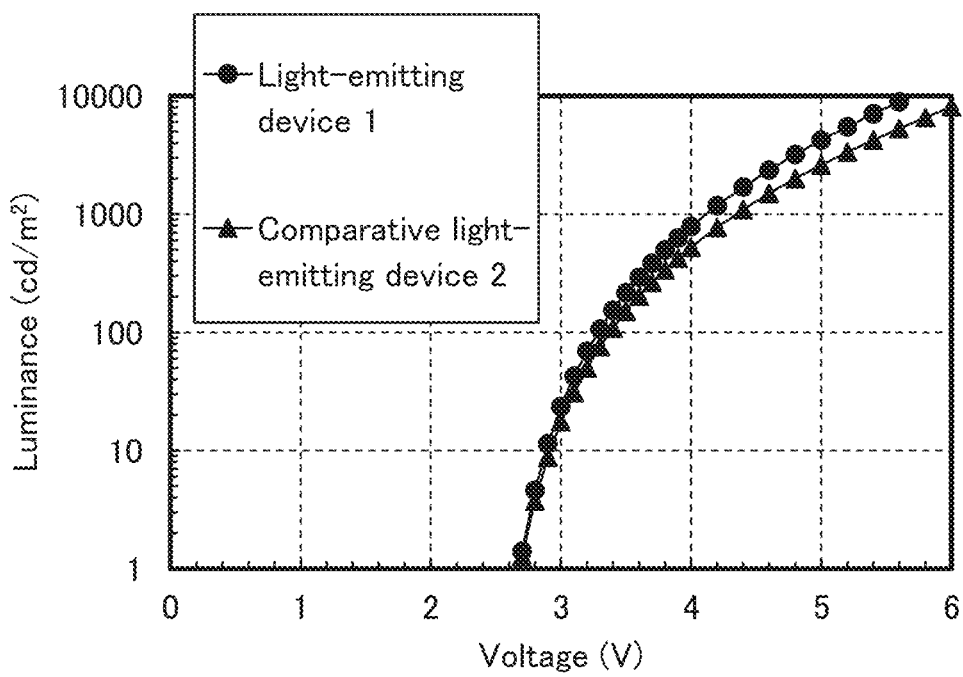
FIG. 14 is a graph showing the voltage-luminance characteristics of the light-emitting device 1 and the comparative light-emitting device 2.
Figure 15:
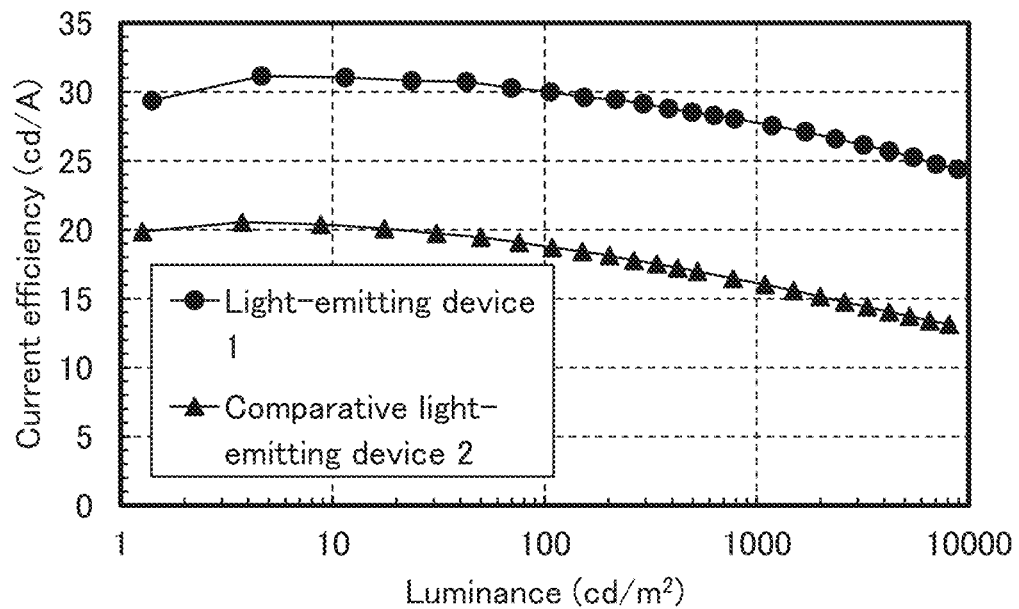
FIG. 15 is a graph showing the luminance-current efficiency characteristics of the light-emitting device 1 and the comparative light-emitting device 2.
Figure 16:
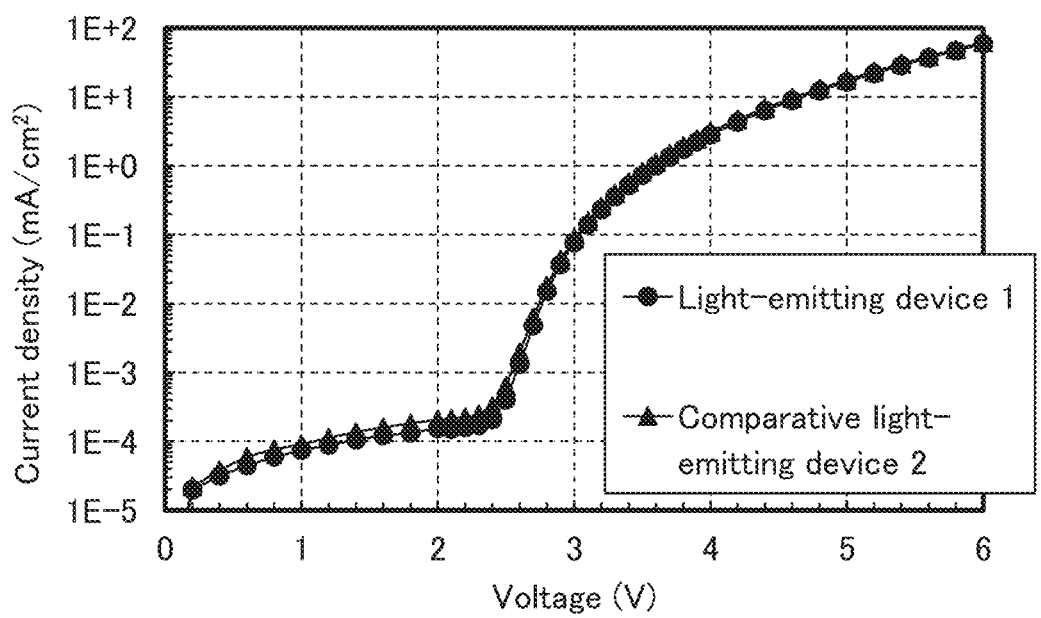
FIG. 16 is a graph showing the voltage-current density characteristics of the light-emitting device 1 and the comparative light-emitting device 2.
Figure 17:
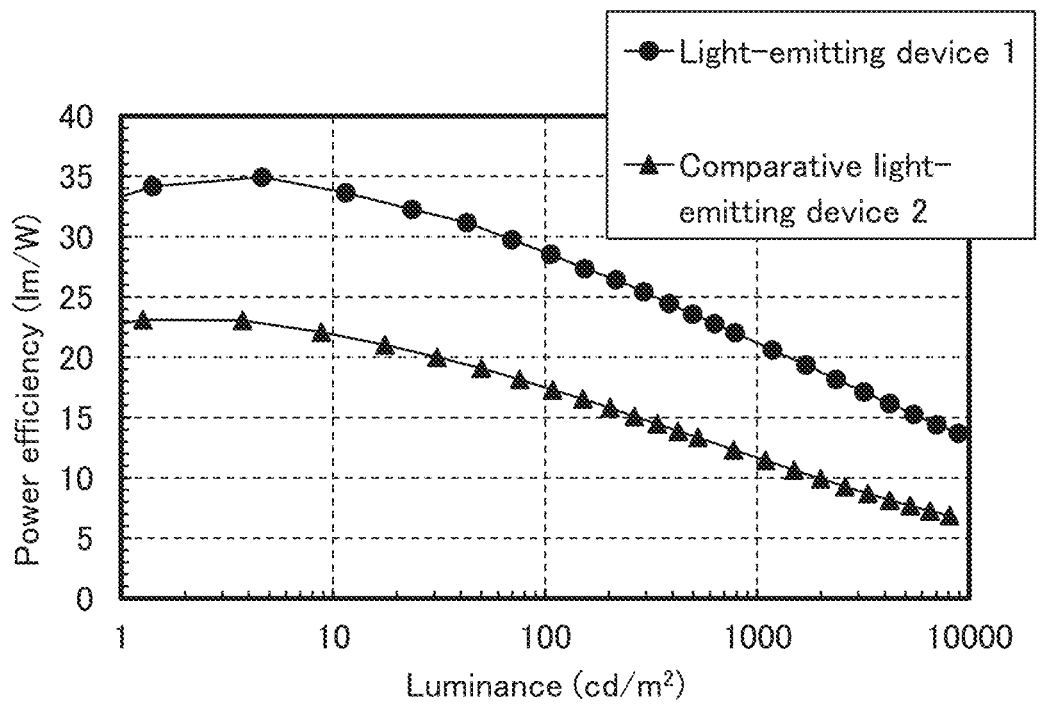
FIG. 17 is a graph showing the luminance-power efficiency characteristics of the light-emitting device 1 and the comparative light-emitting device 2.
Figure 18:
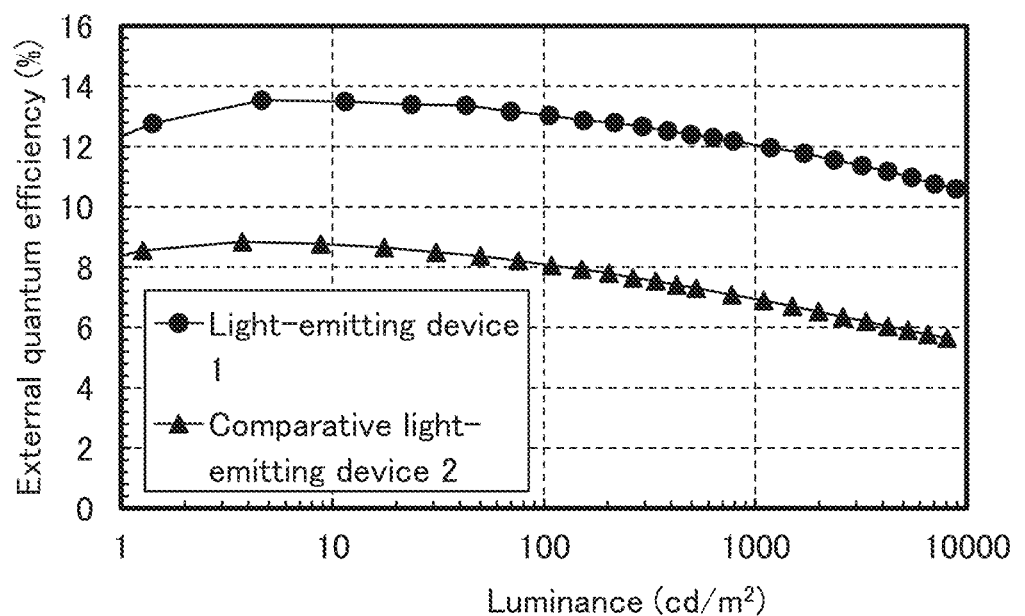
FIG. 18 is a graph showing the luminance-external quantum efficiency characteristics of the light-emitting device 1 and the comparative light-emitting device 2.

Operation characteristics of the fabricated light-emitting devices were measured. Luminance and chromaticity (CIE chromaticity) were measured with a luminance colorimeter (BM-5A manufactured by TOPCON TECHNOHOUSE CORPORATION), and electroluminescence (EL) spectra were measured with a multi-channel spectrometer (PMA-11 manufactured by Hamamatsu Photonics K.K.). Note that the measurement was carried out at room temperature (an atmosphere maintained at 23° C.). As the results of the operation characteristics of the light-emitting device 1 and the comparative light-emitting device 2, the current density-luminance characteristics are shown in FIG. 13, the voltage-luminance characteristics are shown in FIG. 14, the luminance-current efficiency characteristics are shown in FIG. 15, the voltage-current density characteristics are shown in FIG. 16, the luminance-power efficiency characteristics are shown in FIG. 17, and the luminance-external quantum efficiency characteristics are shown in FIG. 18.

Figure 19:
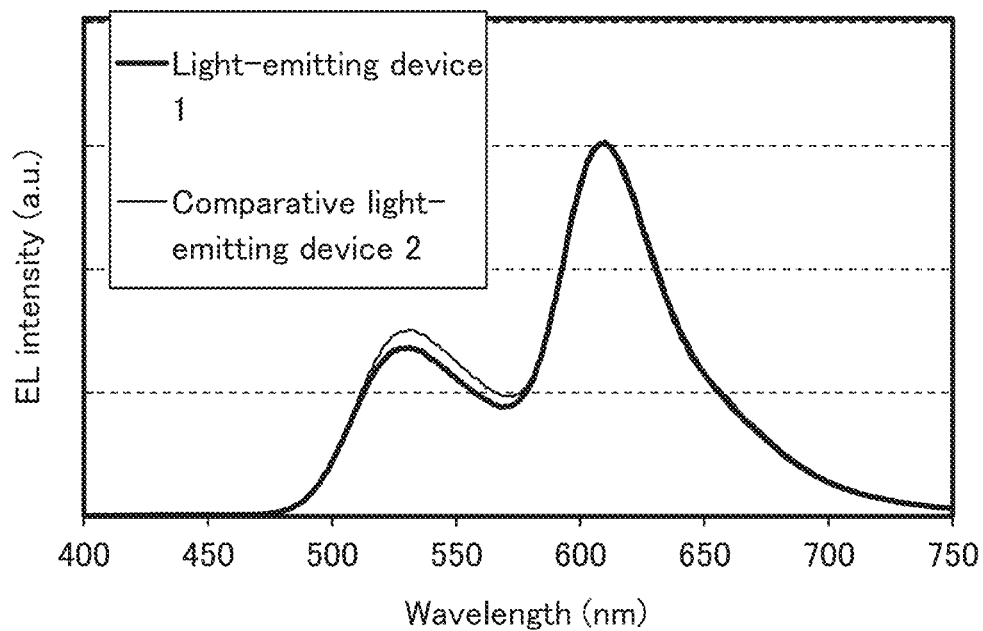
FIG. 19 is a graph showing the electroluminescence spectra of the light-emitting device 1 and the comparative light-emitting device 2.
Figure 20:
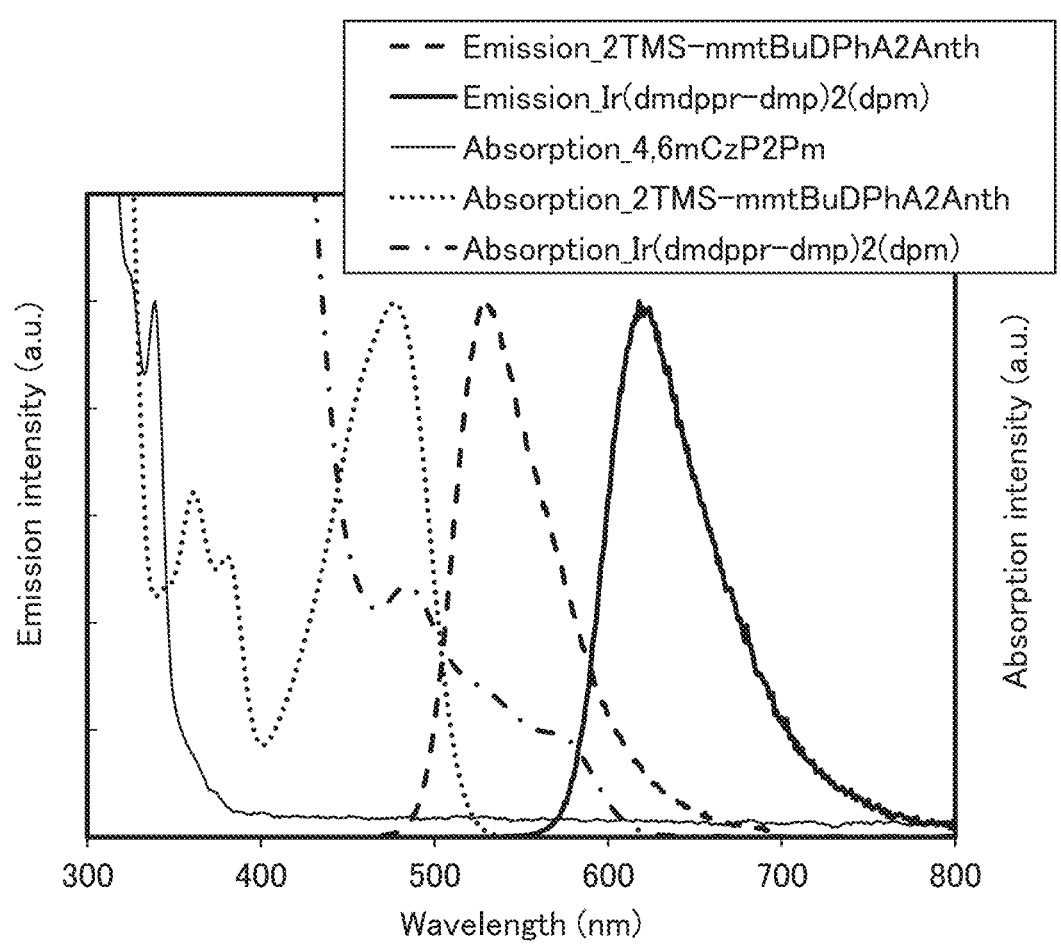
FIG. 20 is a graph showing the ultraviolet-visible absorption spectra and emission spectra of 2TMS-mmtBuDPhA2Anth and [Ir(dmdppr-dmp)$_2$(dpm)] in a solution.

FIG. 19 shows the electroluminescence spectra (EL spectra) of the light-emitting devices to which current flows at a current density of 2.5 mA/cm$^2$. FIG. 20 shows the measured results of the materials used for the light-emitting element 1 and the comparative light-emitting element 2: the ultraviolet-visible absorption spectrum and emission spectrum of 2TMS-mmtBuDPhA2Anth in a toluene solution, the ultraviolet-visible absorption spectrum and emission spectrum of [Ir(dmdppr-dmp)$_2$(dpm)] in a dichloromethane solution, and the ultraviolet-visible absorption spectrum of 4,6mCzP2Pm in a toluene solution. Note that in FIG. 20, the absorption spectra were measured with an ultraviolet-visible spectrophotometer (V550, manufactured by JASCO Corporation), and the emission spectra were measured with a fluorescence spectrophotometer (FS920, manufactured by Hamamatsu Photonics K.K.). FIG. 20 shows that the peak wavelength of the emission spectrum of Ir(dmdppr-dmp)$_2$(dpm), which is a phosphorescent substance, is longer than that of 2TMS-mmtBuDPhA2Anth, which is a fluorescent substance.

The absorption edge of the absorption spectrum or the emission edge of the emission spectrum on the short wavelength side of 2TMS-mmtBuDPhA2Anth as the fluorescent substance has a shorter wavelength than the absorption edge of the absorption spectrum or the emission edge of the emission spectrum on the short wavelength side of Ir(dmdppr-dmp)$_2$(dpm) as the phosphorescent substance; thus, the S1 level of 2TMS-mmtBuDPhA2Anth as the fluorescent substance is found to be higher than the T1 level of Ir(dmdppr-dmp)$_2$(dpm) as the phosphorescent substance. The absorption edge of the absorption spectrum of 4,6mCzP2Pm as the host material has a shorter wavelength than the absorption edge of the absorption spectrum or the emission edge of the emission spectrum on the short wavelength side of 2TMS-mmtBuDPhA2Anth as the fluorescent substance; thus, the S1 level of 4,6mCzP2Pm as the host material is found to be higher than the S1 level of 2TMS-mmtBuDPhA2Anth as the fluorescent substance.

In order to obtain the T1 level of 4,6mCzP2Pm, a thin film of 4,6mCzP2Pm was formed over a quartz substrate by a vacuum evaporation method, and the emission spectrum of the thin film was measured at a low temperature (10 K). For the measurement, a PL microscope, LabRAM HR-PL (HORIBA, Ltd.) was used, the measurement temperature was 10 K, a He—Cd laser having a wavelength of 325 nm was used as excitation light, and a CCD was used as a detector. The T1 level was calculated from the energy with the wavelength of a line obtained by extrapolating a tangent to the emission spectrum, which was measured at a low temperature, at a tail on the short wavelength side; as a result, the T1 level of 4,6mCzP2Pm was 2.79 eV (444 nm). Thus, FIG. 20 shows that the T1 level of 4,6mCzP2Pm as the host material is higher than the T1 level of Ir(dmdppr-dmp)$_2$(dpm) as the phosphorescent substance.

Table 2 below shows the initial values of the main characteristics of each of the light-emitting devices at around 1000 cd/m$^2$.

TABLE 2

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) | External energy efficiency (%) |
|---|---|---|---|---|---|---|---|---|---|
| Light-emitting device 1 | 4.2 | 0.17 | 4.3 | (0.51, 0.47) | 1200 | 28 | 21 | 12 | 5.9 |
| Comparative light-emitting device 2 | 4.4 | 0.27 | 6.8 | (0.50, 0.49) | 1100 | 16 | 11 | 6.9 | 3.2 |

As shown in FIG. 19, each of the EL spectra of the light-emitting devices has two peaks at around 530 nm and around 610 nm. Note that in the light-emitting device 1, the peak at around 530 nm is derived from 2TMS-mmtBuDPhA2Anth whereas the peak at around 610 nm is derived from [Ir(dmdppr-dmp)$_2$(dpm)]. In the comparative light-emitting device 2, the peak at around 530 nm is derived from MeDPhA2A whereas the peak at around 610 nm is derived from [Ir(dmdppr-dmp)$_2$(dpm)]. This indicates that emission (fluorescence) derived from 2TMS-mmtBuDPhA2Anth and emission (phosphorescence) derived from Ir(dmdppr-dmp)$_2$(dpm) are obtained in the light-emitting device 1, and emission (fluorescence) derived from MeDPhA2A and emission (phosphorescence) derived from Ir(dmdppr-dmp)$_2$(dpm) are obtained in the comparative light-emitting device 2. Thus, the results of the EL spectra confirmed that emission from different guest materials was concurrently obtained in both of the light-emitting devices.

In contrast, as shown in FIG. 15, FIG. 17, and FIG. 18, the result on the efficiency versus luminance was superior in the light-emitting device 1 to that in the comparative light-emitting device 2, and the light-emitting device 1 exhibited a high external quantum efficiency exceeding 10% though the fluorescent substance is used as the guest material. This indicates that the use of the organic compound having a protecting group (the first organic compound 121 described in Embodiment 2) as the organic compound having a function of converting singlet excitation energy into light emission, which is the guest material of the light-emitting layer, inhibits transfer of triplet excitation energy from the host material to the fluorescent substance by the Dexter mechanism to inhibit deactivation of the triplet excitation energy due to the energy transfer, thereby inhibiting a decrease in the emission efficiency of the light-emitting device.

<CV Measurement Results>

Next, the electrochemical characteristics (oxidation reaction characteristics and reduction reaction characteristics) of 4,6mCzP2Pm as the host material (the first organic compound), 2TMS-mmtBuDPhA2Anth as the guest material (the second organic compound), and [Ir(dmdppr-dmp)$_2$(dpm)] as the guest material (the third organic compound), which are used in the light-emitting layer of each light-emitting device, were measured by cyclic voltammetry (CV).

An electrochemical analyzer (model number: ALS model 600A or 600C, manufactured by BAS Inc.) was used as a measurement apparatus. To prepare a solution for the CV measurement, dehydrated dimethylformamide (DMF) (manufactured by Sigma-Aldrich Inc., 99.8%, catalog No. 22705-6) was used as a solvent, tetra-n-butylammonium perchlorate (n-Bu$_4$NClO$_4$) (manufactured by Tokyo Chemical Industry Co., Ltd., catalog No. T0836) as a supporting electrolyte was dissolved at a concentration of 100 mmol/L, and the object to be measured was dissolved at a concentration of 2 mmol/L. A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag$^+$ electrode (RE7 reference electrode for non-aqueous solvent, manufactured by BAS Inc.) was used as a reference electrode. Note that the measurement was performed at room temperature (20 to 25° C.). The scan speed in the CV measurement was fixed to 0.1 V/sec, and an oxidation potential Ea [V] and a reduction potential Ec [V] with respect to the reference electrode were measured. Ea is an intermediate potential of an oxidation-reduction wave, and Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec.

According to the CV measurement results, the oxidation potential of 4,6mCzP2Pm was 0.95 V and the reduction potential was −2.06 V. The HOMO level of 4,6mCzP2Pm, which was calculated from the CV measurement, was −5.89 eV and the LUMO level was −2.88 eV. The oxidation potential of 2TMS-mmtBuDPhA2Anth was 0.45 V and the reduction potential was −2.12 V. The HOMO level of 2TMS-mmtBuDPhA2Anth, which was calculated from the CV measurement, was −5.39 eV and the LUMO level was −2.82 eV. The oxidation potential of [Ir(dmdppr-dmp)$_2$(dpm)] was 0.54 V and the reduction potential was −2.06 V. The HOMO level of [Ir(dmdppr-dmp)$_2$(dpm)], which was calculated from the CV measurement, was −5.48 eV and the LUMO level was −2.89 eV.

Example 2

In this example, a light-emitting device of one embodiment of the present invention and comparative light-emitting devices were fabricated and the operation characteristics of the devices were measured. Note that in a light-emitting layer of a light-emitting device 3 of one embodiment of the present invention, 2-[4'-(9-phenyl-9H-carbazol-3-yl)-3,1'-biphenyl-1-yl]dibenzo[f,h]quinoxaline (abbreviation: 2mpPCBPDBq) was used as a host material, and 2TMS-mmtBuDPhA2Anth, which is an organic compound having a protecting group and a function of converting singlet excitation energy into light emission, and [Ir(dmdppr-dmp)$_2$(dpm)], which is an organic compound having a function of converting triplet excitation energy into light emission, were used as guest materials. In a comparative light-emitting device 4 and a comparative light-emitting device 5 as comparative devices, MeDPhA2A was used instead of 2TMS-mmtBuDPhA2Anth in the light-emitting device 3.

Note that the device structure of the light-emitting device 3, the comparative light-emitting device 4, and the comparative light-emitting device 5 fabricated in this example is similar to that in FIG. 12 shown in Example 1, and the specific composition of each layer of the device structure is as shown in Table 3. Chemical formulae of materials used in this example are shown below.

TABLE 3

|  | First electrode | Hole-injection layer | Hole-transport layer | | Light-emitting layer | Electron-transport layer | Electron-injection layer | Second electrode |
|---|---|---|---|---|---|---|---|---|
| Light-emitting device 3 | ITSO (70 nm) | DBT3P-II:MoOx (1:0.5 40 nm) | mCzFLP (20 nm) | * | 2mDBTBPDBq-II (20 nm) | NBphen (10 nm) | LiF (1 nm) | Al (200 nm) |
| Comparative light-emitting device 4 | ITSO (70 nm) | DBT3P-II:MoOx (1:0.5 40 nm) | mCzFLP (20 nm) | ** | 2mDBTBPDBq-II (20 nm) | NBphen (10 nm) | LiF (1 nm) | Al (200 nm) |
| Comparative light-emitting device 5 | ITSO (70 nm) | DBT3P-II:MoOx (1:0.5 40 nm) | mCzFLP (20 nm) | *** | 2mDBTBPDBq-II (20 nm) | NBphen (10 nm) | LiF (1 nm) | Al (200 nm) |

\* 2mpPCBPDBq:2TMS-mmtBuDPhA2Anth:[Ir(dmdppr-dmp)$_2$(dpm)] (1:0.025:0.005 40 nm)

\*\* 2mpPCBPDBq:MeDPhA2A:[Ir(dmdppr-dmp)$_2$(dpm)] (1:0.025:0.005 40 nm)

\*\*\* 2mpPCBPDBq:MeDPhA2A:[Ir(dmdppr-dmp)$_2$(dpm)] (1:0.05:0.01 40 nm)

[Chemical Formula 31]

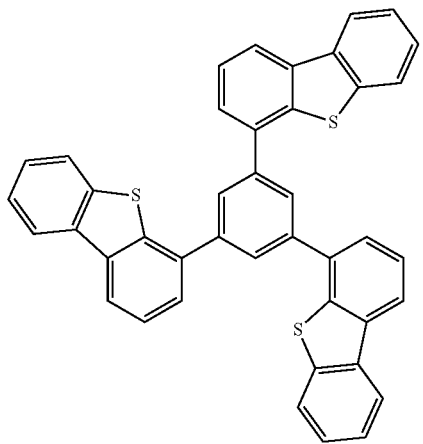

DBT3P-II

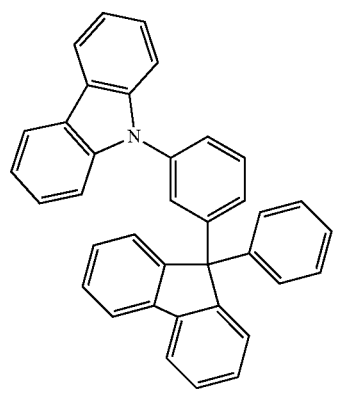

mCzFLP

-continued

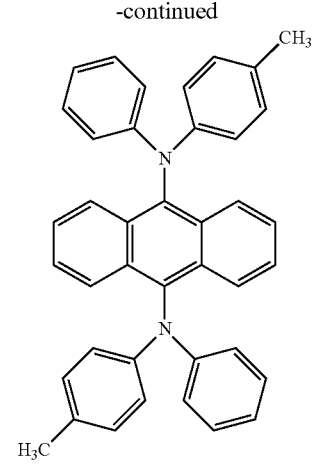

MeDPhA2A

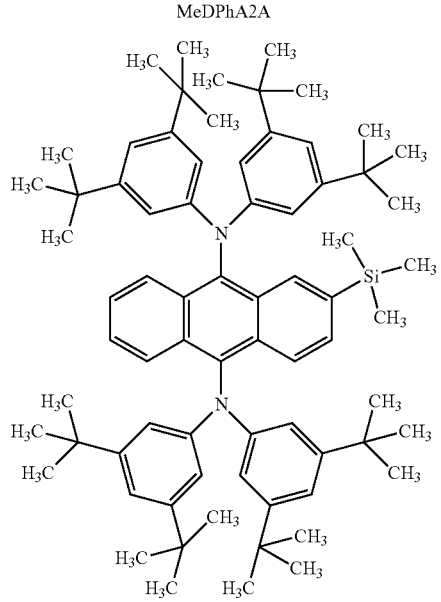

2TMS-mmtBuDPhA2Anth

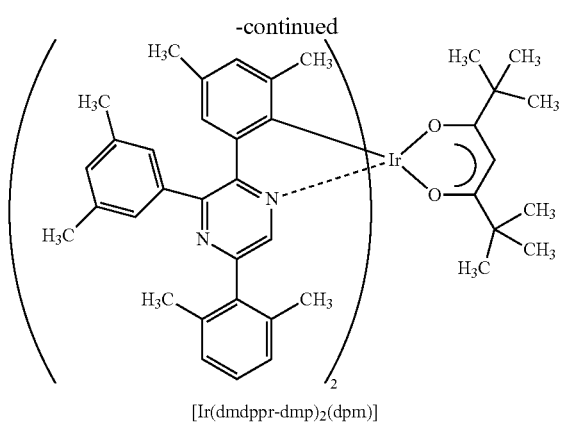

[Ir(dmdppr-dmp)₂(dpm)]

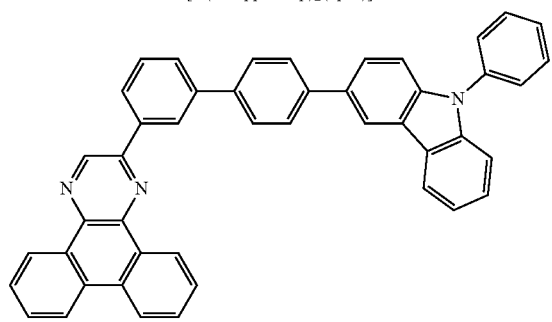

2mpPCBPDBq

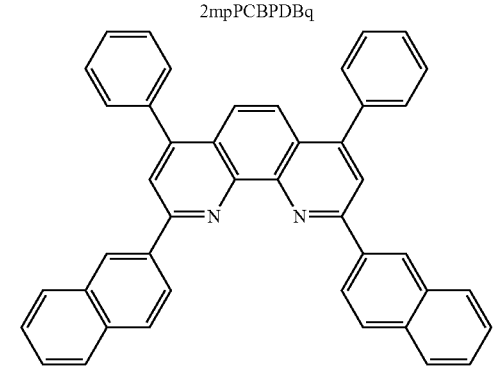

NBphen

<<Operation Characteristics of Light-Emitting Devices>>

Figure 21:
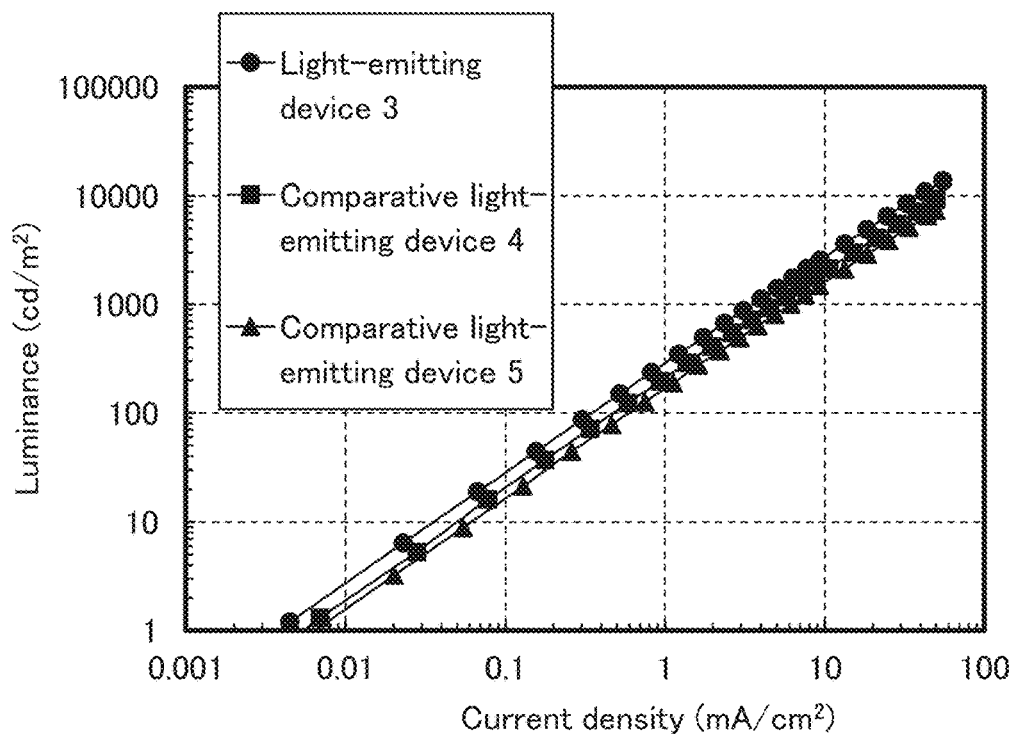
FIG. 21 is a graph showing the current density-luminance characteristics of a light-emitting device 3, a comparative light-emitting device 4, and a comparative light-emitting device 5.
Figure 22:
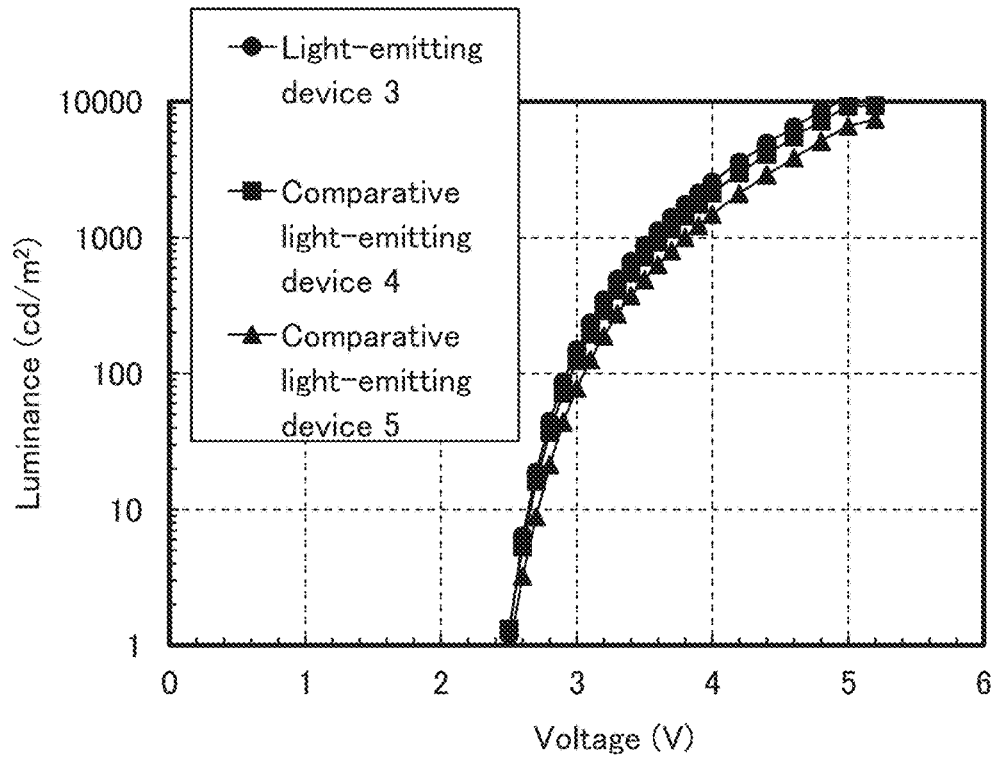
FIG. 22 is a graph showing the voltage-luminance characteristics of the light-emitting device 3, the comparative light-emitting device 4, and the comparative light-emitting device 5.
Figure 23:
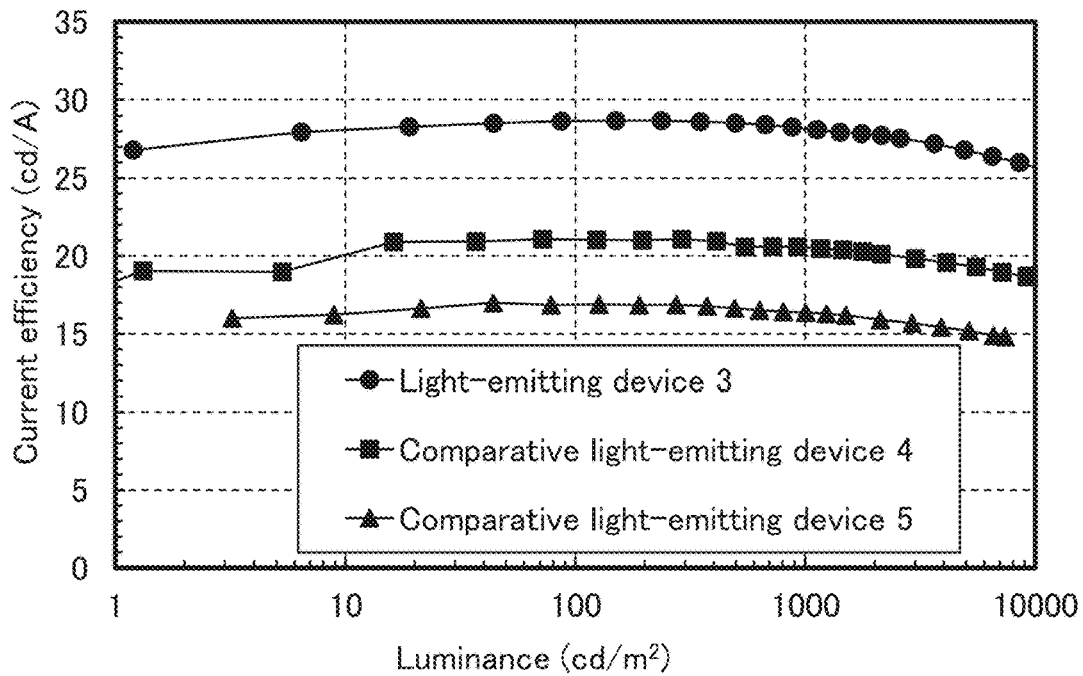
FIG. 23 is a graph showing the luminance-current efficiency characteristics of the light-emitting device 3, the comparative light-emitting device 4, and the comparative light-emitting device 5.
Figure 24:
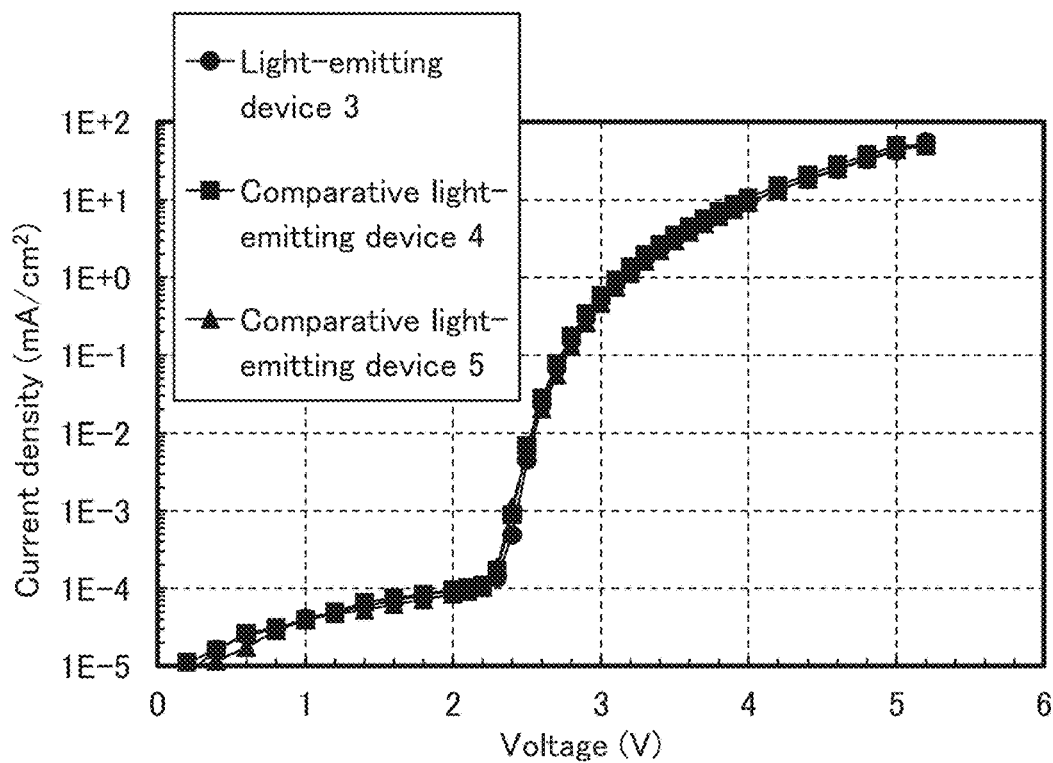
FIG. 24 is a graph showing the voltage-current density characteristics of the light-emitting device 3, the comparative light-emitting device 4, and the comparative light-emitting device 5.
Figure 25:
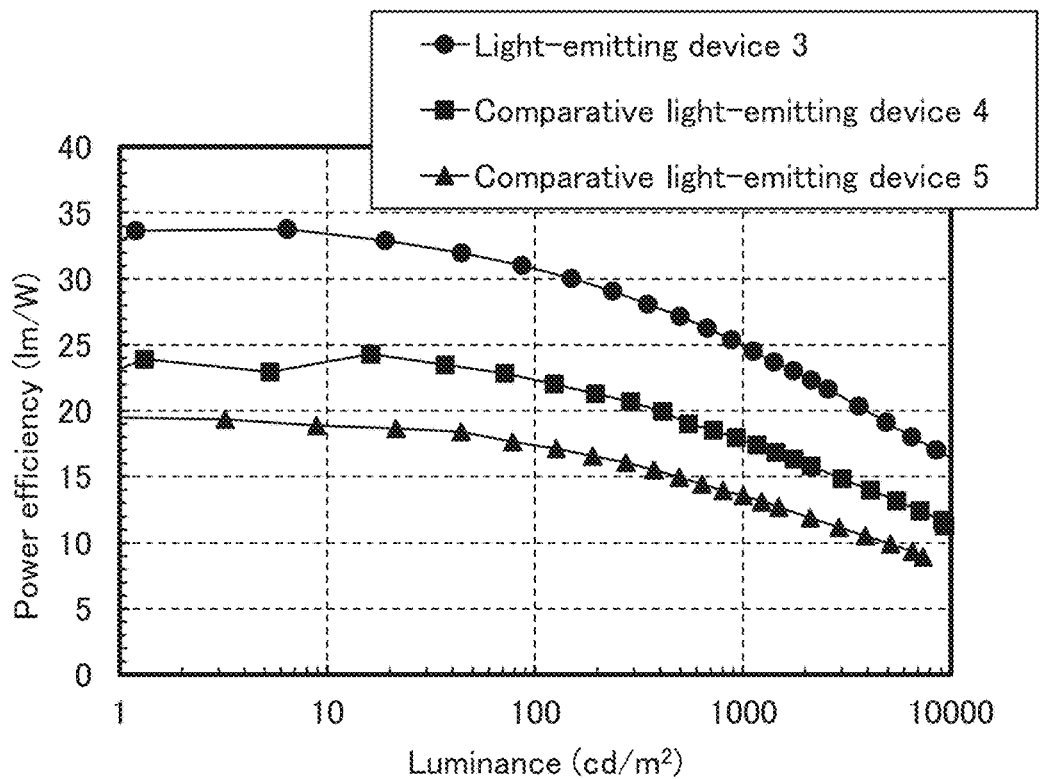
FIG. 25 is a graph showing the luminance-power efficiency characteristics of the light-emitting device 3, the comparative light-emitting device 4, and the comparative light-emitting device 5.
Figure 26:
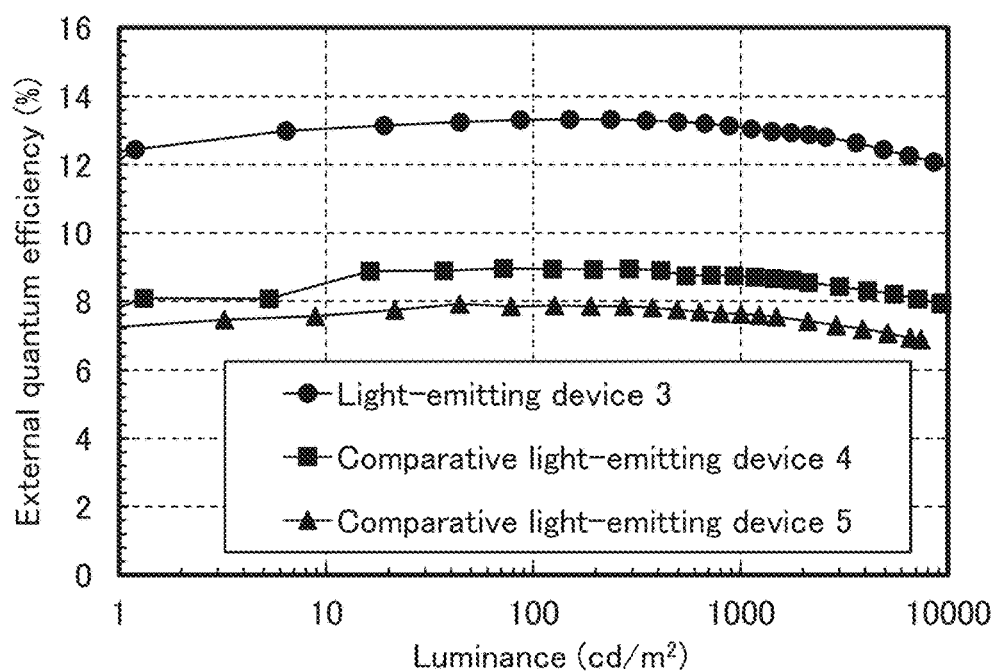
FIG. 26 is a graph showing the luminance-external quantum efficiency characteristics of the light-emitting device 3, the comparative light-emitting device 4, and the comparative light-emitting device 5.

Operation characteristics of the fabricated light-emitting devices were measured. Luminance and chromaticity (CIE chromaticity) were measured with a luminance colorimeter (BM-5A manufactured by TOPCON TECHNOHOUSE CORPORATION), and electroluminescence (EL) spectra were measured with a multi-channel spectrometer (PMA-11 manufactured by Hamamatsu Photonics K.K.). Note that the measurement was carried out at room temperature (an atmosphere maintained at 23° C.). As the results of the operation characteristics of the light-emitting device 3, the comparative light-emitting device 4, and the comparative light-emitting device 5, the current density-luminance characteristics are shown in FIG. 21, the voltage-luminance characteristics are shown in FIG. 22, the luminance-current efficiency characteristics are shown in FIG. 23, the voltage-current density characteristics are shown in FIG. 24, the luminance-power efficiency characteristics are shown in FIG. 25, and the luminance-external quantum efficiency characteristics are shown in FIG. 26.

Figure 27:
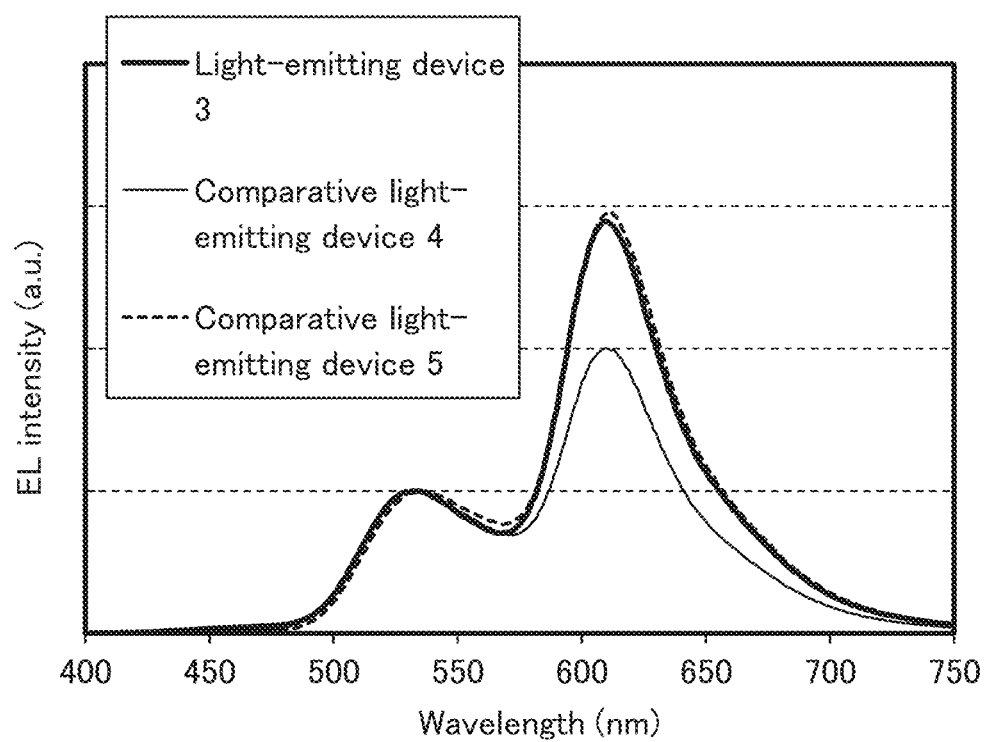
FIG. 27 is a graph showing the electroluminescence spectra of the light-emitting device 3, the comparative light-emitting device 4, and the comparative light-emitting device 5.

FIG. 27 shows the electroluminescence spectra (EL spectra) of the light-emitting devices to which current flows at a current density of 2.5 mA/cm².

Table 4 below shows the initial values of the main characteristics of each of the light-emitting devices at around 1000 cd/m².

TABLE 4

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) | External energy efficiency (%) |
|---|---|---|---|---|---|---|---|---|---|
| Light-emitting device 3 | 3.5 | 0.12 | 3.1 | (0.53, 0.45) | 880 | 28 | 25 | 13 | 7.7 |
| Comparative light-emitting device 4 | 3.6 | 0.18 | 4.5 | (0.50, 0.48) | 930 | 20 | 18 | 8.8 | 5.0 |
| Comparative light-emitting device 5 | 3.8 | 0.25 | 6.1 | (0.53, 0.46) | 1000 | 16 | 14 | 7.6 | 4.1 |

As shown in FIG. 27, each of the EL spectra of the light-emitting devices has two peaks at around 530 nm and around 610 nm. Note that in the light-emitting device 3, the peak at around 530 nm is derived from 2TMS-mmtBuDPhA2Anth whereas the peak at around 610 nm is derived from [Ir(dmdppr-dmp)$_2$(dpm)]. In the comparative light-emitting device 4 and the comparative light-emitting device 5, the peak at around 530 nm is derived from MeDPhA2A whereas the peak at around 610 nm is derived from [Ir(dmdppr-dmp)$_2$(dpm)]. This indicates that emission (fluorescence) derived from 2TMS-mmtBuDPhA2Anth and emission (phosphorescence) derived from Ir(dmdppr-dmp)$_2$(dpm) are obtained in the light-emitting device 3, and emission (fluorescence) derived from MeDPhA2A and emission (phosphorescence) derived from Ir(dmdppr-dmp)$_2$(dpm) are obtained in the comparative light-emitting device 4 and the comparative light-emitting device 5. Thus, the results of the EL spectra confirmed that emission from different guest materials was concurrently obtained in all of the devices.

As shown in FIG. 23, FIG. 25, and FIG. 26, the result on the efficiency versus luminance was superior in the light-emitting device 3 to that in the comparative light-emitting device 4 and the comparative light-emitting device 5, and the light-emitting device 3 exhibited a high external quantum efficiency exceeding 10% though the fluorescent substance is used as the guest material. This indicates that the use of the organic compound having a protecting group (the first organic compound 121 described in Embodiment 2) as the organic compound having a function of converting singlet excitation energy into light emission, which is the guest material of the light-emitting layer, inhibits transfer of triplet excitation energy from the host material to the fluorescent substance by the Dexter mechanism to inhibit deactivation of the triplet excitation energy due to the energy transfer, thereby inhibiting a decrease in the emission efficiency of the light-emitting device.

The light-emitting device 3 and the comparative light-emitting device 4 include different guest materials having a function of converting singlet excitation energy into light emission, but have the same concentration of each guest material to the host material. However, a comparison of the EL spectra of the light-emitting device 3 and the comparative light-emitting device 4 reveals that the peak at around 610 nm, which is derived from [Ir(dmdppr-dmp)$_2$(dpm)] as the guest material having a function of converting triplet excitation energy into light emission, is smaller in the comparative light-emitting device 4 than in the light-emitting device 3. This means that the triplet excitation energy in the comparative light-emitting device 4 does not contribute to light emission compared to that in the light-emitting device 3. The comparative light-emitting device 5 has a higher concentration of [Ir(dmdppr-dmp)$_2$(dpm)] than the comparative light-emitting device 4, so that the comparative light-emitting device 5 has a high relative spectrum intensity at around 610 nm and achieves an EL spectrum shape close to that of the light-emitting device 3. This is actually due to a decrease in the spectrum intensity at around 530 nm; thus, the efficiency of the comparative light-emitting device 5 is lower than that of the comparative light-emitting device 4. That is, it is difficult for both the fluorescent substance and the phosphorescent substance to emit light efficiently with a desired balance in the comparative light-emitting devices each using the fluorescent substance having no protecting group. In contrast, in the light-emitting device of one embodiment of the present invention, deactivation of triplet excitation energy can be inhibited and thus, both the fluorescent substance and the phosphorescent substance can emit light efficiently with a desired balance.

Example 3

In this example, light-emitting devices of embodiments of the present invention were fabricated and the operation characteristics of the devices were measured. Note that in a light-emitting layer of a light-emitting device 6 of one embodiment of the present invention, 9-[3-(4,6-diphenyl-1,3,5-triazin-2-yl)phenyl]-9'-phenyl-2,3'-bi-9H-carbazole (abbreviation: mPCCzPTzn-02) was used as a host material, and 2TMS-mmtBuDPhA2Anth, which is an organic compound having a protecting group and a function of converting singlet excitation energy into light emission, and [Ir(dmdppr-dmp)$_2$(dpm)], which is an organic compound having a function of converting triplet excitation energy into light emission, were used as guest materials. In a light-emitting device 7, 9-phenyl-9'-(4-phenyl-2-quinazolinyl)-3,3'-bi-9H-carbazole (abbreviation: PCCzQz) was used instead of mPCCzPTzn-02, which is the host material in the light-emitting device 6.

Note that the device structure of the light-emitting device 6 and the light-emitting device 7 fabricated in this example is similar to that in FIG. 12 shown in Example 1, and the specific composition of each layer of the device structure is as shown in Table 5. Chemical formulae of materials used in this example are shown below.

TABLE 5

|  | First electrode | Hole-injection layer | Hole-transport layer | Light-emitting layer | Electron-transport layer | Electron-injection layer | Second electrode |
|---|---|---|---|---|---|---|---|
| Light-emitting device 6 | ITSO (70 nm) | DBT3P-II:MoOx (1:0.5 40 nm) | mCzFLP (20 nm) | * | 4,6mCzP2Pm (20 nm) NBphen (10 nm) | LiF (1 nm) | Al (200 nm) |
| Light-emitting device 7 | ITSO (70 nm) | DBT3P-II:MoOx (1:0.5 40 nm) | mCzFLP (20 nm) | ** | 4,6mCzP2Pm (20 nm) NBphen (10 nm) | LiF (1 nm) | Al (200 nm) |

* mPCCzPTzn-02:2TMS-mmtBuDPhA2Anth:[Ir(dmdppr-dmp)$_2$(dpm)] (1:0.025:0.005 40 nm)

** PCCzQz:2TMS-mmtBuDPhA2Anth:[Ir(dmdppr-dmp)$_2$(dpm)] (1:0.025:0.005 40 nm)

[Chemical Formula 32]
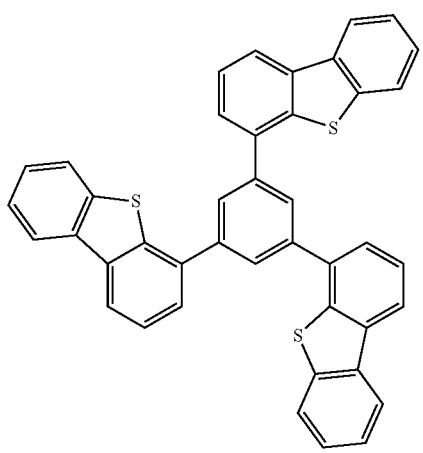
DBT3P-II
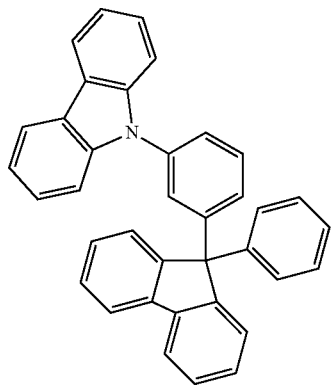
mCzFLP
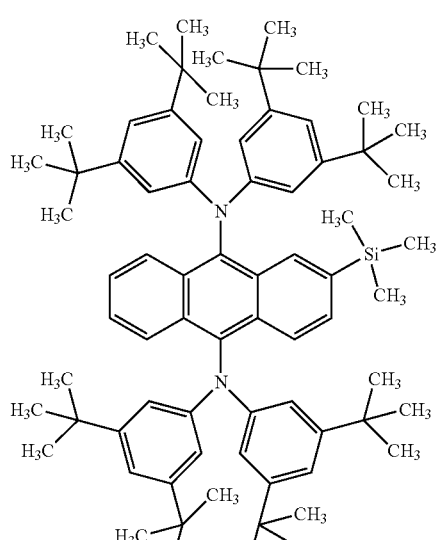
2TMS-mmtBuDPhA2Anth
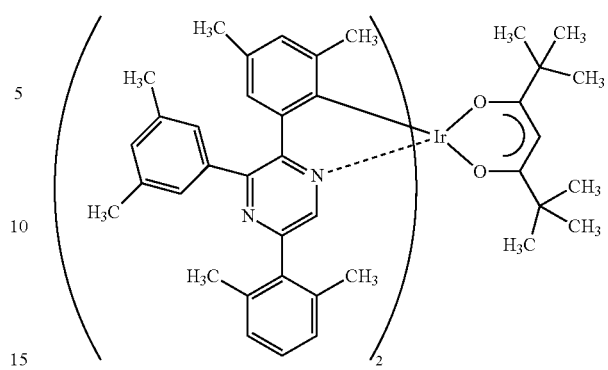
[Ir(dmdppr-dmp)₂(dpm)]
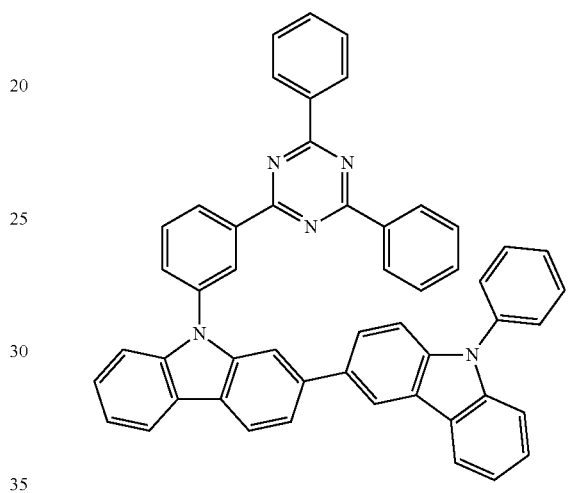
mPCCzPTzn-02
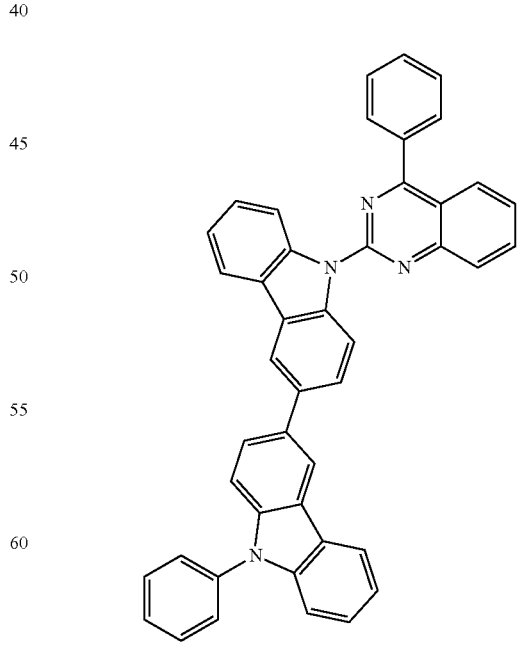
PCCzQz -continued

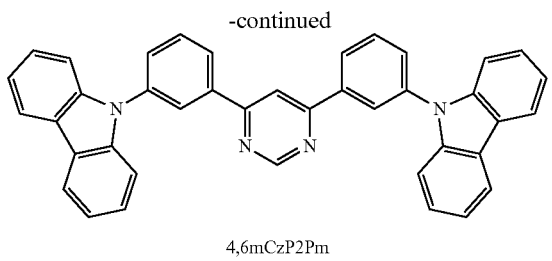

4,6mCzP2Pm

NBphen

<<Operation Characteristics of Light-Emitting Devices>>

Figure 28:
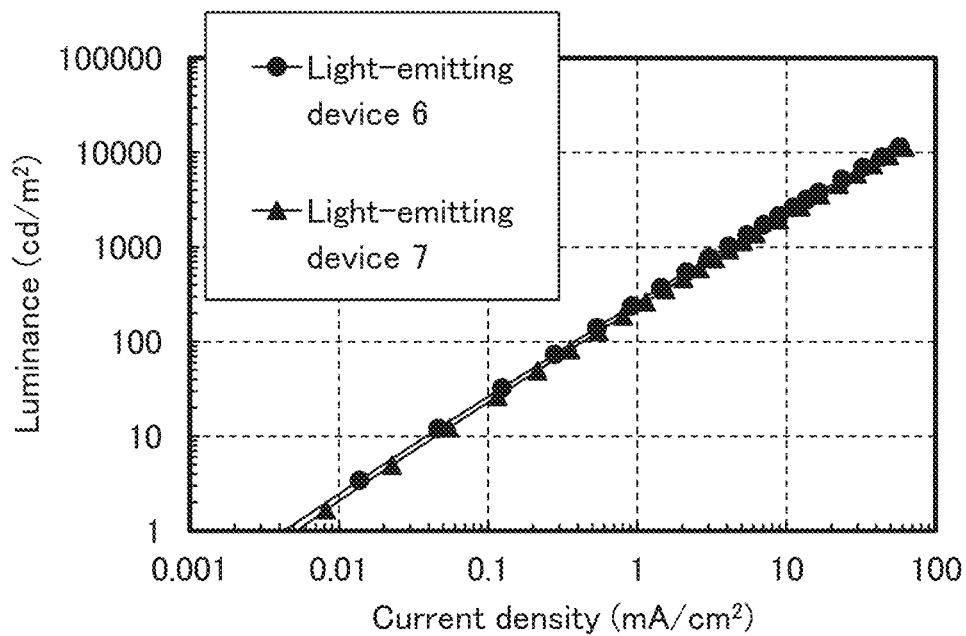
FIG. 28 is a graph showing the current density-luminance characteristics of a light-emitting device 6 and a light-emitting device 7.
Figure 29:
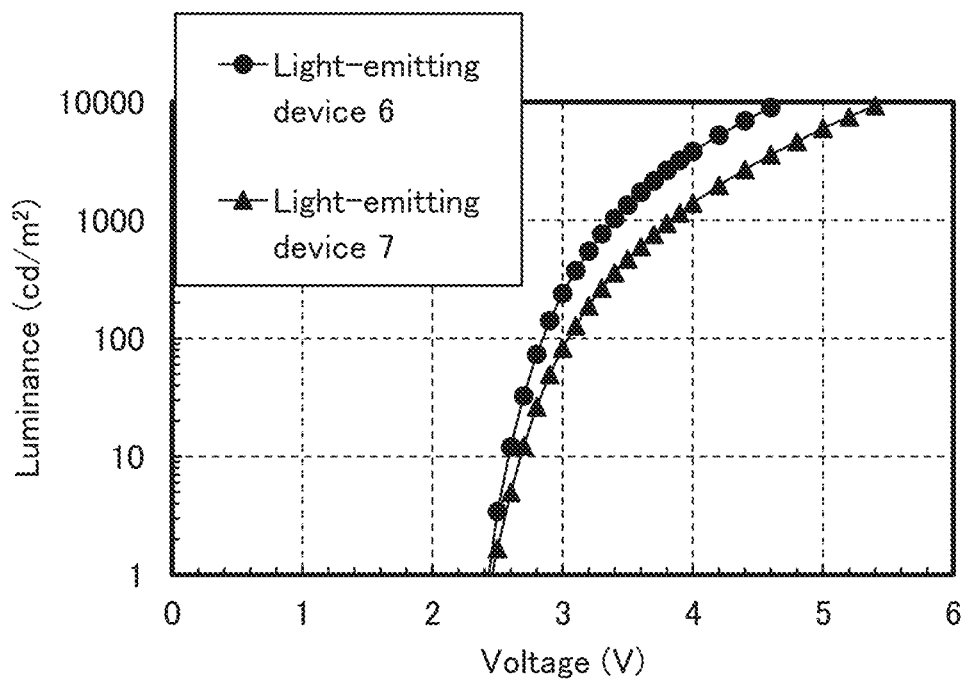
FIG. 29 is a graph showing the voltage-luminance characteristics of the light-emitting device 6 and the light-emitting device 7.
Figure 30:
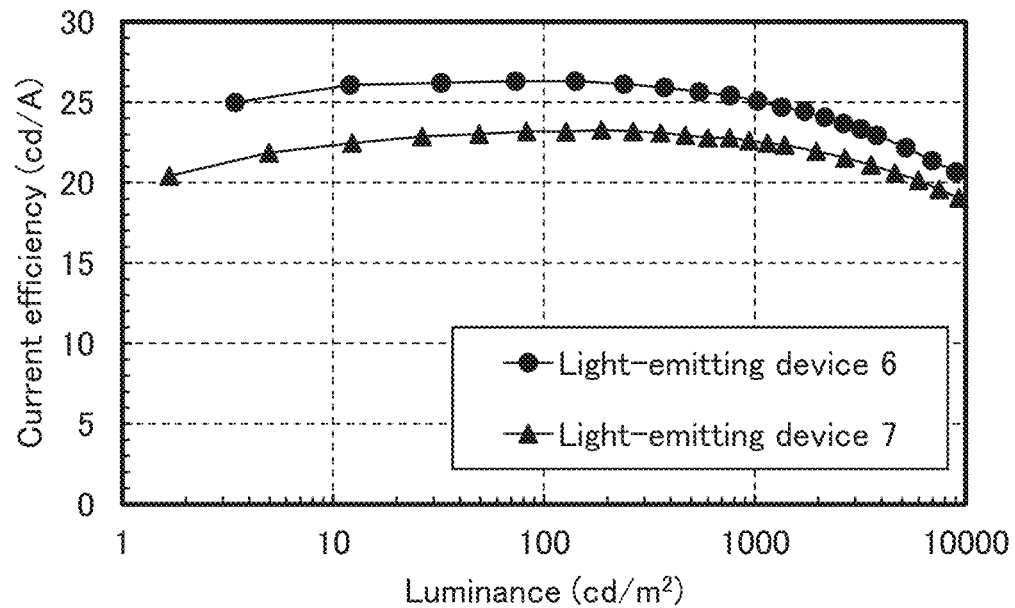
FIG. 30 is a graph showing the luminance-current efficiency characteristics of the light-emitting device 6 and the light-emitting device 7.
Figure 31:
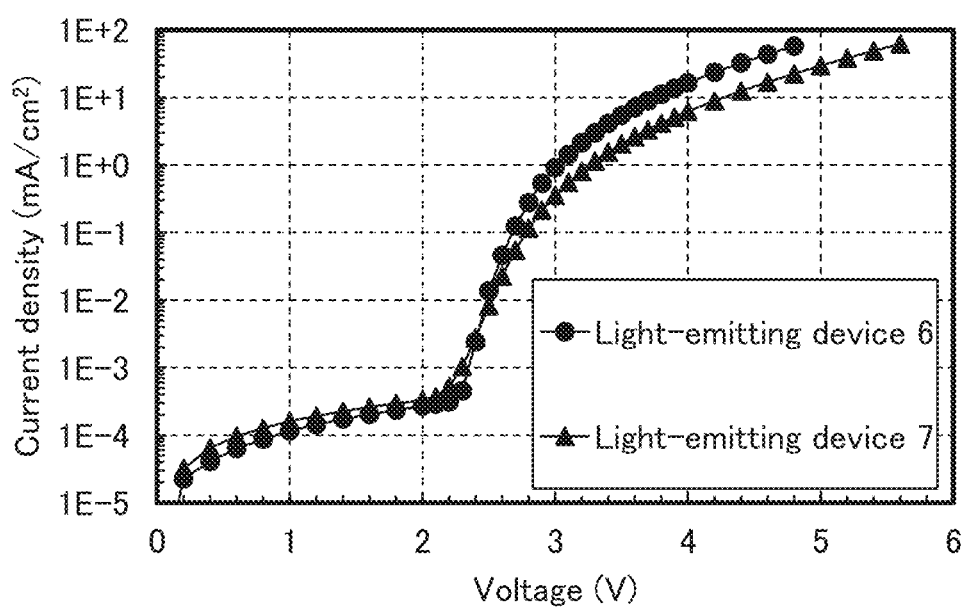
FIG. 31 is a graph showing the voltage-current density characteristics of the light-emitting device 6 and the light-emitting device 7.
Figure 32:
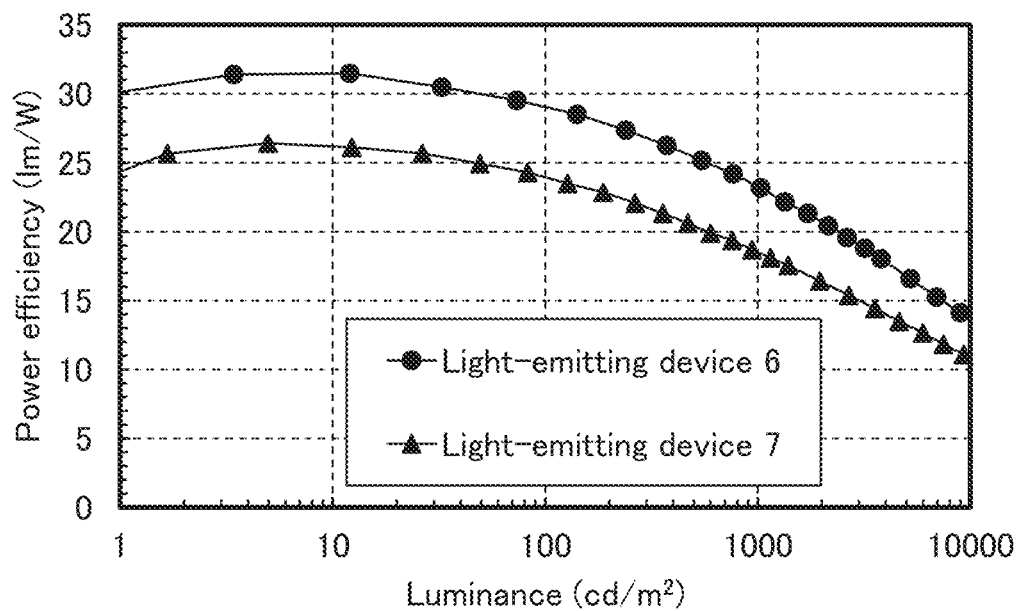
FIG. 32 is a graph showing the luminance-power efficiency characteristics of the light-emitting device 6 and the light-emitting device 7.
Figure 33:
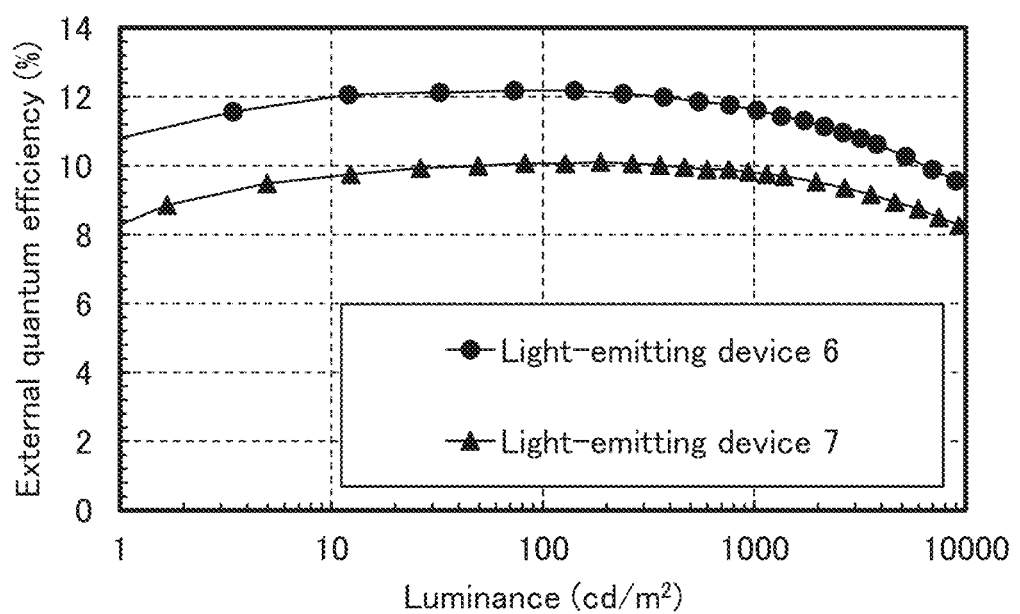
FIG. 33 is a graph showing the luminance-external quantum efficiency characteristics of the light-emitting device 6 and the light-emitting device 7.

Operation characteristics of the fabricated light-emitting devices were measured. Luminance and chromaticity (CIE chromaticity) were measured with a luminance colorimeter (BM-5A manufactured by TOPCON TECHNOHOUSE CORPORATION), and electroluminescence (EL) spectra were measured with a multi-channel spectrometer (PMA-11 manufactured by Hamamatsu Photonics K.K.). Note that the measurement was carried out at room temperature (an atmosphere maintained at 23° C.). As the results of the operation characteristics of the light-emitting device 6 and the light-emitting device 7, the current density-luminance characteristics are shown in FIG. 28, the voltage-luminance characteristics are shown in FIG. 29, the luminance-current efficiency characteristics are shown in FIG. 30, the voltage-current density characteristics are shown in FIG. 31, the luminance-power efficiency characteristics are shown in FIG. 32, and the luminance-external quantum efficiency characteristics are shown in FIG. 33.

Figure 34:
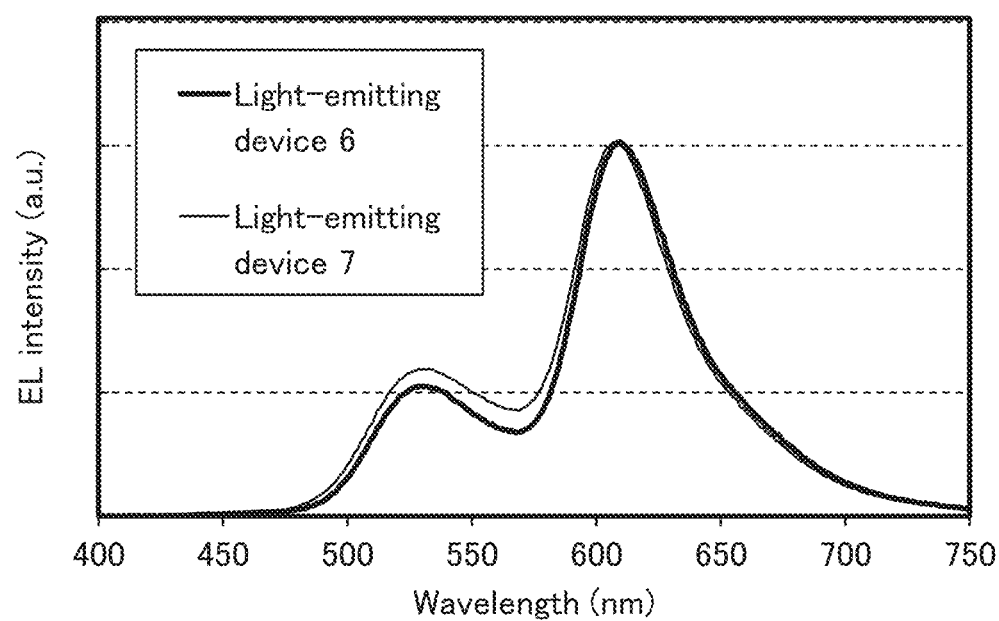
FIG. 34 is a graph showing the electroluminescence spectra of the light-emitting device 6 and the light-emitting device 7.

FIG. 34 shows the electroluminescence spectra (EL spectra) of the light-emitting devices to which current flows at a current density of 2.5 mA/cm$^2$.

Table 6 below shows the initial values of the main characteristics of each of the light-emitting devices at around 1000 cd/m$^2$.

As shown in FIG. 34, each of the EL spectra of the light-emitting devices has two peaks at around 530 nm and around 610 nm. Note that in the light-emitting device 6 and the light-emitting device 7, the peak at around 530 nm is derived from 2TMS-mmtBuDPhA2Anth whereas the peak at around 610 nm is derived from [Ir(dmdppr-dmp)$_2$(dpm)]. This indicates that emission (fluorescence) derived from 2TMS-mmtBuDPhA2Anth and emission (phosphorescence) derived from Ir(dmdppr-dmp)$_2$(dpm) are obtained in the light-emitting device 6 and the light-emitting device 7. Thus, the results of the EL spectra confirmed that emission from different guest materials was concurrently obtained in both of the devices.

As shown in FIG. 33, the light-emitting device 6 and the light-emitting device 7 exhibited a high external quantum efficiency exceeding at most 10% though the fluorescent substance is used as the guest material. This is because the use of the organic compound having a protecting group (the first organic compound 121 described in Embodiment 2) as the organic compound having a function of converting singlet excitation energy into light emission, which is the guest material of the light-emitting layer, inhibits transfer of triplet excitation energy from the host material to the fluorescent substance by the Dexter mechanism to inhibit deactivation of the triplet excitation energy due to the energy transfer, thereby inhibiting a decrease in the emission efficiency of the light-emitting devices. As shown in FIG. 30, FIG. 32, and FIG. 33, the result on the efficiency versus luminance of each light-emitting device was superior in the light-emitting device 6 to that in the light-emitting device 7. In this example, the structure of the light-emitting device 6 is different from that of the light-emitting device 7 only in the host material of the light-emitting layer. The host material used in the light-emitting layer of the light-emitting device 6 is mPCCzPTzn-02 and the host material used in the light-emitting layer of the light-emitting device 7 is PCCzQz. In order to obtain the T1 level of the host material, a thin film of each organic compound was formed over a quartz substrate by a vacuum evaporation method, and the emission spectrum of the thin film was measured at a low temperature (10 K). For the measurement, a PL microscope, LabRAM HR-PL (HORIBA, Ltd.) was used, the measurement temperature was 10 K, a He—Cd laser having a wavelength of 325 nm was used as excitation light, and a CCD was used as a detector. The T1 level was calculated from the energy with the wavelength of a line obtained by extrapolating a tangent to the emission spectrum, which was measured at a low temperature, at a tail on the short wavelength side; as a result, the T1 level of mPCCzPTzn-02 was 2.59 eV (478 nm) and the T1 level of PCCzQz was 2.38 eV (521 nm). The T1 level of mPCCzPTzn-02 is higher than the T1 level of PCCzQz, that is, the light-emitting device 6 has higher efficiency than the light-emitting device 7. In addition, the light-emitting device 6 and the light-emitting

TABLE 6

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) | External energy efficiency (%) |
|---|---|---|---|---|---|---|---|---|---|
| Light-emitting device 6 | 3.4 | 0.16 | 4.1 | (0.53, 0.45) | 1000 | 25 | 23 | 12 | 7 |
| Light-emitting device 7 | 3.8 | 0.17 | 4.2 | (0.52, 0.47) | 940 | 23 | 19 | 10 | 5.4 | device 7 were driven at a constant current of 2.0 mA; as a result, the time (LT80) reaching a relative luminance of 80% with the initial luminance assumed to be 100% was 39 hours in the light-emitting device 6 and 156 hours in the light-emitting device 7. As described above, the light-emitting devices of embodiments of the present invention can have favorable reliability.

Reference Synthesis Example 1

In this reference synthesis example, a synthesis method of 2-trimethylsilyl-N,N,N',N'-tetrakis(3,5-di-tert-butylphenyl)-9,10-anthracenediamine (abbreviation: 2TMS-mmtBuDPhA2Anth) (Structural Formula (229)), which is the organic compound used in Examples above, will be described.

Step 1: Synthesis of 9,10-dibromo-2-trimethylsilylanthracene

First, 2.7 g (11 mmol) of 2-trimethylsilylanthracene was put into a 500 mL three-neck flask, and the atmosphere in the flask was replaced with nitrogen. Then, 110 mL of N,N'-dimethyl sulfoxide was added thereto, and the mixture was stirred at room temperature. Then, 4.0 g (23 mmol) of N-bromosuccinimide was added thereto, and the mixture was stirred at room temperature for 15 hours. After the stirring, water was added to the reaction mixture to give an aqueous layer and an organic layer. The aqueous layer was subjected to extraction with toluene, and the obtained extracted solution and the organic layer were combined. The mixed solution of the extracted solution and the organic layer was washed with water and a saturated aqueous solution of sodium thiosulfate, and then drying was performed with magnesium sulfate. This mixture was separated by gravity filtration, and the filtrate was concentrated to give a yellow brown solid. After 450 mL of hexane and 50 mL of toluene were added to the obtained yellow brown solid, suction filtration was performed through Florisil (Wako Pure Chemical Industries, Ltd., Catalog Number: 066-05265), Celite (Wako Pure Chemical Industries, Ltd., Catalog Number: 537-02305) and aluminum oxide to give a filtrate. The obtained filtrate was concentrated to give a yellow brown solid. The obtained solid was recrystallized with ethyl acetate/ethanol, whereby 2.4 g of a yellow solid was obtained in a yield of 54%. The synthesis scheme of Step 1 is shown in (F-1) below.

Results of $^1$H-NMR measurement of the yellow solid obtained in Step 1 above will be described below. The results indicate that 9,10-dibromo-2-trimethylsilylanthracene was obtained.

$^1$H-NMR (CDCl$_3$, 300 MHz): σ=8.74 (s, 1H), 8.63-8.56 (m, 2H), 8.55 (d, J=8.8 Hz, 1H), 7.75 (d, J=8.3 Hz, 1H), 7.68-7.61 (m, 2H), 0.42 (s, 9H).

Step 2: Synthesis of 2TMS-mmtBuDPhA2Anth

First, 1.4 g (3.3 mmol) of 9,10-dibromo-2-trimethylsilylanthracene, 2.6 g (6.6 mmol) of bis(3,5-tert-butylphenyl)amine, 1.3 g (14 mmol) of sodium t-butoxide, and 60 mg (0.15 mmol) of 2-dicyclohexylphosphino-2',6'-dimethoxy-1,1'-biphenyl (abbreviation: SPhos) were put into a 200 mL three-neck flask, and the air in the flask was replaced with nitrogen. To this mixture was added 33 mL of xylene, and the mixture was degassed under reduced pressure; then, 40 mg (70 mol) of bis(dibenzylideneacetone)palladium(0) was added to the mixture and the mixture was stirred for 6 hours at 150° C. under a nitrogen stream. After the stirring, 400 mL of toluene was added to the obtained mixture, which was then subjected to suction filtration through Florisil, Celite, and aluminum oxide to give a filtrate. The obtained filtrate was concentrated to give a brown solid. This solid was purified by silica gel column chromatography (developing solvent: hexane:toluene=9:1) to give a yellow solid. The obtained yellow solid was recrystallized with ethyl acetate and ethanol to give 0.40 g of an objective yellow solid in a yield of 12%. The synthesis scheme of Step 2 is shown in (F-2) below.

[Chemical Formula 34]

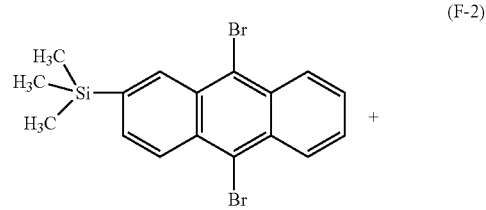

[Chemical Formula 33]

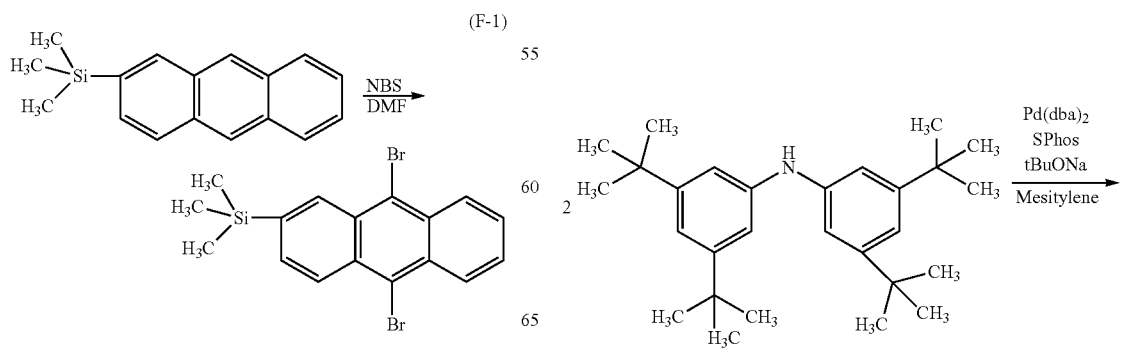

-continued

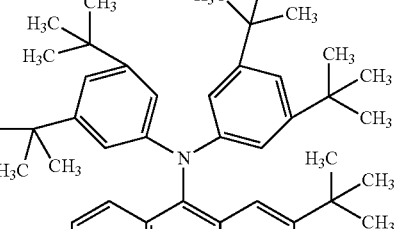

By a train sublimation method, 0.40 g of the obtained yellow solid was purified by sublimation. In the sublimation purification, the yellow solid was heated at 260° C. under a pressure of 3.5 Pa for 15 hours. After the sublimation purification, 0.35 g of an objective yellow solid was obtained at a collection rate of 87%.

Results of $^1$H-NMR measurement of the yellow solid obtained in Step 2 above will be described below. The results indicate that 2TMS-mmtBuDPhA2Anth was obtained.

$^1$H-NMR (CDCl$_3$, 300 MHz): σ=8.25 (s, 1H), 8.24-8.21 (m, 1H), 8.15-8.11 (m, 2H), 7.40-7.37 (m, 1H), 7.30-7.27 (m, 2H), 6.97-6.94 (m, 8H), 6.92-6.91 (m, 4H), 1.14 (s, 36H), 1.12 (m, 36H), 0.09 (s, 9H).

REFERENCE NUMERALS

101: first electrode, 102: second electrode, 103: EL layer, 103a, 103b: EL layer, 104: charge-generation layer, 111, 111a, 111b: hole-injection layer, 112, 112a, 112b: hole-transport layer, 113, 113a, 113b: light-emitting layer, 114, 114a, 114b: electron-transport layer, 115, 115a, 115b: electron-injection layer, 121: first organic compound, 122: second organic compound, 123: third organic compound, 124: fluorescent substance, 130a, 130b: luminophore, 131: protecting group, 200R, 200G, 200B: optical path length, 201: first substrate, 202: transistor (FET), 203R, 203G, 203B, 203W: light-emitting device, 204: EL layer, 205: second substrate, 206R, 206G, 206B: color filter, 206R', 206G', 206B': color filter, 207: first electrode, 208: second electrode, 209: black layer (black matrix), 210R, 210G: conductive layer, 301: first substrate, 302: pixel portion, 303: driver circuit portion (source line driver circuit), 304a, 304b: driver circuit portion (gate line driver circuit), 305: sealant, 306: second substrate, 307: lead wiring, 308: FPC, 309: FET, 310: FET, 311: FET, 312: FET, 313: first electrode, 314: insulator, 315: EL layer, 316: second electrode, 317: light-emitting device, 318: space, 900: substrate, 901: first electrode, 902: EL layer, 903: second electrode, 911: hole-injection layer, 912: hole-transport layer, 913: light-emitting layer, 914: electron-transport layer, 915: electron-injection layer, 4000: lighting device, 4001: substrate, 4002: light-emitting device, 4003: substrate, 4004: first electrode, 4005: EL layer, 4006: second electrode, 4007: electrode, 4008: electrode, 4009: auxiliary wiring, 4010: insulating layer, 4011: sealing substrate, 4012: sealant, 4013: desiccant, 4200: lighting device, 4201: substrate, 4202: light-emitting device, 4204: first electrode, 4205: EL layer, 4206: second electrode, 4207: electrode, 4208: electrode, 4209: auxiliary wiring, 4210: insulating layer, 4211: sealing substrate, 4212: sealant, 4213: barrier film, 4214: planarization film, 5101: light, 5102: wheel, 5103: door, 5104: display portion, 5105: steering wheel, 5106: shifter, 5107: seat, 5108: inner rearview mirror, 5109: windshield, 7000: housing, 7001: display portion, 7002: second display portion, 7003: speaker, 7004: LED lamp, 7005: operation key, 7006: connection terminal, 7007: sensor, 7008: microphone, 7009: switch, 7010: infrared port, 7011: recording medium reading portion, 7013: earphone, 7014: antenna, 7015: shutter button, 7016: image receiving portion, 7018: stand, 7020: camera, 7022, 7023: operation button, 7024: connection terminal, 7025: band, 7026: microphone, 7029: sensor, 7030: speaker, 7052, 7053, 7054: information, 9310: portable information terminal, 9311: display portion, 9312: display region, 9313: hinge, 9315: housing

The invention claimed is:
1. A light-emitting device comprising an EL layer between a pair of electrodes,
wherein the EL layer comprises a light-emitting layer,
wherein the light-emitting layer comprises a first organic compound having a function of converting singlet excitation energy into light emission and a second organic compound having a function of converting triplet excitation energy into light emission,
wherein the first organic compound is represented by General Formula (G2),

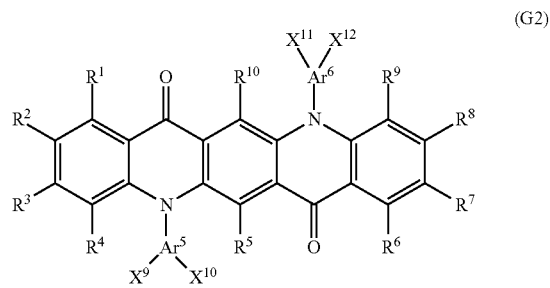

wherein Ar$^5$ or Ar$^6$ each independently represent a substituted or unsubstituted aromatic hydrocarbon group having 6 to 13 carbon atoms, X$^9$ to X$^{12}$ each independently represent any one of an alkyl group having 1 to 10 carbon atoms, a substituted or unsubstituted cycloalkyl group having 3 to 10 carbon atoms, and a trialkylsilyl group having 3 to 10 carbon atoms, and R$^1$ to R$^{10}$ each independently represent any one of hydrogen, an alkyl group having 3 to 10 carbon atoms, a substituted or unsubstituted cycloalkyl group having 3 to 10 carbon atoms, and a trialkylsilyl group having 3 to 12 carbon atoms, and
wherein a lowest singlet excitation energy level (S1 level) of the first organic compound is higher than a lowest triplet excitation energy level (T1 level) of the second organic compound.

2. The light-emitting device according to claim 1,
wherein the light-emitting layer further comprises a third organic compound,
wherein a lowest singlet excitation energy level (S1 level) of the third organic compound is higher than the lowest singlet excitation energy level (S1 level) of the first organic compound, and
wherein a lowest triplet excitation energy level (T1 level) of the third organic compound is higher than the lowest triplet excitation energy level (T1 level) of the second organic compound.

3. The light-emitting device according to claim 1,
wherein the light-emitting layer further comprises a fourth organic compound and a fifth organic compound, and
wherein the fourth organic compound and the fifth organic compound form an exciplex.

4. The light-emitting device according to claim 1,
wherein the alkyl group is a branched-chain alkyl group.

5. A light-emitting apparatus comprising:
the light-emitting device according to claim 1; and
at least one of a transistor and a substrate.

6. An electronic device comprising:
the light-emitting apparatus according to claim 5; and
at least one of a microphone, a camera, an operation button, an external connection portion, and a speaker.

7. A lighting device comprising:
the light-emitting device according to claim 1; and
at least one of a housing, a cover, and a support.

8. A light-emitting device comprising an EL layer between a pair of electrodes,
wherein the EL layer comprises a light-emitting layer,
wherein the light-emitting layer comprises a first organic compound having a function of converting singlet excitation energy into light emission and a second organic compound having a function of converting triplet excitation energy into light emission,
wherein the first organic compound is represented by General Formula (G4),

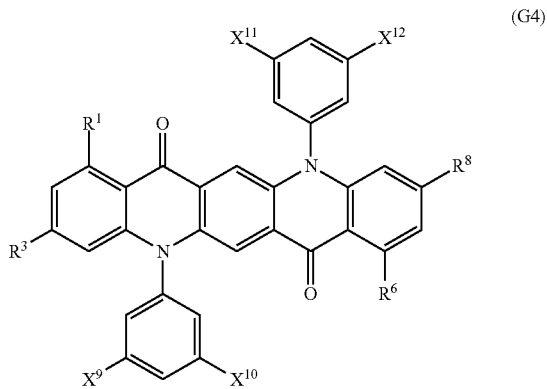

(G4)

wherein $X^9$ to $X^{12}$ each independently represent any one of an alkyl group having 1 to 10 carbon atoms, a substituted or unsubstituted cycloalkyl group having 3 to 10 carbon atoms, and a trialkylsilyl group having 3 to 10 carbon atoms, and $R^1$, $R^3$, $R^6$, and $R^8$ each independently represent any one of hydrogen, an alkyl group having 3 to 10 carbon atoms, a substituted or unsubstituted cycloalkyl group having 3 to 10 carbon atoms, and a trialkylsilyl group having 3 to 12 carbon atoms, and wherein a lowest singlet excitation energy level (S1 level) of the first organic compound is higher than a lowest triplet excitation energy level (T1 level) of the second organic compound.

9. The light-emitting device according to claim 8,
wherein the light-emitting layer further comprises a third organic compound,
wherein a lowest singlet excitation energy level (S1 level) of the third organic compound is higher than the lowest singlet excitation energy level (S1 level) of the first organic compound, and
wherein a lowest triplet excitation energy level (T1 level) of the third organic compound is higher than the lowest triplet excitation energy level (T1 level) of the second organic compound.

10. The light-emitting device according to claim 8,
wherein the light-emitting layer further comprises a fourth organic compound and a fifth organic compound, and
wherein the fourth organic compound and the fifth organic compound form an exciplex.

11. The light-emitting device according to claim 8,
wherein the alkyl group is a branched-chain alkyl group.

12. A light-emitting apparatus comprising:
the light-emitting device according to claim 8; and
at least one of a transistor and a substrate.

13. An electronic device comprising:
the light-emitting apparatus according to claim 12; and
at least one of a microphone, a camera, an operation button, an external connection portion, and a speaker.

14. A lighting device comprising:
the light-emitting device according to claim 8; and
at least one of a housing, a cover, and a support.

* * * * *